(12) United States Patent
Asakawa et al.

(10) Patent No.: US 11,073,762 B2
(45) Date of Patent: *Jul. 27, 2021

(54) ACTINIC RAY-SENSITIVE OR RADIATION SENSITIVE RESIN COMPOSITION, ACTINIC RAYSENSITIVE OR RADIATION-SENSITIVE FILM, PATTERN FORMING METHOD, METHOD FOR MANUFACTURING ELECTRONIC DEVICE, AND PHOTOACID GENERATOR

(71) Applicant: FUJIFILM Corporation, Tokyo (JP)

(72) Inventors: Daisuke Asakawa, Shizuoka (JP); Akiyoshi Goto, Shizuoka (JP); Masafumi Kojima, Shizuoka (JP); Keita Kato, Shizuoka (JP); Keiyu Ou, Shizuoka (JP); Kyohei Sakita, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 99 days.

This patent is subject to a terminal disclaimer.

(21) Appl. No.: 16/432,279

(22) Filed: Jun. 5, 2019

(65) Prior Publication Data

US 2019/0294043 A1   Sep. 26, 2019

Related U.S. Application Data

(63) Continuation of application No. PCT/JP2017/044599, filed on Dec. 12, 2017.

(30) Foreign Application Priority Data

Dec. 22, 2016 (JP) .............................. JP2016-250128
Apr. 28, 2017 (JP) .............................. JP2017-090817

(51) Int. Cl.
| | | |
|---|---|---|
| G03F 7/038 | (2006.01) | |
| G03F 7/004 | (2006.01) | |
| G03F 7/039 | (2006.01) | |
| G03F 7/20 | (2006.01) | |
| C09K 3/00 | (2006.01) | |
| C08F 220/26 | (2006.01) | |
| C07C 309/17 | (2006.01) | |
| C07C 381/12 | (2006.01) | |
| C07C 309/12 | (2006.01) | |
| C07C 309/19 | (2006.01) | |

(52) U.S. Cl.
CPC ............ *G03F 7/038* (2013.01); *C08F 220/26* (2013.01); *C09K 3/00* (2013.01); *G03F 7/004* (2013.01); *G03F 7/0045* (2013.01); *G03F 7/039* (2013.01); *G03F 7/20* (2013.01); *C07C 309/12* (2013.01); *C07C 309/17* (2013.01); *C07C 309/19* (2013.01); *C07C 381/12* (2013.01); *G03F 7/2053* (2013.01)

(58) Field of Classification Search
CPC .......... G03F 7/038; G03F 7/039; G03F 7/004; G03F 7/20; G03F 7/0045; G03F 7/2053; G03F 7/0397; G03F 7/0392; C09K 3/00; C08F 220/26; C07C 309/17; C07C 381/12; C07C 309/12; C07C 309/19
USPC ............................................... 430/270.1, 311
See application file for complete search history.

(56) References Cited

U.S. PATENT DOCUMENTS

| | | |
|---|---|---|
| 2012/0156617 A1 | 6/2012 | Kataoka et al. |
| 2012/0164582 A1 | 6/2012 | Maruyama |
| 2013/0017377 A1 | 1/2013 | Kataoka et al. |
| 2013/0078579 A1 | 3/2013 | Asano |
| 2014/0342288 A1 | 11/2014 | Tomioka et al. |
| 2015/0338736 A1 | 11/2015 | Kawabata et al. |
| 2016/0154314 A1 | 6/2016 | Hatakeyama et al. |
| 2016/0320698 A1 | 11/2016 | Fujiwara et al. |
| 2017/0038679 A1 | 2/2017 | Tomioka et al. |
| 2019/0294042 A1* | 9/2019 | Kato ....................... G03F 7/038 |

FOREIGN PATENT DOCUMENTS

| | | |
|---|---|---|
| JP | 2011-100105 A | 5/2011 |
| JP | 2011-203644 A | 10/2011 |
| JP | 2013-83944 A | 5/2013 |
| JP | 2014-126767 A | 7/2014 |
| JP | 2014-167579 A | 9/2014 |
| JP | 2015-4967 A | 1/2015 |
| JP | 2016-110088 A | 6/2016 |
| JP | 2016-210761 A | 12/2016 |
| TW | 201432382 A | 8/2014 |
| WO | 2011/030737 A1 | 3/2011 |

OTHER PUBLICATIONS

International Search Report dated Feb. 27, 2018 by the International Search ing Authority in counterpart International Patent Application No. PCT/JP2017/044599. (PCT/ISA/210).
Written Opinion dated Feb. 27, 2018 by the International Search ing Authority in counterpart International Patent Application No. PCT/JP2017/044599. (PCT/ISA/237).
Office Action dated Jun. 30, 2020 by the Japanese Patent Office in counterpart Japanese Patent Application No. 2018-557700.
Office Action dated Mar. 16, 2021, issued by the Korean Intellectual Property Office in Korean Application No. 10-2019-7017475.

(Continued)

*Primary Examiner* — Caleen O Sullivan
(74) *Attorney, Agent, or Firm* — Sughrue Mion, PLLC

(57) ABSTRACT

Provided are an actinic ray-sensitive or radiation-sensitive resin composition which contains (A) a photoacid generator that generates an acid having a pKa of −1.40 or more upon irradiation with actinic rays or radiation, and (B) a resin having a repeating unit containing an acid-decomposable group, in which an Eth sensitivity of the repeating unit containing an acid-decomposable group is 5.64 or less, and which can provide very excellent roughness performance, exposure latitude, and depth of focus, particularly, in the formation of an ultrafine pattern; a photoacid generator; and an actinic ray-sensitive or radiation-sensitive film, a pattern forming method, and a method for manufacturing an electronic device, each using the actinic ray-sensitive or radiation-sensitive resin composition.

9 Claims, No Drawings

(56) References Cited

OTHER PUBLICATIONS

Office Action dated Jan. 26, 2021, Issued by the Japan Patent Office in counterpart Japanese Patent Application No. 2018-557700.
Office Action dated Apr. 7, 2021 by the Intellectual Property Office of Taiwan in counterpart Taiwan Patent Application No. 106144934.

* cited by examiner

ACTINIC RAY-SENSITIVE OR RADIATION SENSITIVE RESIN COMPOSITION, ACTINIC RAYSENSITIVE OR RADIATION-SENSITIVE FILM, PATTERN FORMING METHOD, METHOD FOR MANUFACTURING ELECTRONIC DEVICE, AND PHOTOACID GENERATOR

CROSS REFERENCE TO RELATED APPLICATIONS

This is a continuation of International Application NO. PCT/JP2017/044599 filed on Dec. 12, 2017, and claims priorities from Japanese Patent Application (JP2016-250128) filed on Dec. 22, 2016 and Japanese Patent Application (JP2017-090817) filed on Apr. 28, 2017, the disclosures of which are incorporated herein by reference.

BACKGROUND OF THE INVENTION

1. Field of the Invention

The present invention relates to an actinic ray-sensitive or radiation-sensitive resin composition, an actinic ray-sensitive or radiation-sensitive film, a pattern forming method, a method for manufacturing an electronic device, and a photoacid generator.

2. Description of the Related Art

An actinic ray-sensitive or radiation-sensitive resin composition is a pattern forming material that generates an acid in an exposed area upon irradiation with radiation such as far ultraviolet rays, and changes the solubility with respect to a developer in an area irradiated with actinic radiation and an area not irradiated with actinic radiation by a reaction catalyzed by the acid, thereby forming a pattern on a substrate.

In a case where an KrF excimer laser is used as an exposure light source, a resin having poly(hydroxystyrene) as a basic skeleton, which has a small absorption in a region at 248 nm, is usually used as a main component, and therefore, a good pattern is formed with high sensitivity and high resolution, which is thus in a better system, as compared with a naphthoquinone diazide/novolac resin system in the related art.

On the other hand, in a case where an additional light source at a short wavelength, for example, an ArF excimer laser (193 nm), is used as an exposure light source, a compound having an aromatic group basically exhibits significant absorption in a region at 193 nm, which was thus not sufficient for the chemically amplified system. In this regard, for example, a resist for an ArF excimer laser that contains a resin having an alicyclic hydrocarbon structure has been developed.

A photoacid generator which is a main component of the actinic ray-sensitive or radiation-sensitive resin composition is a compound which absorbs light to generate an acid. In the field of photoresist materials, a sulfonium salt constituted with a counter anion ($X^-$) to a sulfonium cation has been widely used as a photoacid generator (see, for example, WO2011/030737A).

SUMMARY OF THE INVENTION

On the other hand, under the circumstances where various types of electronic equipment have recently been required to have higher functions, there has been a demand for the manufacture of finer wirings, and correspondingly, there has also been a demand for a further improvement in roughness performance, an exposure latitude, and a depth of focus (DOF) of a resist pattern.

Therefore, the present invention has an object to provide an actinic ray-sensitive or radiation-sensitive resin composition which can provide very excellent roughness performance, exposure latitude, and depth of focus, particularly, in the formation of an ultrafine pattern (for example, a contact hole pattern having a hole diameter of 45 nm or less, or a line-and-space pattern having a line width of 45 nm or less); a photoacid generator; and an actinic ray-sensitive or radiation-sensitive film, a pattern forming method, and a method for manufacturing an electronic device, each using the actinic ray-sensitive or radiation-sensitive resin composition.

That is, the present invention has the following configurations, by which the object of the present invention is accomplished.

[1] An actinic ray-sensitive or radiation-sensitive resin composition comprising: (A) a photoacid generator that generates an acid having a pKa of −1.40 or more upon irradiation with actinic rays or radiation; and (B) a resin having a repeating unit containing an acid-decomposable group, in which an Eth sensitivity of the repeating unit containing an acid-decomposable group is 5.64 or less.

[2] The actinic ray-sensitive or radiation-sensitive resin composition as described in [1], in which the acid having a pKa of −1.40 or more is a sulfonic acid.

[3] The actinic ray-sensitive or radiation-sensitive resin composition as described in [2], in which the sulfonic acid is an alkyl sulfonic acid in which one fluorine atom is bonded to a carbon atom at an α-position of a sulfonic acid group.

[4] The actinic ray-sensitive or radiation-sensitive resin composition as described in [2], in which the acid generated by the photoacid generator (A) upon irradiation with actinic rays or radiation is a sulfonic acid represented by any one of General Formula (a), (b) and (I) to (V),

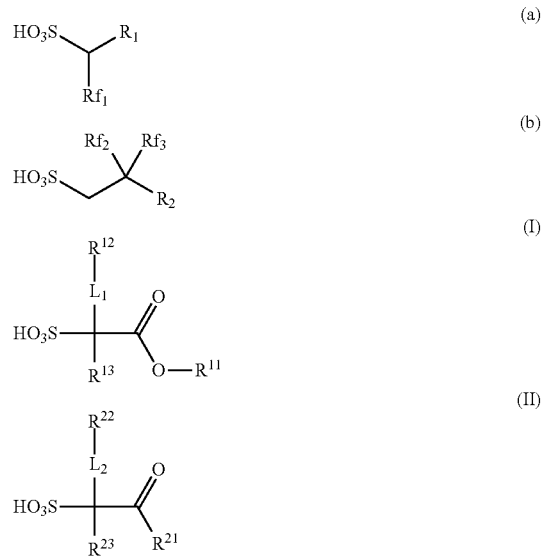

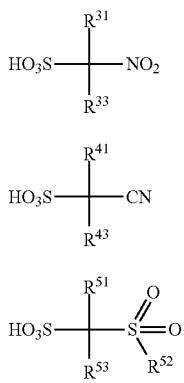

(III)

(IV)

(V)

in General Formula (a), $Rf_1$ represents a fluorine atom or an alkyl group containing a fluorine atom, and $Rf_1$ represents a monovalent organic group, in General Formula (b), $Rf_2$ and $Rf_3$ each independently represent a fluorine atom or an alkyl group containing a fluorine atom, and $R_2$ represents a monovalent organic group, in General Formula (I), $R^{11}$ and $R^{12}$ each independently represent a monovalent organic group, $R^{13}$ represents a hydrogen atom or a monovalent organic group, $L_1$ represents a group represented by —CO—O—, —CO—, —O—, —S—, —O—CO—, —S—CO—, or —CO—S—, and two of $R^{11}$, $R^{12}$, and $R^{13}$ may be bonded to each other to form a ring, in General Formula (II), $R^{21}$ and $R^{22}$ each independently represent a monovalent organic group, $R^{23}$ represents a hydrogen atom or a monovalent organic group, $L_2$ represents a group represented by —CO—, —O—, —S—, —O—CO—, —S—CO—, or —CO—S—, and two of $R^{21}$, $R^{22}$, and $R^{23}$ may be bonded to each other to form a ring, in General Formula (III), $R^{31}$ and $R^{33}$ each independently represent a hydrogen atom or a monovalent organic group, and $R^{31}$ and $R^{33}$ may be bonded to each other to form a ring, in General Formula (IV), $R^{41}$ and $R^{43}$ each independently represent a hydrogen atom or a monovalent organic group, and $R^{41}$ and $R^{43}$ may be bonded to each other to form a ring, and in General Formula (V), $R^{51}$, $R^{52}$, and $R^{53}$ each independently represent a hydrogen atom or a monovalent organic group, and two of $R^{51}$, $R^{52}$, and $R^{53}$ may be bonded to each other to form a ring.

[5] The actinic ray-sensitive or radiation-sensitive resin composition as described in any one of [1] to [4], in which the resin (B) is a resin having a repeating unit represented by General Formula (A) or (B) as the repeating unit containing an acid-decomposable group,

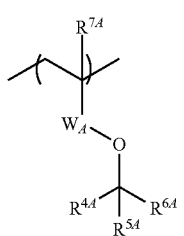

(A)

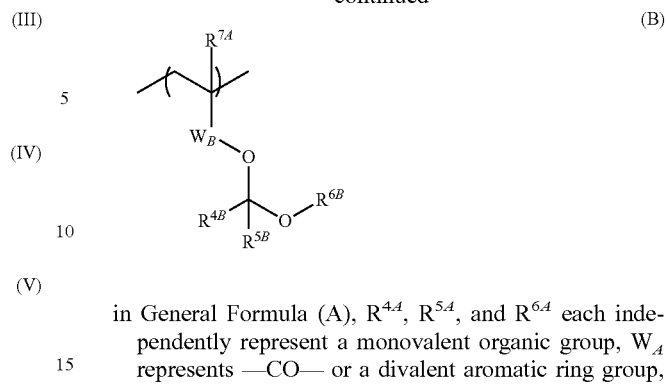

(B)

in General Formula (A), $R^{4A}$, $R^{5A}$, and $R^{6A}$ each independently represent a monovalent organic group, $W_A$ represents —CO— or a divalent aromatic ring group, $R^{7A}$ represents a hydrogen atom, a methyl group, or a trifluoromethyl group, and $R^{5A}$ and $R^{6A}$ may be bonded to each other to form a ring, and in General Formula (B), $R^{4B}$, $R^{5B}$, and $R^{6B}$ each independently represent a hydrogen atom or a monovalent organic group, $R^{5B}$ and $R^{6B}$ may be bonded to each other to form a ring, $W_B$ represents —CO— or a divalent aromatic ring group, and $R^{7B}$ represents a hydrogen atom, a methyl group, or a trifluoromethyl group.

[6] The actinic ray-sensitive or radiation-sensitive resin composition as described in any one of [1] to [5], which does not contain a photoacid generator that generates an acid having a pKa of less than −1.40 upon irradiation with actinic rays or radiation.

[7] An actinic ray-sensitive or radiation-sensitive film formed using the actinic ray-sensitive or radiation-sensitive resin composition as described in any one of [1] to [6].

[8] A pattern forming method comprising: a step of forming an actinic ray-sensitive or radiation-sensitive film using the actinic ray-sensitive or radiation-sensitive resin composition as described in any one of [1] to [6]; a step of irradiating the actinic ray-sensitive or radiation-sensitive film with actinic rays or radiation; and a step of developing the actinic ray-sensitive or radiation-sensitive film irradiated with actinic rays or radiation.

[9] A method for manufacturing an electronic device, comprising the pattern forming method as described in [8].

[10] A photoacid generator generating a sulfonic acid upon irradiation with actinic rays or radiation, represented by any one of General Formula (a), (b) and (1) to (V);

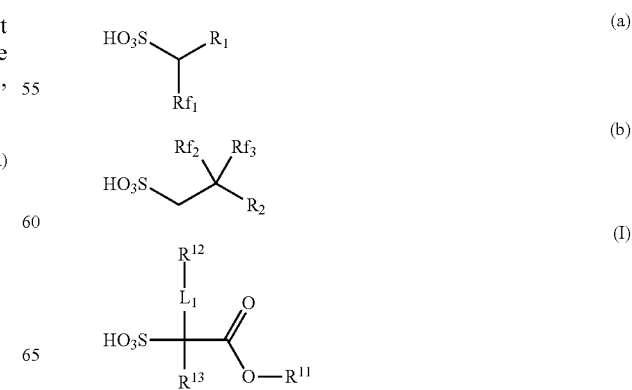

(a)

(b)

(I)

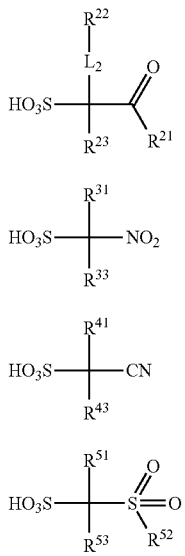

in General Formula (a), $Rf_1$ represents a fluorine atom or an alkyl group containing a fluorine atom, and $R_1$ represents a monovalent organic group, in General Formula (b), $Rf_2$ and $Rf_3$ each independently represent a fluorine atom or an alkyl group containing a fluorine atom, and $R_2$ represents a monovalent organic group, in General Formula (I), $R^{11}$ and $R^{12}$ each independently represent a monovalent organic group, $R^{13}$ represents a hydrogen atom or a monovalent organic group, $L_1$ represents a group represented by —CO—O—, —CO—, —O—, —S—, —O—CO—, —S—CO—, or —CO—S—, and two of $R^{11}$, $R^{12}$, and $R^{13}$ may be bonded to each other to form a ring, in General Formula (II), $R^{21}$ and $R^{22}$ each independently represent a monovalent organic group, $R^{23}$ represents a hydrogen atom or a monovalent organic group, $L_2$ represents a group represented by —CO—, —O—, —S—, —O—CO—, —S—CO—, or —CO—S—, and two of $R^{21}$, $R^{22}$, and $R^{23}$ may be bonded to each other to form a ring, in General Formula (III), $R^{31}$ and $R^{33}$ each independently represent a hydrogen atom or a monovalent organic group, and $R^{31}$ and $R^{33}$ may be bonded to each other to form a ring, in General Formula (IV), $R^{41}$ and $R^{43}$ each independently represent a hydrogen atom or a monovalent organic group, and $R^{41}$ and $R^{43}$ may be bonded to each other to form a ring, and in General Formula (V), $R^{51}$, $R^{52}$, and $R^{53}$ each independently represent a hydrogen atom or a monovalent organic group, and two of $R^{51}$, $R^{52}$, and $R^{53}$ may be bonded to each other to form a ring.

According to the present invention, it is possible to provide an actinic ray-sensitive or radiation-sensitive resin composition which can provide very excellent roughness performance, exposure latitude, and depth of focus, particularly, in the formation of an ultrafine pattern (for example, a contact hole pattern having a hole diameter of 45 nm or less, or a line-and-space pattern having a line width of 45 nm or less); a photoacid generator; and an actinic ray-sensitive or radiation-sensitive film, a pattern forming method, and a method for manufacturing an electronic device, each using the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

In citations for a group (atomic group) in the present specification, in a case where the group is denoted without specifying whether it is substituted or unsubstituted, the group includes both a group not having a substituent and a group having a substituent. For example, an "alkyl group" which is not denoted about whether it is substituted or unsubstituted includes not only an alkyl group not having a substituent (unsubstituted alkyl group), but also an alkyl group having a substituent (substituted alkyl group).

"Actinic rays" or "radiation" in the present specification means, for example, a bright line spectrum of a mercury lamp, far ultraviolet rays typified by an excimer laser, extreme ultraviolet rays (EUV light), X-rays, electron beams (EB), or the like. In addition, in the present invention, light means actinic rays or radiation.

Furthermore, "exposure" in the present specification includes, unless otherwise specified, not only exposure by a mercury lamp, far ultraviolet rays typified by excimer laser, extreme ultraviolet rays (EUV light), X-rays, or the like, but also writing by particle rays such as electron beams and ion beams.

In the present specification, a numerical range expressed using "to" is used in a meaning encompassing a range that includes the preceding and succeeding numerical values of "to" as the lower limit value and the upper limit value, respectively.

In addition, in the present specification, (meth)acrylate represents acrylate and methacrylate, and (meth)acryl represents acryl and methacryl.

In the present specification, the weight-average molecular weight (Mw), the number-average molecular weight (Mn), and the dispersity (Mw/Mn) of a resin are defined as values in terms of polystyrene by means of gel permeation chromatography (GPC) measurement (solvent: tetrahydrofuran, flow amount (amount of a sample injected): 10 µl, columns: TSK gel Multipore HXL-M (×4) manufactured by Tosoh Corporation, column temperature: 40° C., flow rate: 1.0 mL/min, detector: differential refractive index (RI) detector) using a GPC apparatus (HLC-8120GPC manufactured by Tosoh Corporation).

[Actinic Ray-Sensitive or Radiation-Sensitive Resin Composition]

Next, the actinic ray-sensitive or radiation-sensitive resin composition of an embodiment of the present invention will be described.

As described above, the actinic ray-sensitive or radiation-sensitive resin composition of the embodiment of the present invention contains (A) a photoacid generator (hereinafter simply referred to as a "photoacid generator (A)") that generates an acid exhibiting pka of −1.40 or more upon irradiation with actinic rays or radiation, and (B) a resin in which an Eth sensitivity of a repeating unit containing an acid-decomposable group is 5.64 or less.

The present invention has the following configuration, and therefore, it can provide very excellent roughness performance, exposure latitude, and depth of focus, particularly in the formation of an ultrafine pattern (for example, a contact hole pattern having a hole diameter of 45 nm or less, or a line-and-space pattern having a line width of 45 nm or less).

A reason therefor is not clear, but is presumed to be as follows.

First, it is considered that by setting the pKa of the acid generated from the photoacid generator (A) upon irradiation with actinic rays or radiation to −1.40 or more, acid agglutination due to high acidity of the acid is suppressed. As a result, it is assumed that the acid is more uniformly present in the exposed area of the film.

In addition, the resin (B) described above has a repeating unit containing an acid-decomposable group with an Eth sensitivity of 5.64 or less. Here, the "acid-decomposable group with an Eth sensitivity of 5.64 or less" is an acid-decomposable group exhibiting a property of easily leaving through decomposition by the action of an acid, as described in detail later. Therefore, it is considered that a desired chemical amplification reaction sufficiently proceeds through an acid which has the pKa of −1.40 or more generated in the exposed area of the film but not a strong acid.

It is considered that, by the above action, the roughness performance, the exposure latitude performance, and the depth of focus are to be excellent.

Furthermore, such an effect is hard to confirm, for example, in the formation of a fine pattern such as a line-and-space pattern with a line width of 100 nm. However, the present inventors have conducted extensive studies thereon, and as a result, the effect can be noticeably confirmed in the ultrafine pattern (for example, a contact hole pattern having a hole diameter of 45 nm or less, or a line-and-space pattern having a line width of 45 nm or less). In other words, the present inventors found that using the photoacid generator (A) and the resin (B) in combination is very useful in the formation of the ultrafine pattern.

The actinic ray-sensitive or radiation-sensitive resin composition of the embodiment of the present invention is preferably a resist composition, and may be a negative resist composition or a positive resist composition. Furthermore, the actinic ray-sensitive or radiation-sensitive resin composition may be either a resist composition for organic solvent development or a resist composition for alkali development.

The resist composition of the present invention is typically a chemically amplified resist composition.

Hereinafter, components contained in the actinic ray-sensitive or radiation-sensitive resin composition of the embodiment of the present invention (hereinafter, also referred to as the"composition of the present invention") will be described in detail.

<(A) Photoacid Generator that Generates Acid Exhibiting pKa of −1.40 or More Upon Irradiation with Actinic Rays or Radiation>

In a case where the pKa of an acid generated from the photoacid generator upon irradiation with actinic rays or radiation is less than −1.40, the acid has high acid strength so that acid agglutination easily occurs, and therefore in the formation of the ultrafine pattern, there is a tendency that the roughness performance, the exposure latitude performance, and the depth of focus surfaces are deteriorated.

In addition, the pKa of the acid is preferably 3.00 or less, and with this range, the acid strength of the acid is not extremely lowered, and in the formation of the ultrafine pattern, there is a tendency that the roughness performance, the exposure latitude performance, and the depth of focus are further improved.

The pKa of the acid generated by the photoacid generator (A) upon irradiation with actinic rays or radiation is preferably from −1.40 to 3.00, more preferably from −1.00 to 2.50, and still more preferably from −0.80 to 2.00.

In the present specification, the acid dissociation constant pKa indicates an acid dissociation constant pKa in an aqueous solution, and is described, for example, in Chemical Handbook (II) (Revised 4th Edition, 1993, compiled by the Chemical Society of Japan, Maruzen Company, Ltd.), and a lower value thereof indicates higher acid strength. Specifically, the acid dissociation constant pKa in an aqueous solution can be measured using an infinite-dilution aqueous solution and measuring the acid dissociation constant at 25° C., or a value based on the Hammett substituent constants and the database of publicly known literature data can also be obtained by computation using the following software package 1. All the values of pKa described in the present specification indicate values determined by computation using this software package.

Software package 1: Advanced Chemistry Development (ACD/Labs) Software V 8.14 for Solaris (1994-2007 ACD/Labs).

The photoacid generator (A) is preferably a compound (substantially an ionic compound) not including an aromatic ring in an anionic structure. Since such a photoacid generator (A) has high transparency, particularly to ArF light, light reaches up to a bottom part of the actinic ray-sensitive or radiation-sensitive film even in a case where exposure with ArF light is carried out, and thus, the effect of the present invention tends to be more easily expressed.

The acid having a pKa of −1.40 or more generated by the photoacid generator upon irradiation with actinic rays or radiation is preferably sulfonic acid.

Furthermore, the sulfonic acid is preferably an alkyl sulfonic acid in which one fluorine atom is bonded to a carbon atom at the α-position of the sulfonic acid group. Here, an expression of "one fluorine atom is bonded to a carbon atom at the α-position of the sulfonic acid group" means that two or more fluorine atoms are not bonded to a carbon atom at the α-position of the sulfonic acid group. The alkyl group in the alkyl sulfonic acid may have a substituent, and specific examples of the substituent that may be contained in the monovalent organic group as each of $R_1$, $R_2$, $R^{11}$, $R^{12}$, $R^{21}$, $R^{22}$, $R^{23}$, $R^{33}$, $R^{43}$, and $R^{53}$ in General Formulae (a), (b), and (I) to (V).

The sulfonic acid generated by the photoacid generator (A) upon irradiation with actinic rays or radiation is specifically preferably a sulfonic acid represented by any one of General Formula (a), (b), (I), . . . , or (V).

In other words, the photoacid generator (A) is preferably an acid generator that generates a sulfonic acid represented by any one of General Formula (a), (b) and (I) to (V) upon irradiation with actinic rays or radiation.

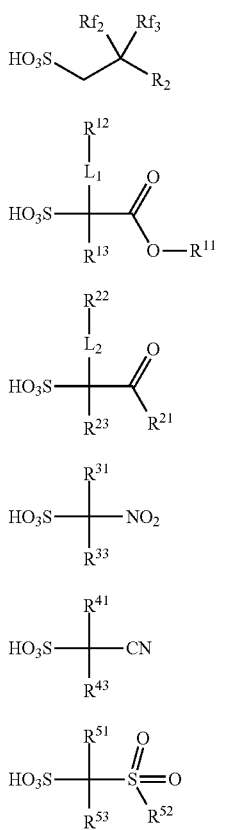

(b), (I), (II), (III), (IV), (V)

In General Formula (a), $Rf_1$ represents a fluorine atom or an alkyl group containing a fluorine atom. $R_1$ represents a monovalent organic group.

In General Formula (b), $Rf_2$ and $Rf_3$ each independently represent a fluorine atom or an alkyl group containing a fluorine atom. $R_2$ represents a monovalent organic group.

In General Formula (I), $R^{11}$ and $R^{12}$ each independently represent a monovalent organic group. $R^{13}$ represents a hydrogen atom or a monovalent organic group. $L_1$ represents a group represented by —CO—O—, —CO—, —O—, —S—, —O—CO—, —S—CO—, or —CO—S—. Two of $R^{11}$, $R^{12}$ and $R^{13}$ may be bonded to each other to form a ring.

In General Formula (I), $R^{21}$ and $R^{22}$ each independently represent a monovalent organic group. $R^{23}$ represents a hydrogen atom or a monovalent organic group. $L_2$ represents a group represented by —CO—, —O—, —S—, —O—CO—, —S—CO—, or —CO—S—. Two of $R^{21}$, $R^{22}$ and $R^{23}$ may be bonded to each other to form a ring.

The bonding arm on the left side to the divalent linking group as each of $L_1$ and $L_2$ is bonded to the carbon atom to which a sulfonic acid group (—$SO_3H$) is bonded, and the bonding arm on the right side to the divalent linking group is bonded to $R^{12}$ and $R^{22}$.

In General Formula (III), $R^{31}$ and $R^{33}$ each independently represent a hydrogen atom or a monovalent organic group. $R^{31}$ and $R^{33}$ may be bonded to each other to form a ring.

In General Formula (IV), $R^{41}$ and $R^{43}$ each independently represent a hydrogen atom or a monovalent organic group. $R^{41}$ and $R^{43}$ may be bonded to each other to form a ring.

In General Formula (V), $R^{51}$, $R^{52}$ and $R^{53}$ each independently represent a hydrogen atom or a monovalent organic group. Two of $R^{51}$, $R^{52}$ and $R^{53}$ may be bonded to each other to form a ring.

The monovalent organic group as each of General Formulae (a) and (b) preferably has 1 to 30 carbon atoms, more preferably has 1 to 20 carbon atoms, and still more preferably has 1 to 10 carbon atoms, and examples thereof include an alkyl group, a cycloalkyl group, an alkyloxycarbonyl group, and a cycloalkyloxycarbonyl group. These groups may further have a substituent.

The monovalent organic group as each of $R_1$, $R_2$, $R^{11}$, $R^{12}$, $R^{21}$, $R^{22}$, $R^{23}$, $R^{31}$, $R^{33}$, $R^{41}$, $R^{43}$, $R^{51}$, $R^{52}$, and $R^{53}$ in General Formulae (a), (b), and (I) to (V) preferably has 1 to 30 carbon atoms, more preferably has 1 to 20 carbon atoms, still more preferably has 1 to 10 carbon atoms, and examples thereof include an alkyl group, a cycloalkyl group, an aryl group, an aralkyl group, and an alkenyl group. These groups may further have a substituent.

The substituent may be any one of a halogen atom, an alkyl group (which may be linear or branched and preferably has 1 to 12 carbon atoms), a cycloalkyl group (which may be any one of a monocycle, a polycycle, or a spiro ring, and preferably has 3 to 20 carbon atoms), an aryl group (preferably having 6 to 14 carbon atoms), a hydroxy group, a carbonyl group, an ether group, a cyano group, an alkoxy group, an ester group, an amido group, a urethane group, a ureido group, a thioether group, a sulfonamido group, a sulfonic acid ester group, and a group formed by combination of two or more selected from these atoms and groups.

The alkyl group containing a fluorine atom as each of $Rf_1$, $Rf_2$, and $Rf_3$ in General Formulae (a) and (b) represents an alkyl group in which at least one hydrogen atom is substituted with a fluorine atom, and the alkyl group preferably has 1 to 6 carbon atoms, and more preferably 1 to 3 carbon atoms.

Furthermore, the alkyl group containing a fluorine atom is preferably a perfluoroalkyl group, and more preferably a trifluoromethyl group.

Specific examples of the sulfonic acid generated by the photoacid generator (A) upon irradiation with actinic rays or radiation are shown below, but the present invention is not limited thereto.

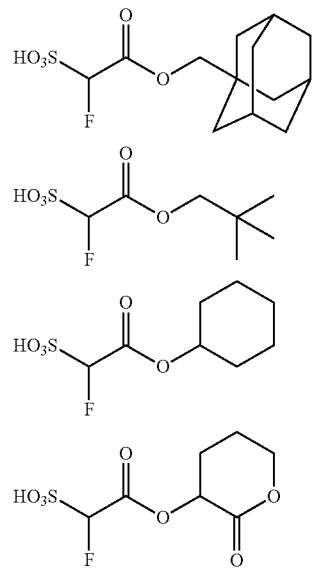

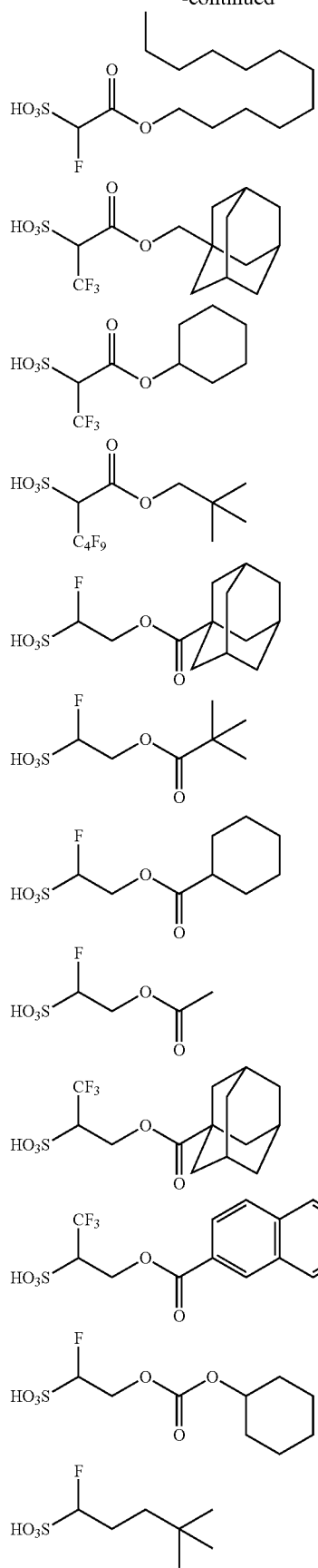
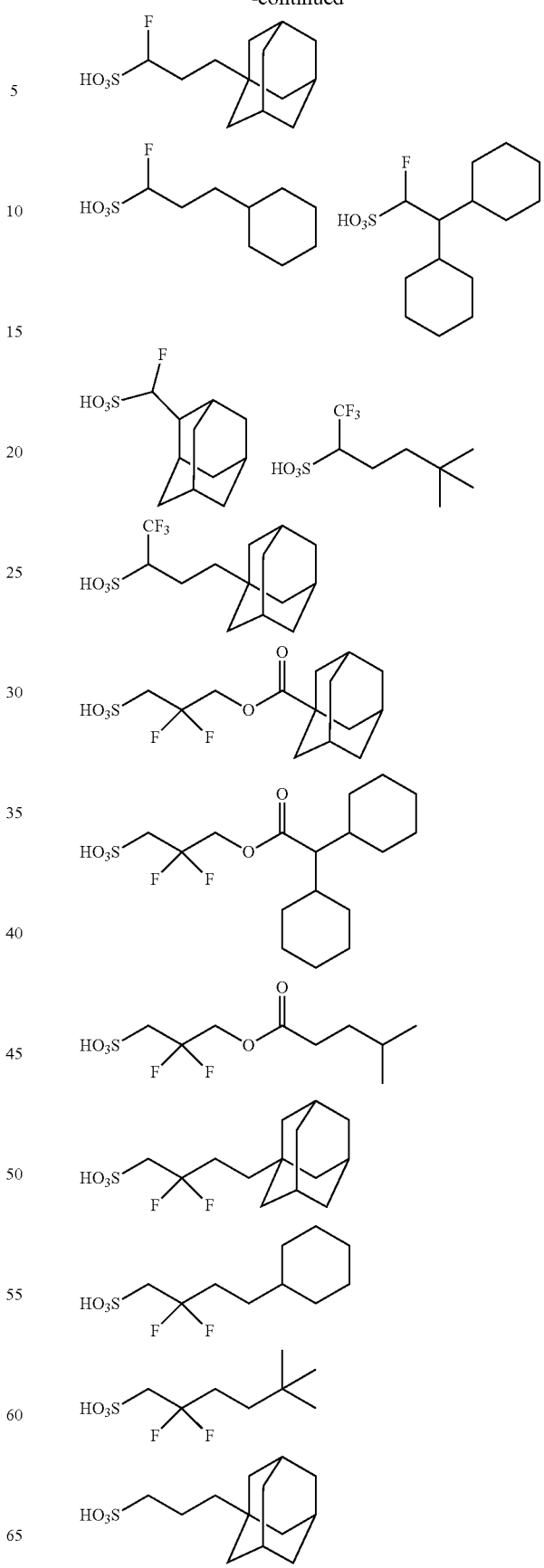

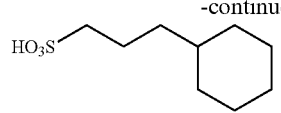
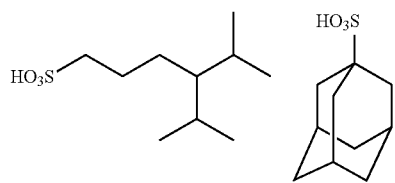
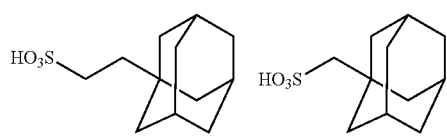
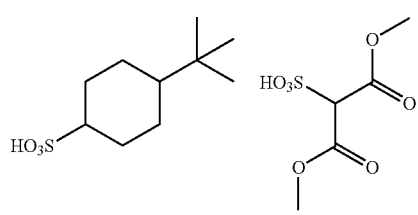
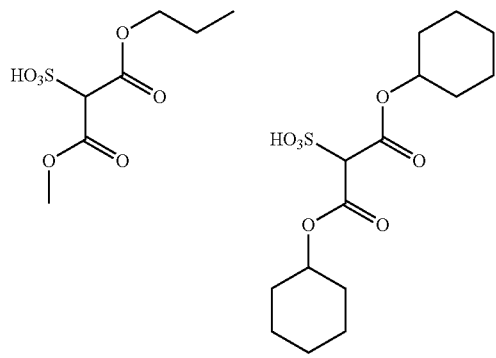
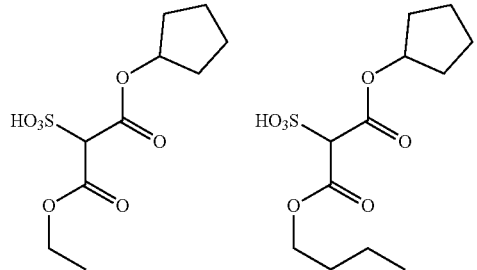
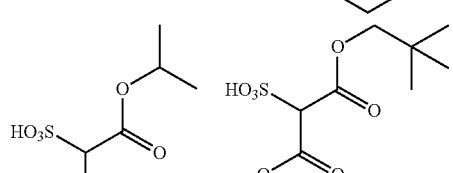
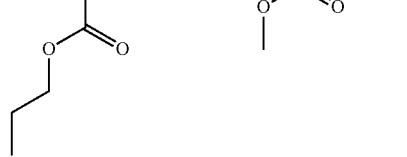
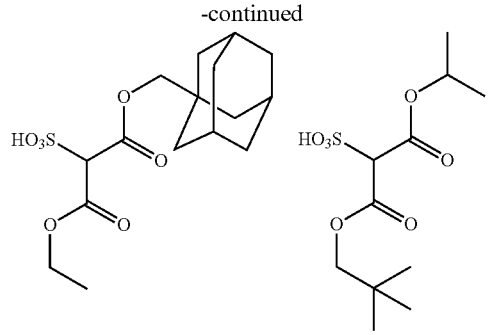
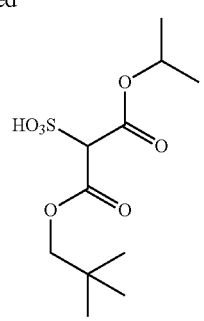
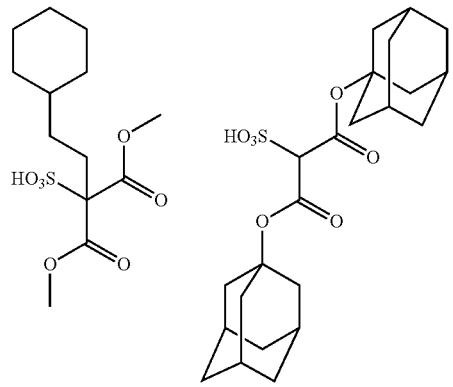
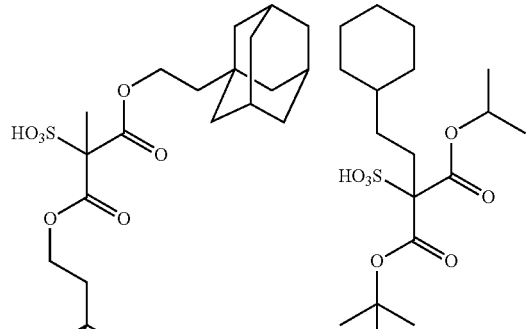
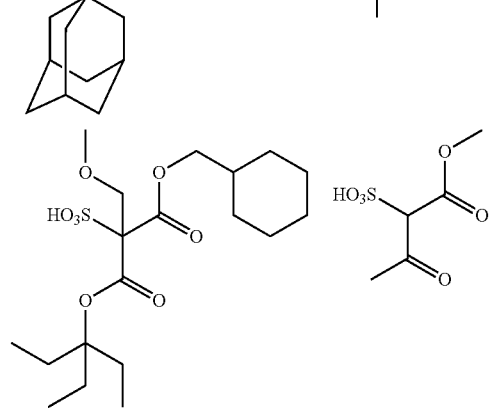
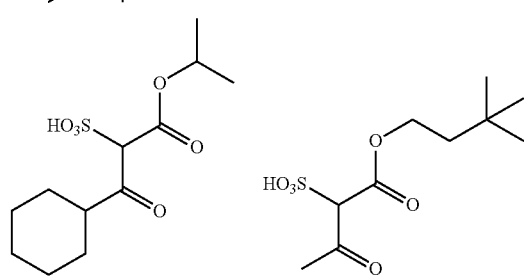

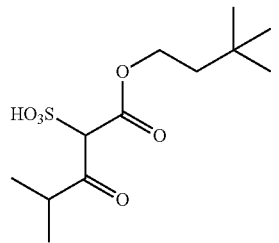
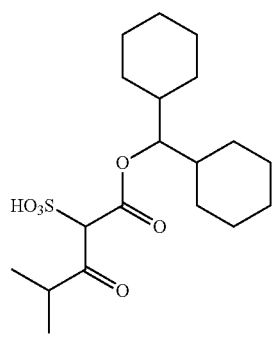
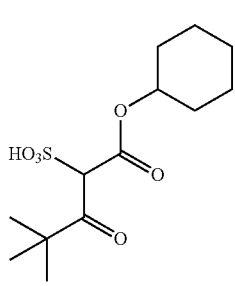
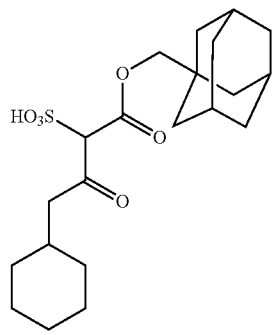
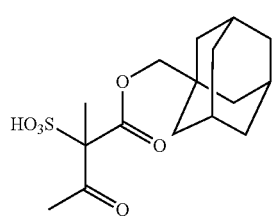
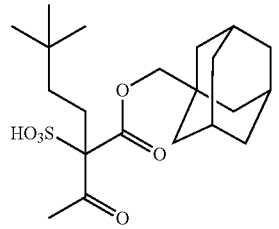
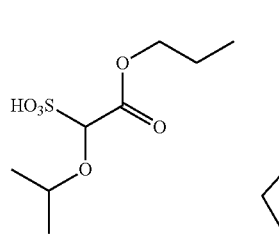
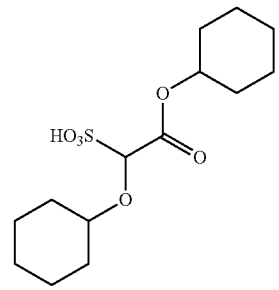
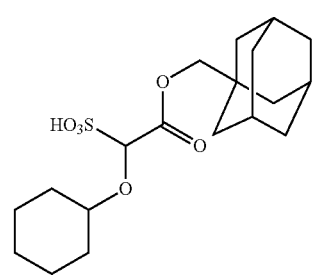
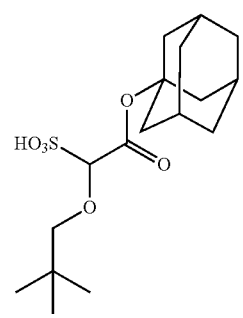
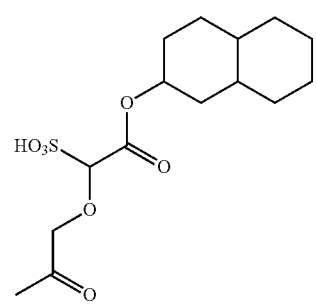
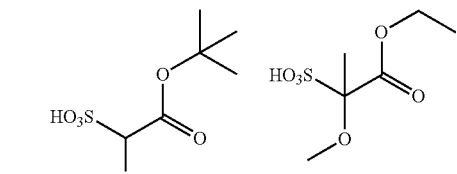
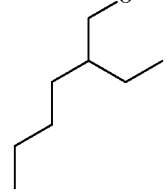

-continued
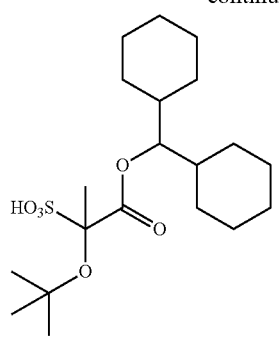
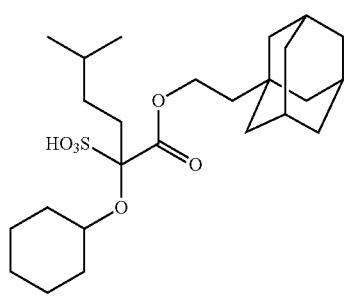
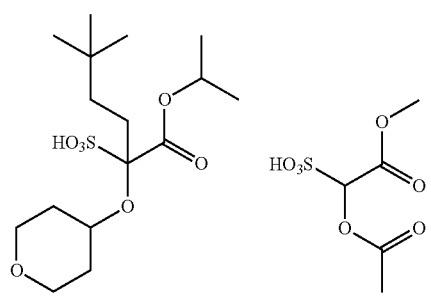
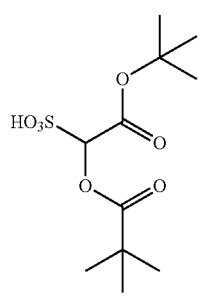
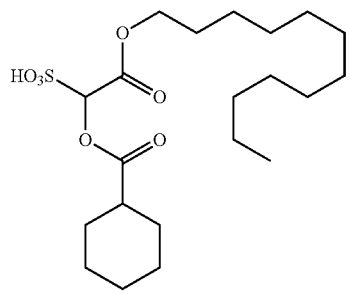
-continued
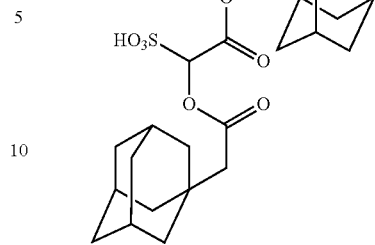
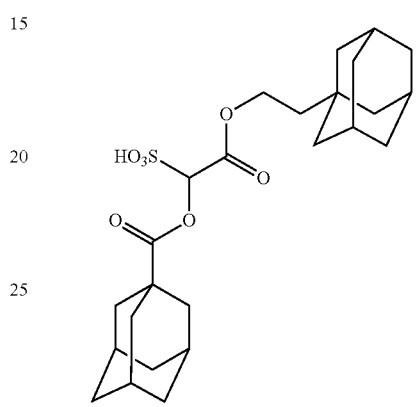
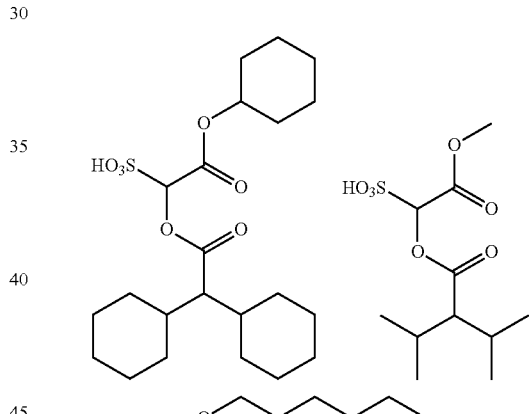
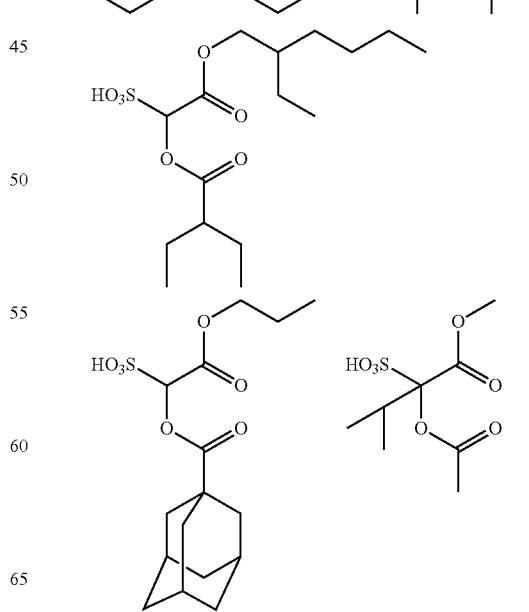

-continued
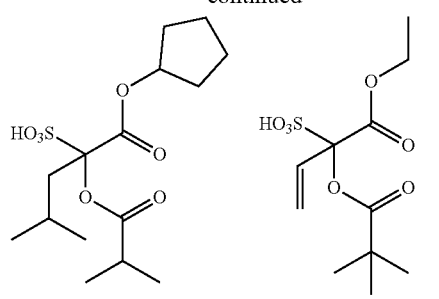
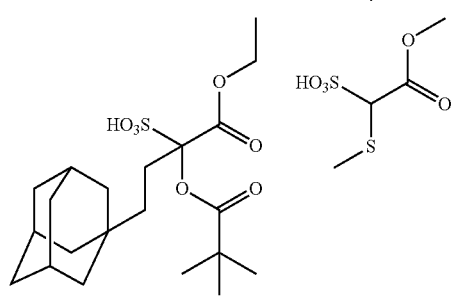
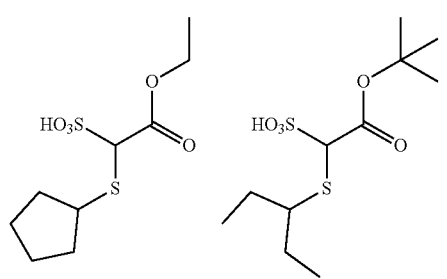
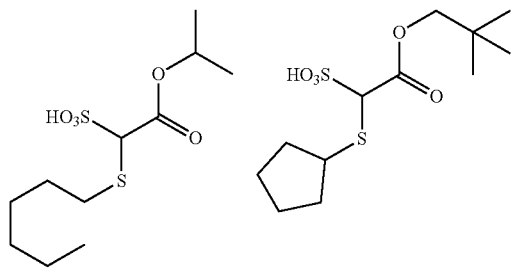
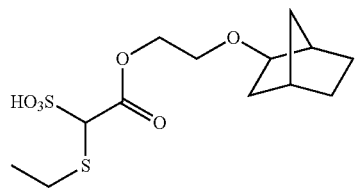
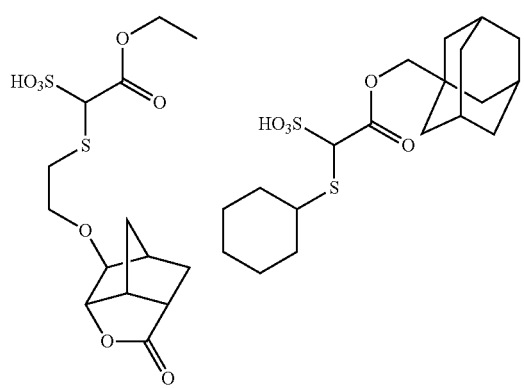
-continued
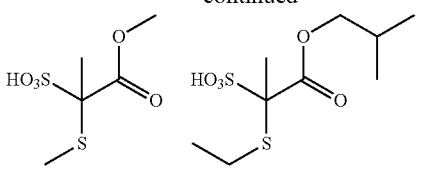
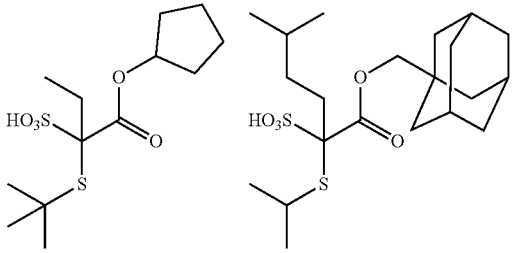
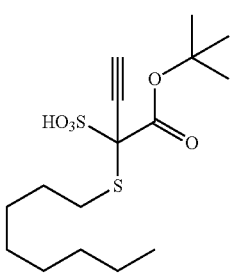
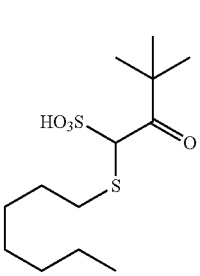
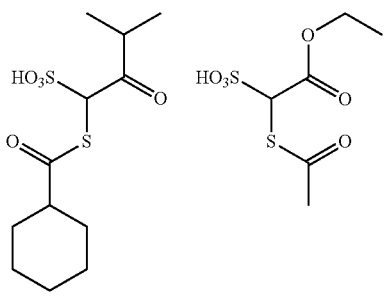
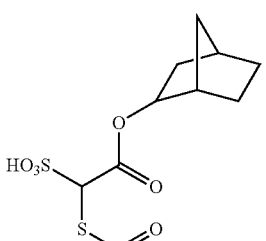
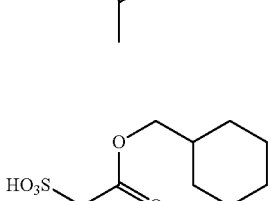
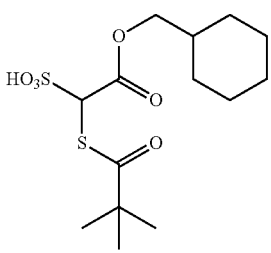

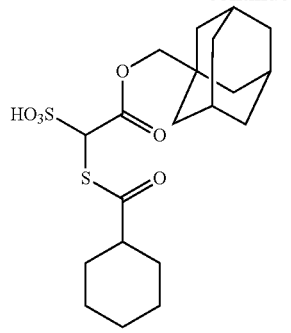
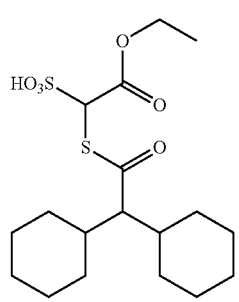
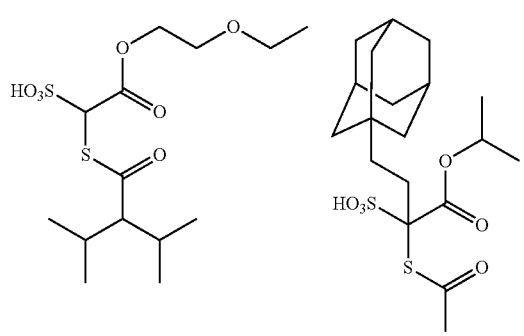
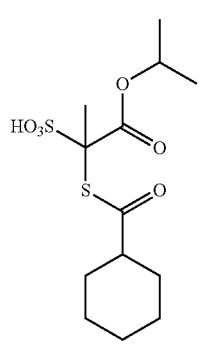
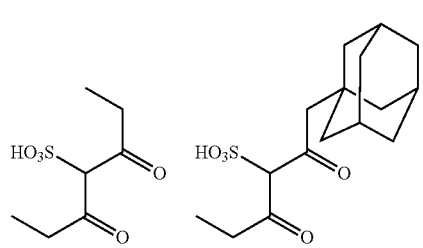
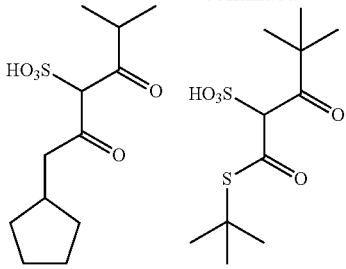
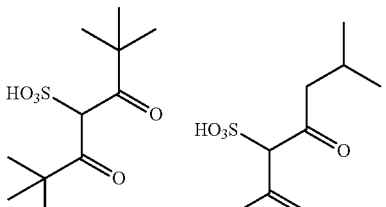
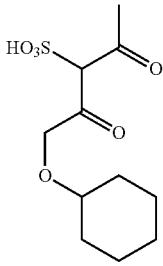
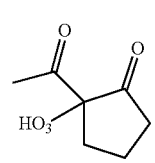
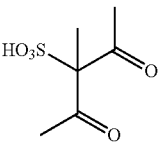
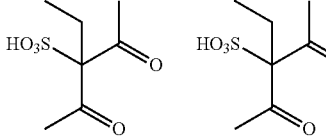
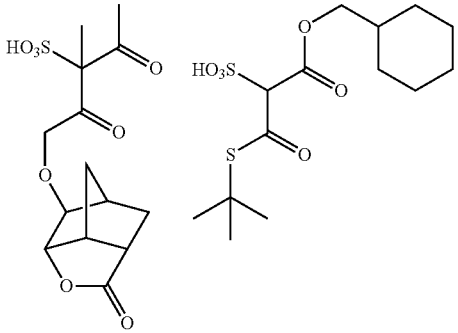
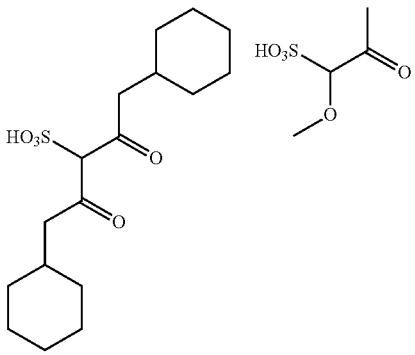

-continued
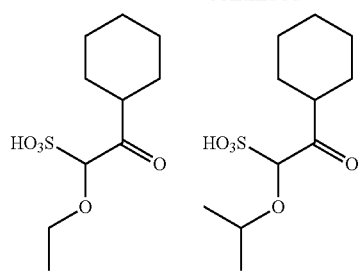
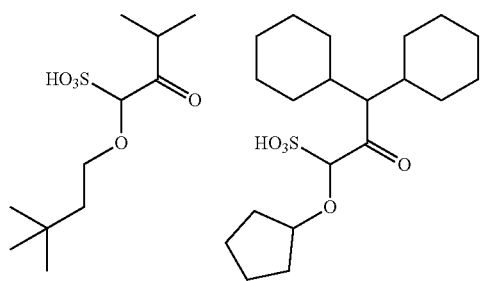
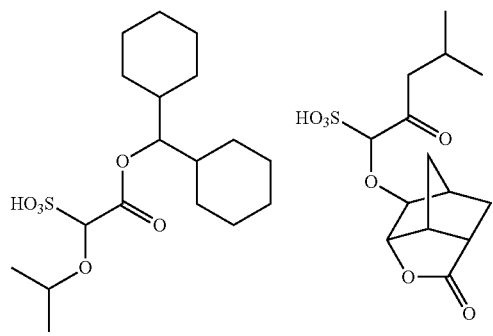
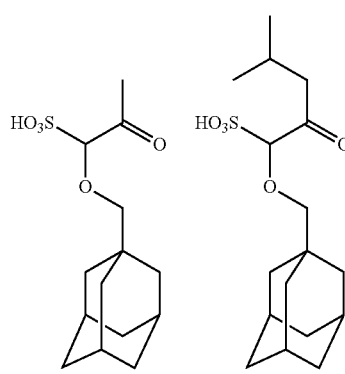
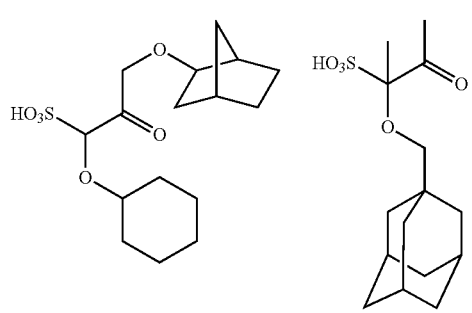
-continued
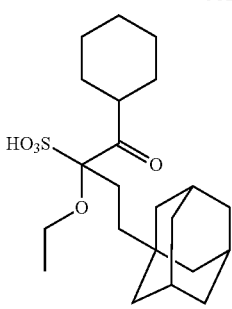
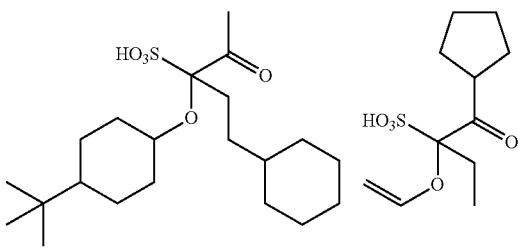
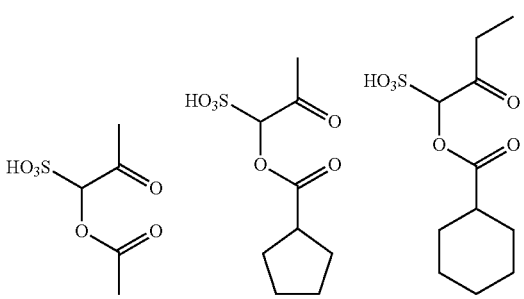
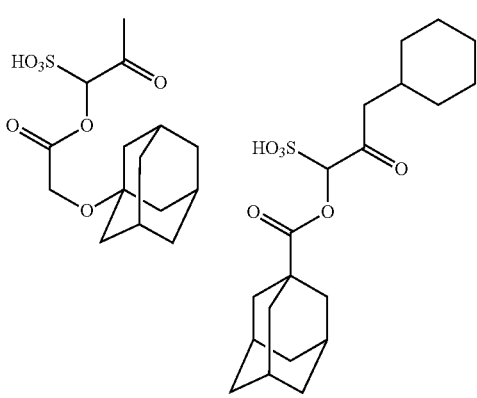
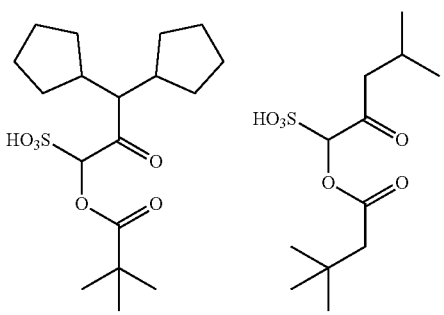

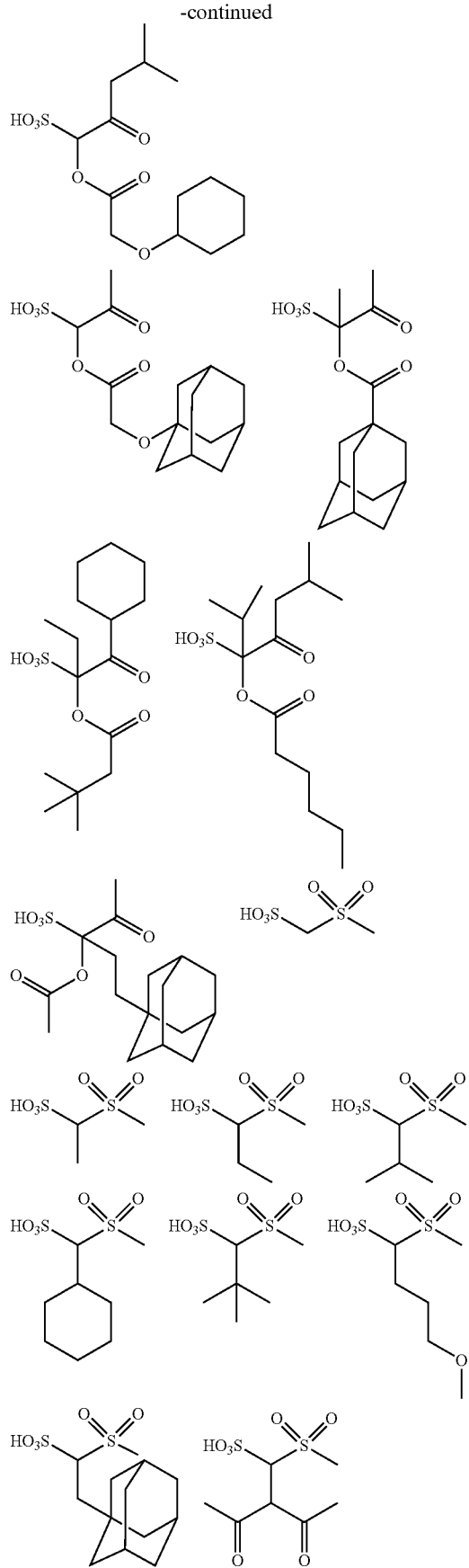
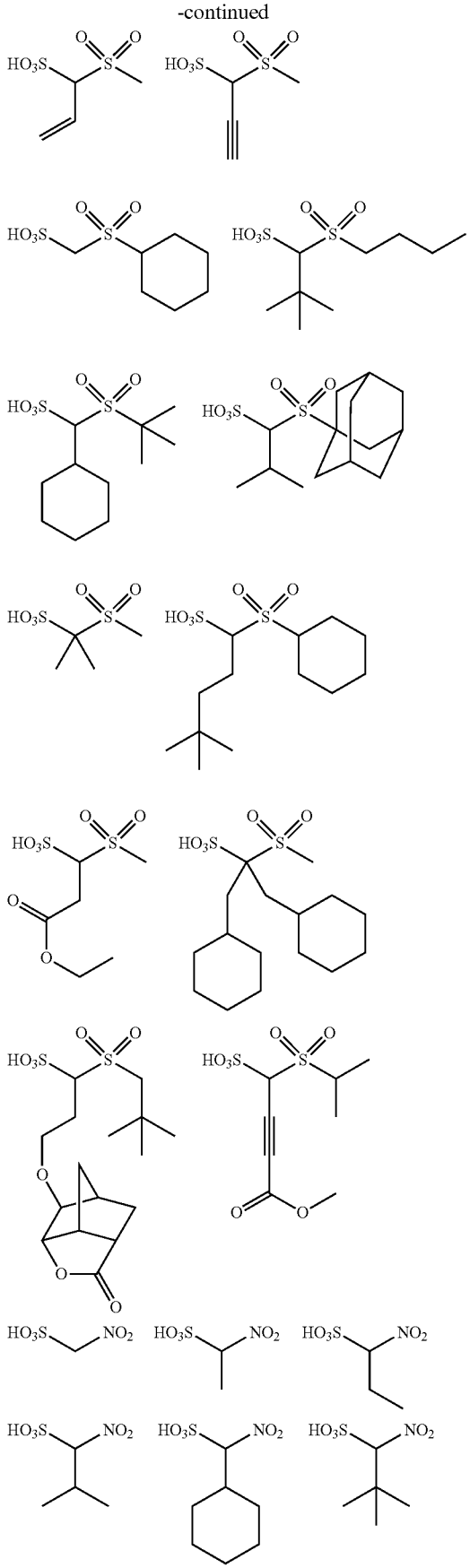

-continued

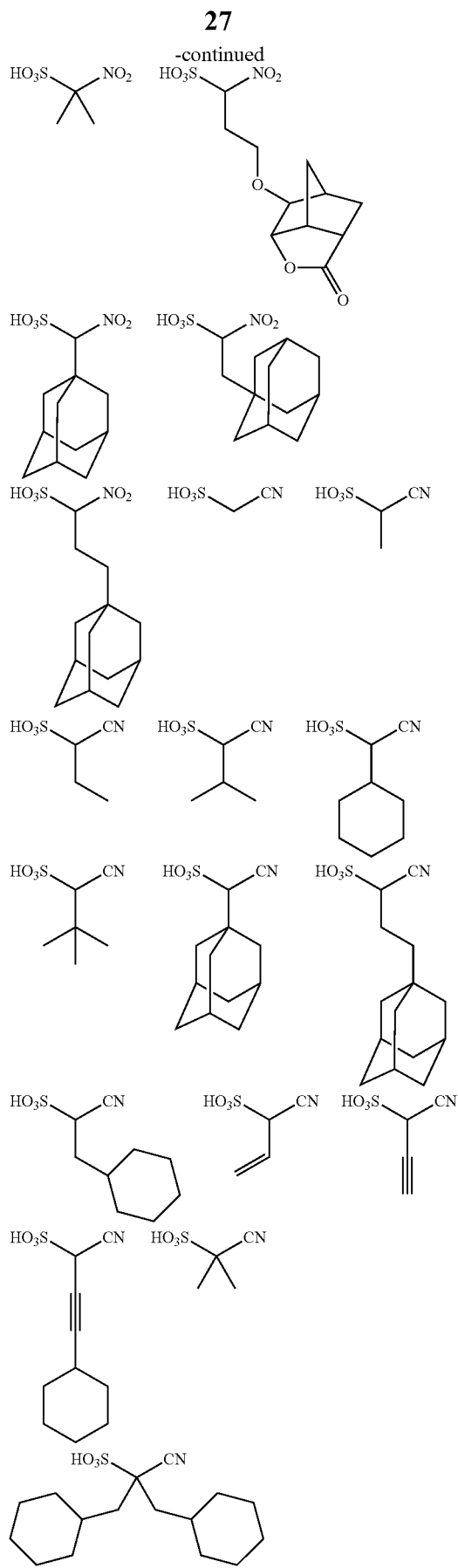

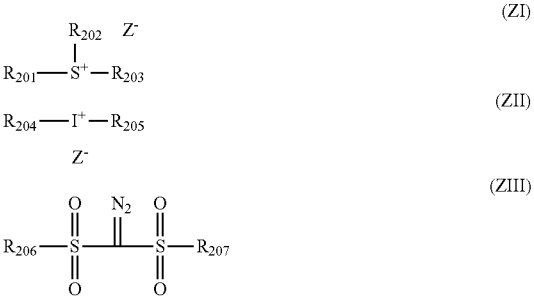

The photoacid generator (A) of the present invention is preferably a compound represented by General Formula (A).

$$X'^{\oplus} \ ^{\ominus}Y$$ (A)

In General Formula (A), $Y^-$ represents a sulfonate anion corresponding to the sulfonic acid represented by any one of General Formula (a), (b) and (1) to (V).

X' represents a cation.

The cation as X' is not particularly limited, but suitable examples of aspects thereof include a cation (part other than $Z^-$) in General Formula (ZI), (ZII), or (ZIII) which will be described later.

$$R_{201}\overset{\underset{\displaystyle R_{202}}{|}}{\underset{}{S^+}}\text{—}R_{203} \quad Z^-$$ (ZI)

$$R_{204}\text{—}I^+\text{—}R_{205}$$ (ZII)

$$Z^-$$

$$R_{206}\overset{\underset{\displaystyle O}{\|}}{\underset{\underset{\displaystyle O}{\|}}{S}}\text{—}\overset{N_2}{C}\text{—}\overset{\underset{\displaystyle O}{\|}}{\underset{\underset{\displaystyle O}{\|}}{S}}\text{—}R_{207}$$ (ZIII)

In General Formula (ZI), $R_{201}$, $R_{202}$, and $R_{203}$ each independently represent an organic group.

The number of carbon atoms of the organic group as $R_{201}$, $R_{202}$, and $R_{203}$ is generally 1 to 30, and preferably 1 to 20.

Two of $R_{201}$ to $R_{203}$ may be bonded to each other to form a ring structure, and the ring may contain an oxygen atom, a sulfur atom, an ester bond, an amide bond, or a carbonyl group. Examples of the group formed by bonding of two of $R_{201}$ to $R_{203}$ include an alkylene group (for example, a butylene group and a pentylene group).

$Z^-$ represents a sulfonate anion corresponding to the sulfonic acid represented by any one of General Formula (a), (b) and (1) to (V).

Examples of the organic group represented by $R_{201}$, $R_{202}$, and $R_{203}$ include corresponding groups in the compounds (ZI-1), (ZI-2), (ZI-3), and (ZI-4) which will be described later.

Incidentally, the compound may be a compound having a plurality of structures represented by General Formula (ZI). For example, the compound may be a compound having a structure in which at least one of $R_{201}, \ldots,$ or $R_{203}$ in a compound represented by General Formula (ZI) is bonded to at least one of $R_{201}, \ldots,$ or $R_{203}$ in another compound represented by General Formula (ZI) through a single bond or a linking group.

More preferred examples of the components (ZI) include the compounds (ZI-1), (ZI-2), (ZI-3), and (ZI-4) which will be described below.

First, the compound (ZI-1) will be described.

The compound (ZI-1) is an arylsulfonium compound in which at least one of $R_{201}, \ldots,$ or $R_{203}$ in General Formula (ZI) is an aryl group, that is, a compound having arylsulfonium as the cation.

In the arylsulfonium compound, all of $R_{201}$ to $Rc_{203}$ may be an aryl group, or a part of $R_{201}$ to $R_{203}$ may be an aryl group, with the remainder being an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound, and an aryldicycloalkylsulfonium compound.

The aryl group in the arylsulfonium compound is preferably a phenyl group or a naphthyl group, and more preferably a phenyl group. The aryl group may be an aryl group having a heterocyclic structure containing an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium compound has two or more aryl groups, these two or more aryl groups may be the same as or different from each other.

The alkyl group or the cycloalkyl group which may be contained, if desired, in the arylsulfonium compound, is preferably a linear or branched alkyl group having 1 to 15 carbon atoms or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of $R_{201}$ to $R_{203}$ may have, as the substituent, an alkyl group (for example, an alkyl group having 1 to 15 carbon atoms), a cycloalkyl group (for example, a cycloalkyl group having 3 to 15 carbon atoms), an aryl group (for example, an aryl group having 6 to 14 carbon atoms), an alkoxy group (for example, an alkoxy group having 1 to 15 carbon atoms), a halogen atom, a hydroxyl group, or a phenylthio group.

Next, the compound (ZI-2) will be described.

The compound (ZI-2) is a compound in which $R_{201}$ to $R_{203}$ in Formula (ZI) each independently represent an organic group not having an aromatic ring. The aromatic ring as used herein encompasses an aromatic ring containing a heteroatom.

The organic group not having an aromatic ring as each of $R_{201}$ to $R_{203}$ has generally 1 to 30 carbon atoms, and preferably 1 to 20 carbon atoms.

$R_{201}$ to $R_{203}$ are each independently preferably an alkyl group, a cycloalkyl group, an allyl group, or a vinyl group, more preferably a linear or branched 2-oxyalkyl group, a 2-oxocycloalkyl group, or an alkoxycarbonylmethyl group, and still more preferably a linear or branched 2-oxyalkyl group.

As the alkyl group and the cycloalkyl group of each of $R_{201}$ to $R_{203}$, a linear or branched alkyl group having 1 to 10 carbon atoms (for example, a methyl group, an ethyl group, a propyl group, a butyl group, and a pentyl group), or a cycloalkyl group having 3 to 10 carbon atoms (a cyclopentyl group, a cyclohexyl group, and a norbornyl group) is preferable.

$R_{201}$ to $R_{203}$ may further be substituted with a halogen atom, an alkoxy group (for example, an alkoxy group having 1 to 5 carbon atoms), a hydroxyl group, a cyano group, and a nitro group.

Next, the compound (ZI-3) will be described.

The compound (ZI-3) is a compound represented by General Formula (ZI-3), which has a phenacylsulfonium salt structure.

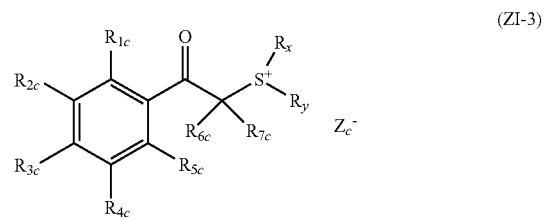

(ZI-3)

In General Formula (ZI-3), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ each independently represent a hydrogen atom, an alkyl group, a cycloalkyl group, a halogen atom, a cyano group, or an aryl group.

$R_x$ and $R_y$ each independently represent an alkyl group, a cycloalkyl group, a 2-oxyalkyl group, a 2-oxocycloalkyl group, an alkoxycarbonylalkyl group, an allyl group, or a vinyl group.

Any two or more of $R_{1c}$ to $R_{5c}$, $R_{5c}$ and $R_{6c}$, $R_{6c}$ and $R_{7c}$, $R_{5c}$ and $R_x$, or $R_x$ and $R_y$ may be respectively bonded to each other to form a ring structure, and this ring structure may contain an oxygen atom, a sulfur atom, a ketone group, an ester bond, or an amide bond.

Examples of the ring structure include an aromatic or non-aromatic hydrocarbon ring, an aromatic or non-aromatic heterocyclic ring, and a polycyclic fused ring formed by combination of two or more of these rings. Examples of the ring structure include 3- to 10-membered rings, with 4- to 8-membered rings being preferable, and 5- or 6-membered rings being more preferable.

Examples of the group formed by the mutual bonding of any two or more of $R_{1c}$ to $R_{5c}$, $R_{6c}$ and $R_{7c}$, or $R_x$ and $R_y$ include a butylene group, and a pentylene group.

The group formed by the mutual bonding of $R_{5c}$ and $R_{6c}$, or $R_{5c}$ and $R_x$ is preferably a single bond or an alkylene group, and examples of the alkylene group include a methylene group and an ethylene group.

$Zc^-$ represents a sulfonate anion corresponding to the sulfonic acid represented by any one of General Formula (a), (b) and (1) to (V).

Specific examples of the alkoxy group in the alkoxycarbonyl group as each of $R_{1c}$ to $R_{5c}$ are the same as the specific examples of the alkoxy group as each of $R_{1c}$ to $R_{5c}$.

Specific examples of the alkyl group in the alkylcarbonyloxy group and the alkylthio group as each of $R_{1c}$ to $R_{5c}$ are the same as the specific examples of the alkyl group as each of $R_{1c}$ to $R_{5c}$.

Specific examples of the cycloalkyl group in the cycloalkylcarbonyloxy group as each of $R_{1c}$ to $R_{5c}$ are the same as the specific examples of the cycloalkyl group as each of $R_{1c}$ to $R_{5c}$.

Specific examples of the aryl group in the aryloxy group and the arylthio group as each of $R_{1c}$ to $R_{5c}$ are the same as the specific examples of the aryl group as each of $R_{1c}$ to $R_{5c}$.

Examples of the cation in the compound (ZI-2) or (ZI-3) in the present invention include the cations described after paragraph [0036] of US2012/0076996A.

Next, the compound (ZI-4) will be described.

The compound (ZI-4) is represented by General Formula (ZI-4).

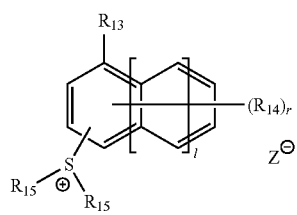

(ZI-4)

In General Formula (ZI-4), $R_{13}$ represents a hydrogen atom, a fluorine atom, a hydroxyl group, an alkyl group, a cycloalkyl group, an alkoxy group, an alkoxycarbonyl group, or a group having a cycloalkyl group, and these groups may have a substituent.

In a case where $R_{14}$'s are present in plural numbers, they each independently represent a hydroxyl group, an alkyl group, a cycloalkyl group, an alkoxy group, an alkoxycarbonyl group, an alkylcarbonyl group, an alkylsulfonyl group, a cycloalkylsulfonyl group, or a group having a cycloalkyl group, and these groups may have a substituent.

$R_{15}$'s each independently represent an alkyl group, a cycloalkyl group or a naphthyl group, and these groups may have a substituent. Two $R_{15}$'s each may be bonded to each other to form a ring. In a case where two $R_{15}$'s each are bonded to each other to form a ring, a ring skeleton may contain a heteroatom such as an oxygen atom and a nitrogen atom. In one aspect, it is preferable that two of $R_{15}$'s each are an alkylene group and bonded to each other to form a ring structure.

l represents an integer of 0 to 2, r represents an integer of 0 to 8, and $Z^-$ represents a sulfonate anion corresponding to the sulfonic acid represented by any one of General Formula (a), (b) and (I) to (V).

In General Formula (ZI-4), the alkyl group of each of $R_{13}$, $R_{14}$, and $R_{15}$ is linear or branched, and preferably has 1 to 10 carbon atoms, and preferred examples thereof include a methyl group, an ethyl group, an n-butyl group, and a t-butyl group.

Examples of the cation of the compound represented by General Formula (ZI-4) in the present invention include the cations described in paragraphs [0121], [0123], and [0124] of JP2010-256842A, paragraphs [0127], [0129], and [0130] of JP2011-076056A, and the like.

Next, General Formulae (ZII) and (ZIII) will be described.

In General Formulae (ZII) and (ZIII), $R_{204}$ to $R_{207}$ each independently represent an aryl group, an alkyl group, or a cycloalkyl group.

The aryl group of $R_{204}$ to $R_{207}$ is preferably a phenyl group or a naphthyl group, and more preferably a phenyl group. The aryl group of $R_{204}$ to $R_{207}$ may be an aryl group having a heterocyclic structure containing an oxygen atom, a nitrogen atom, a sulfur atom, or the like. Examples of the skeleton of the aryl group having a heterocyclic structure include pyrrole, furan, thiophene, indole, benzofuran, and benzothiophene.

Preferred examples of the alkyl group and the cycloalkyl group with respect to $R_{204}$ to $R_{207}$ include a linear or branched alkyl group having 1 to 10 carbon atoms (for example, a methyl group, an ethyl group, a propyl group, a butyl group, and a pentyl group) and a cycloalkyl group having 3 to 10 carbon atoms (for example, a cyclopentyl group, a cyclohexyl group, and a norbornyl group).

The aryl group, the alkyl group, and the cycloalkyl group of $R_{204}$ to $R_{207}$ may have a substituent. Examples of the substituent which may be contained in the aryl group, the alkyl group, and the cycloalkyl group of each of $R_{204}$ to $R_{207}$ include an alkyl group (for example, an alkyl group having 1 to 15 carbon atoms), a cycloalkyl group (for example, a cycloalkyl group having 3 to 15 carbon atoms), an aryl group (for example, an aryl group having 6 to 15 carbon atoms), an alkoxy group (for example, an alkoxy group having 1 to 15 carbon atoms), a halogen atom, a hydroxyl group, and a phenylthio group.

$Z^-$ represents a sulfonate anion corresponding to the sulfonic acid represented by any one of General Formula (a), (b) and (I) to (V).

Specific examples of the photoacid generator (A) of the present invention are shown below, but the present invention is not limited thereto.

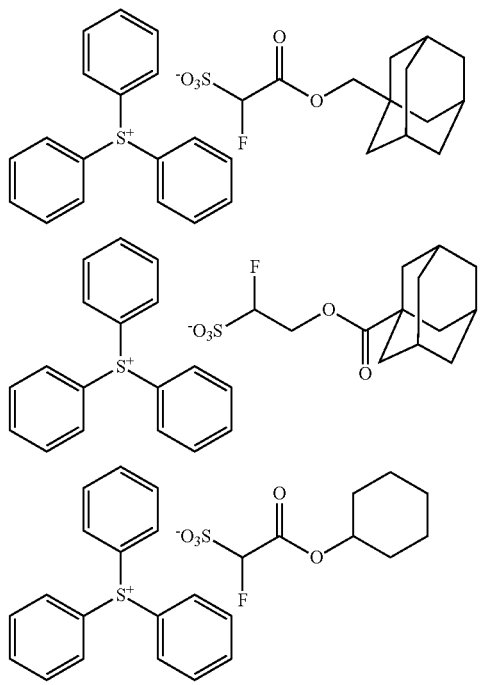

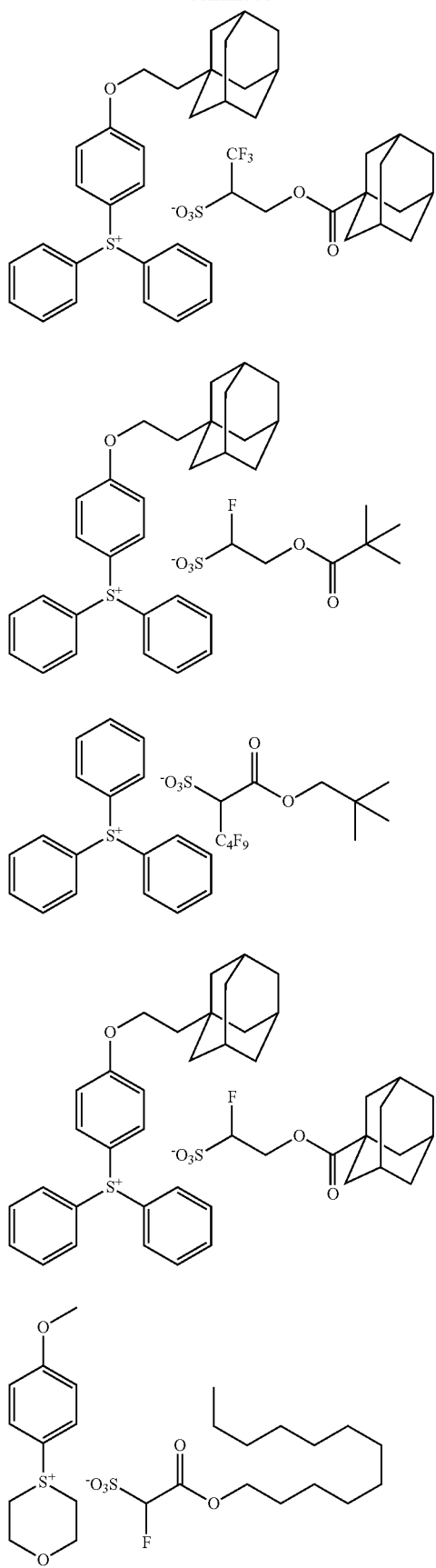
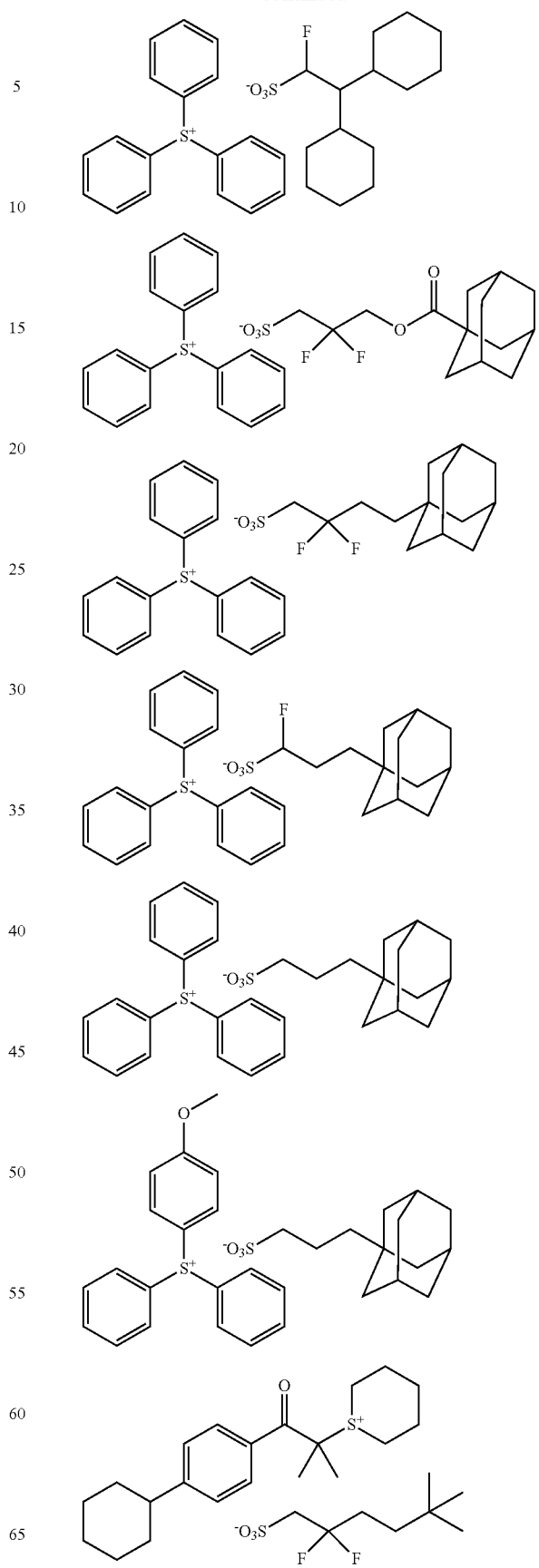

35
-continued
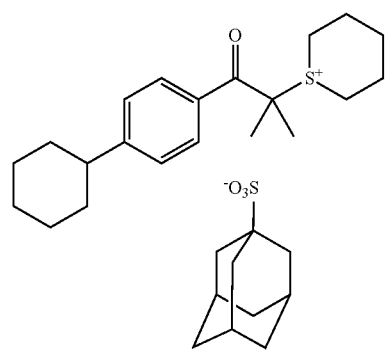
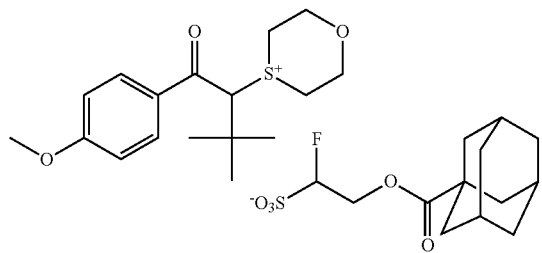
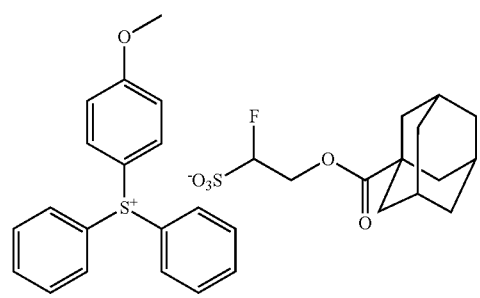
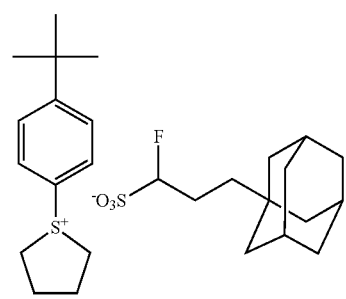
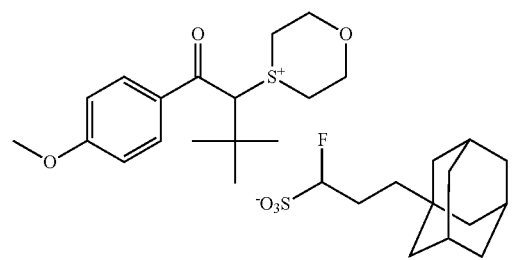
36
-continued
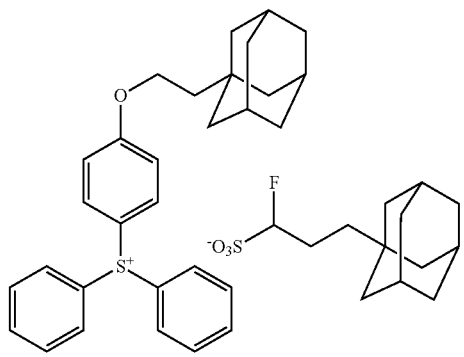
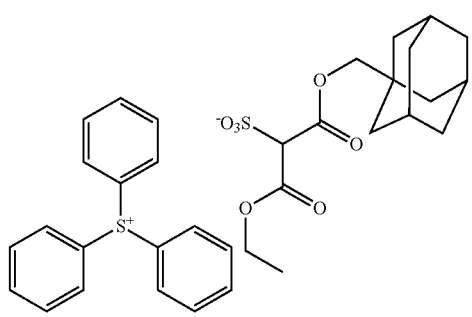
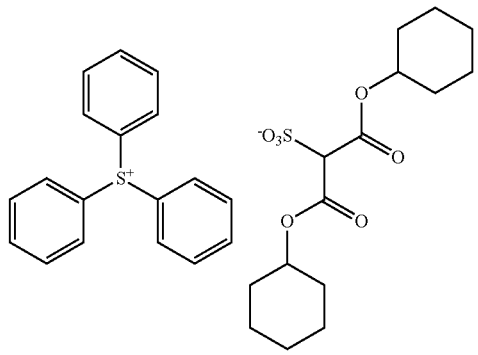
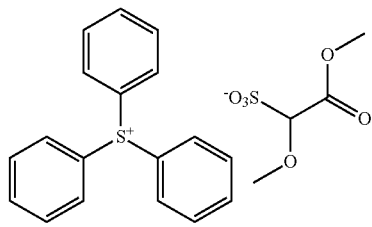
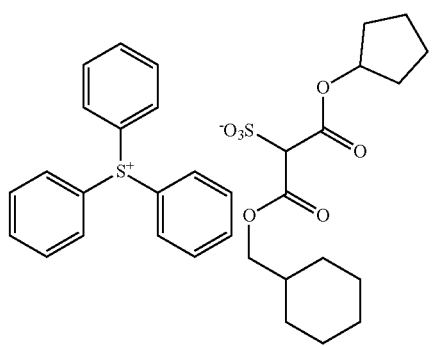

37
-continued
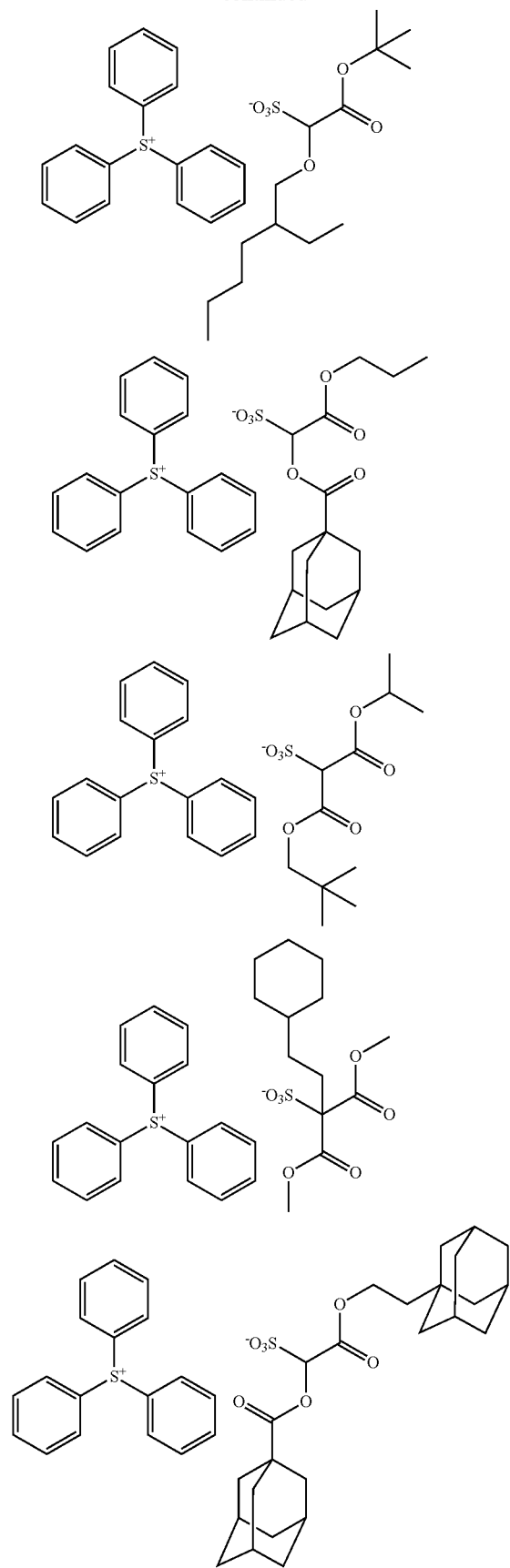
38
-continued
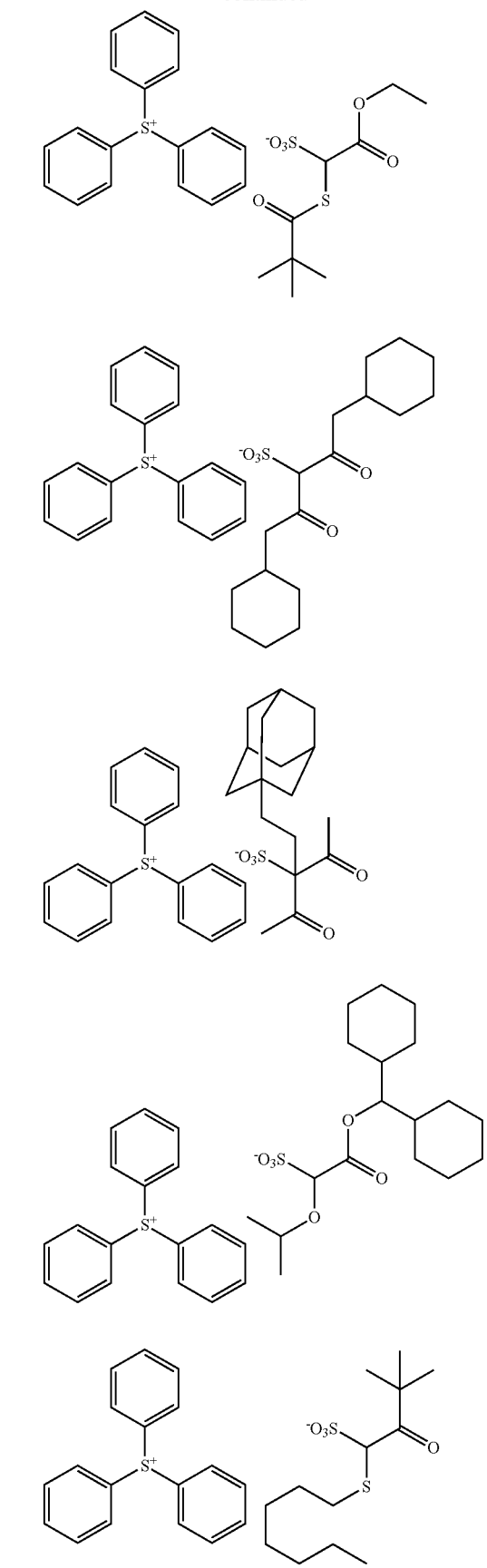

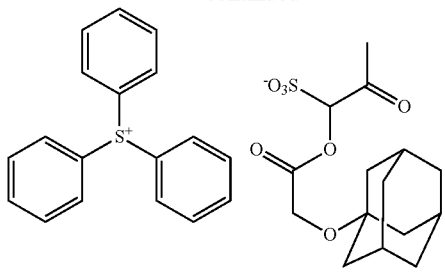
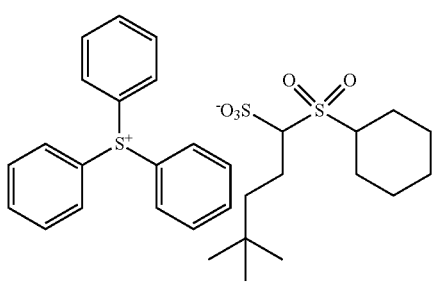
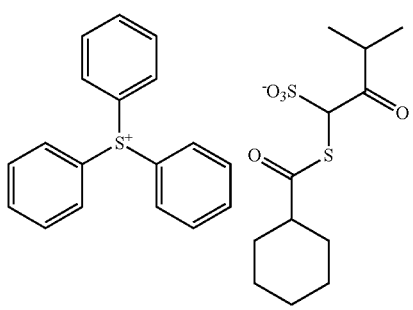
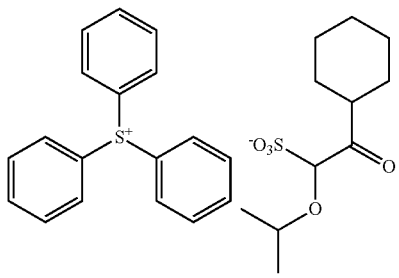
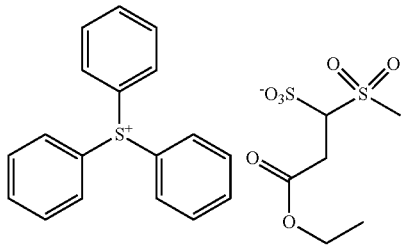
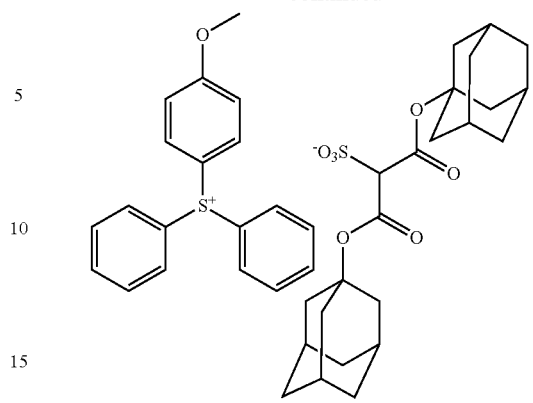
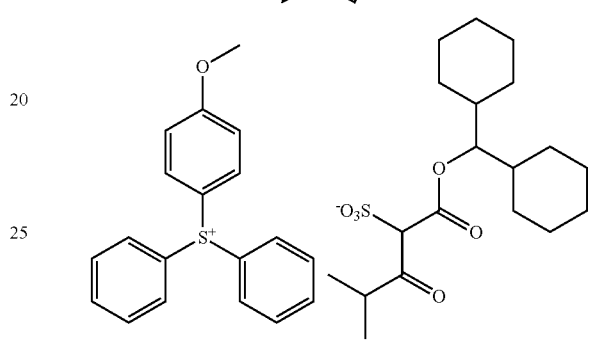
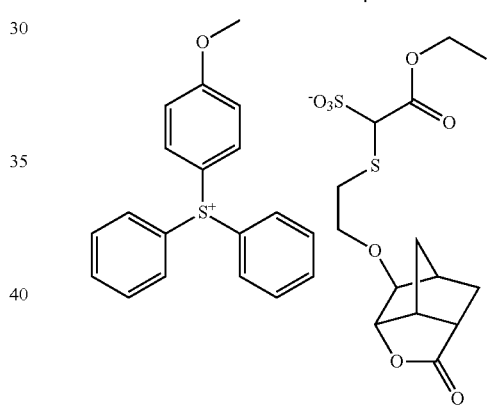
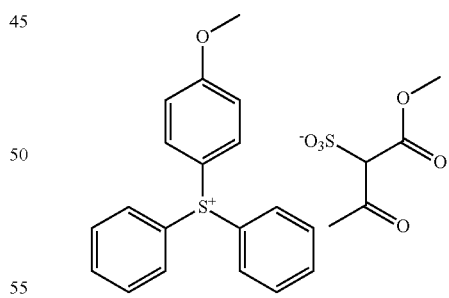
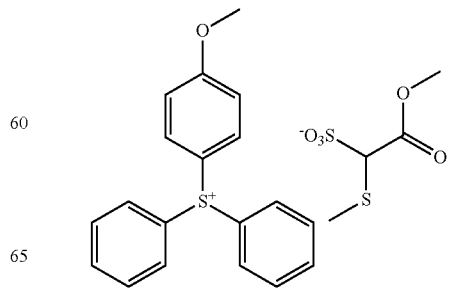

41
-continued
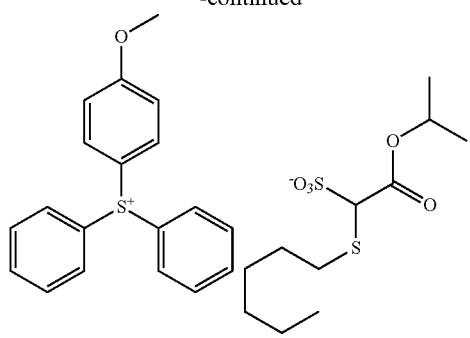
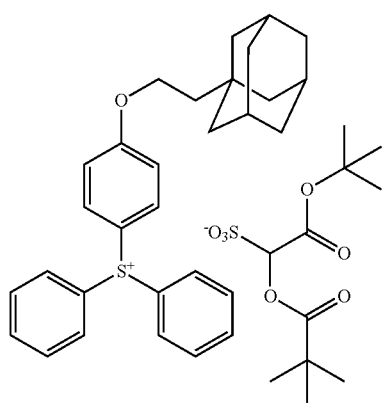
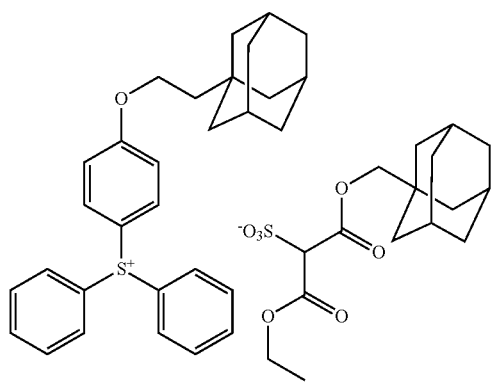
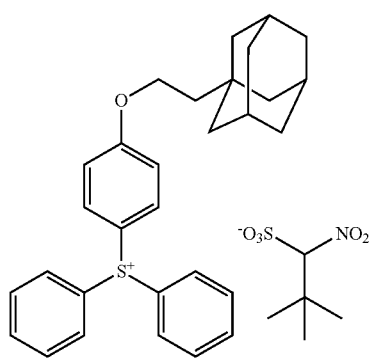
42
-continued
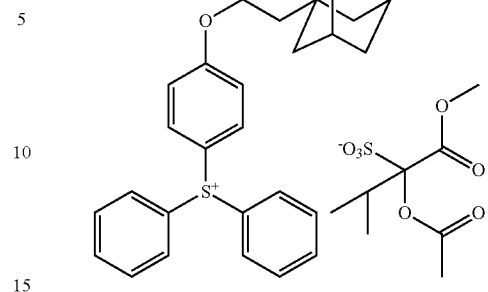
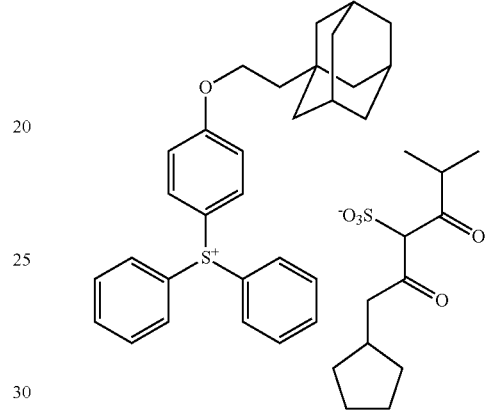
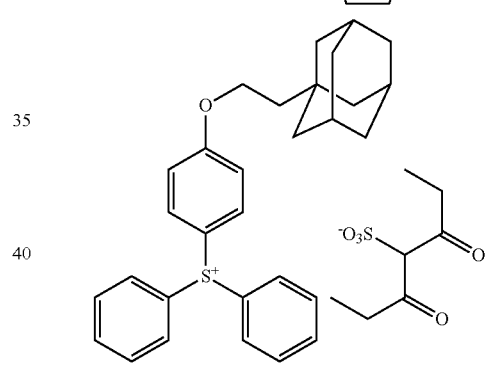
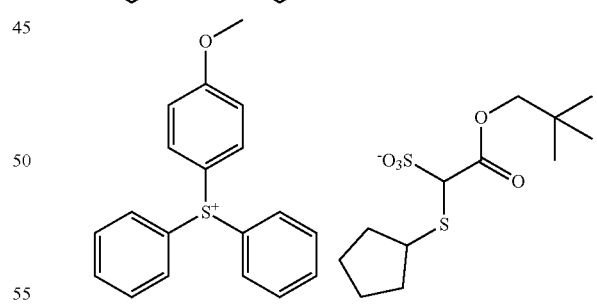
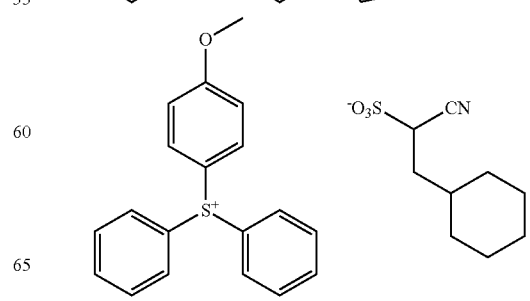

-continued
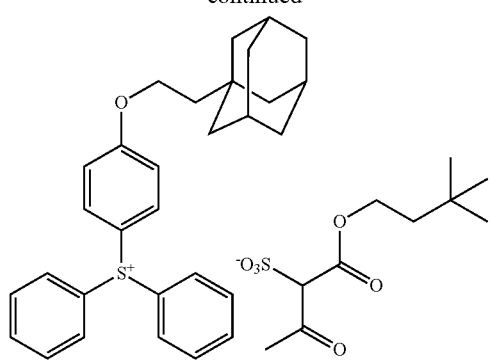
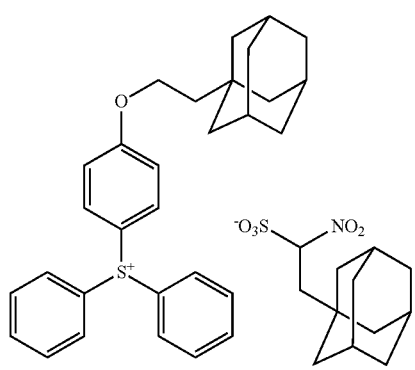
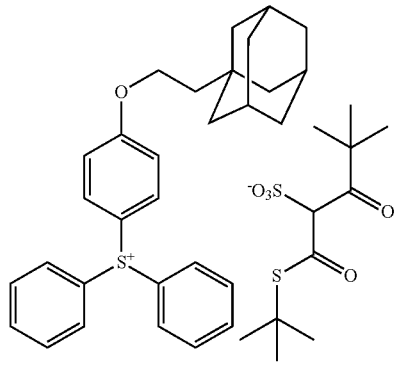
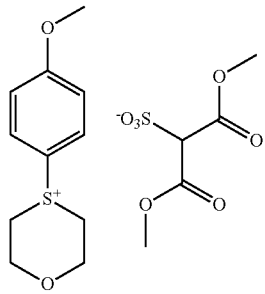
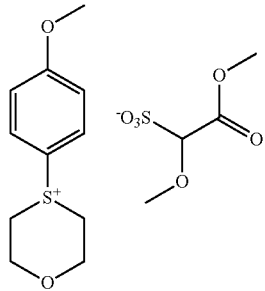
-continued
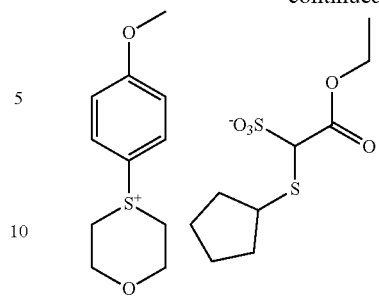
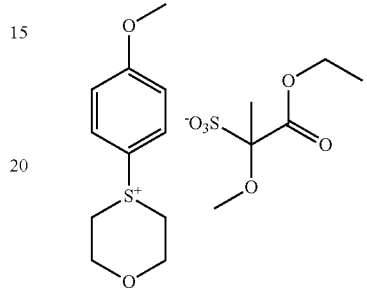
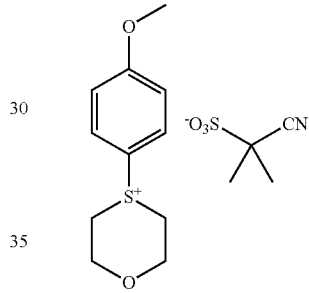
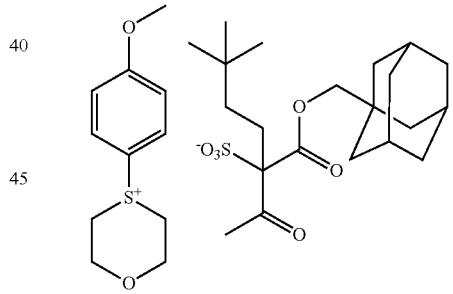
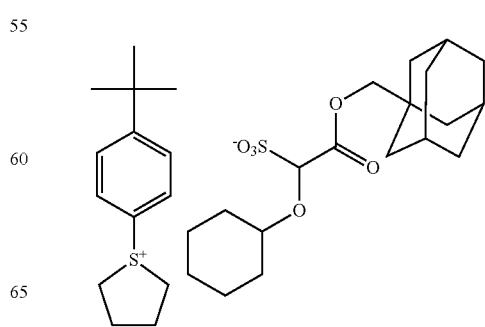

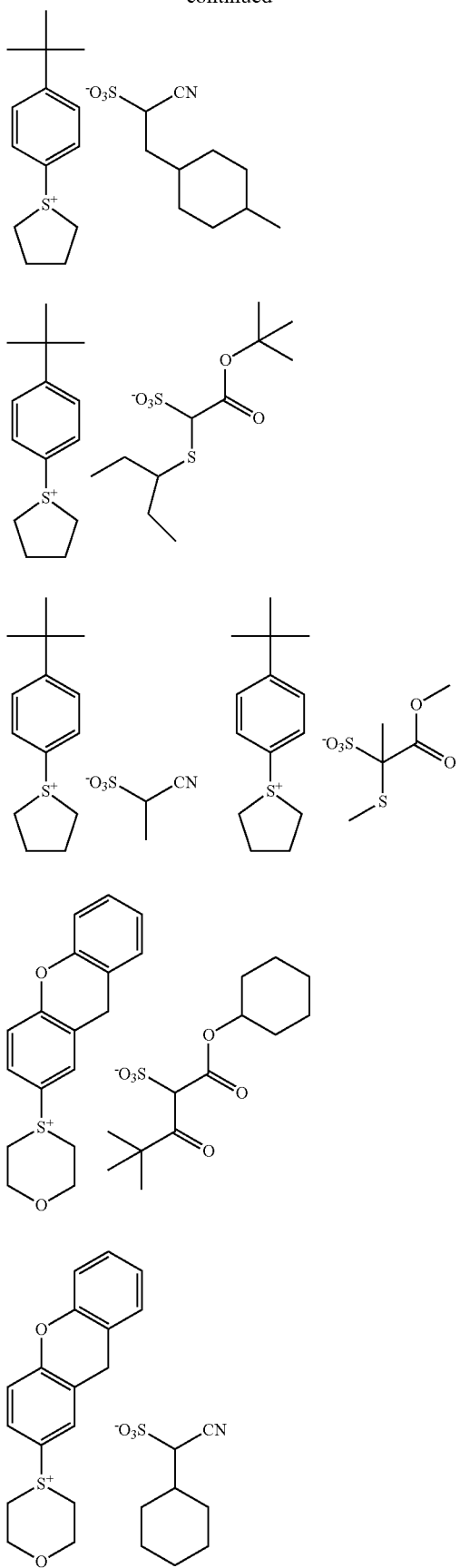
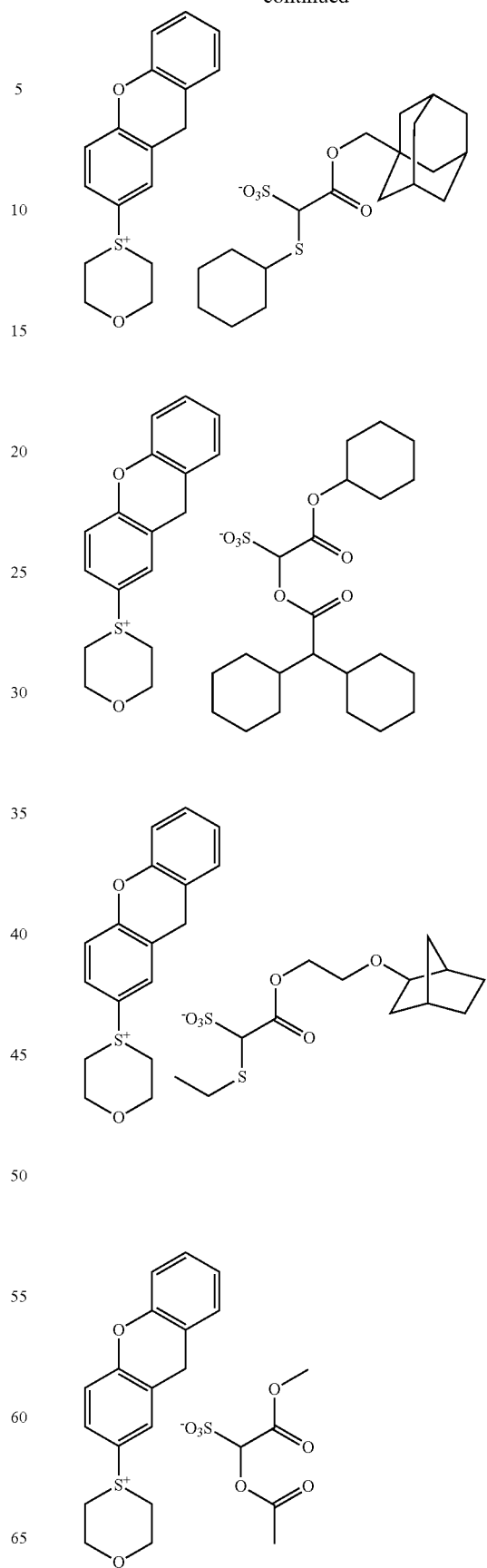

47
-continued
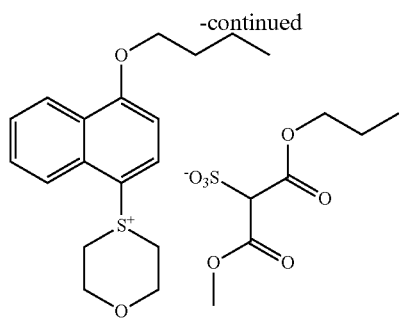
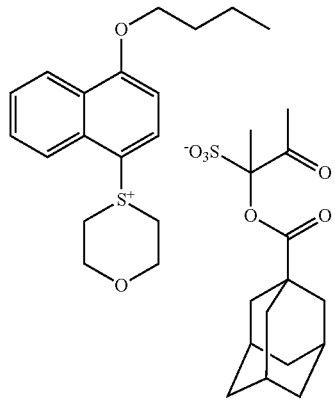
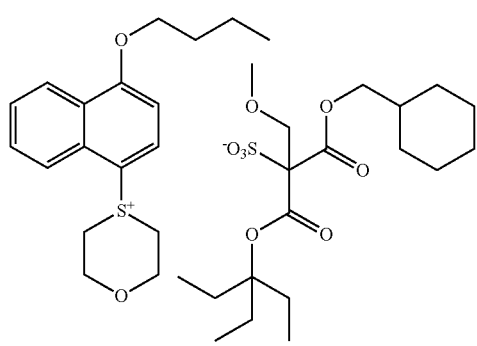
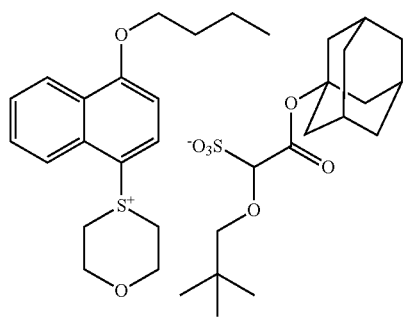
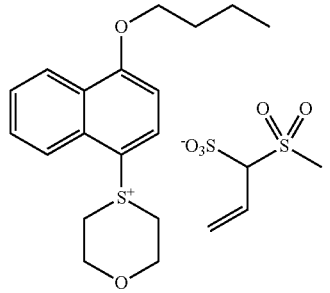
48
-continued
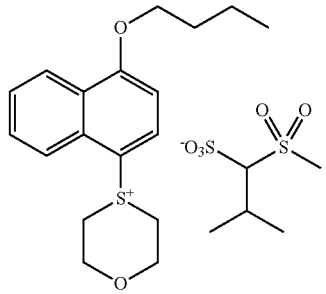
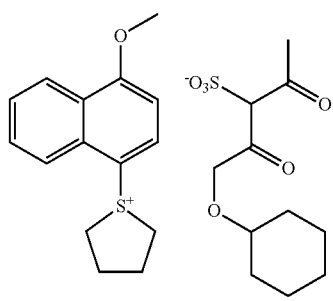
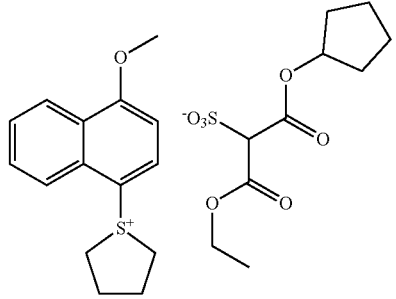
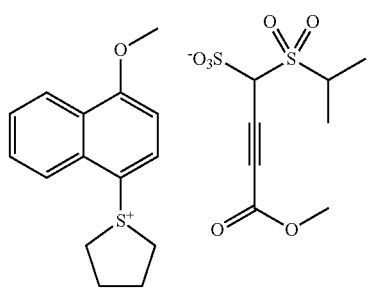
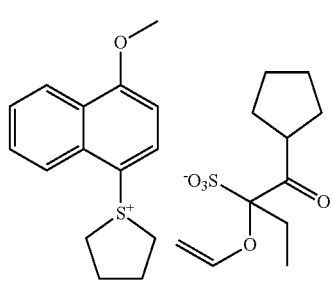

49
-continued
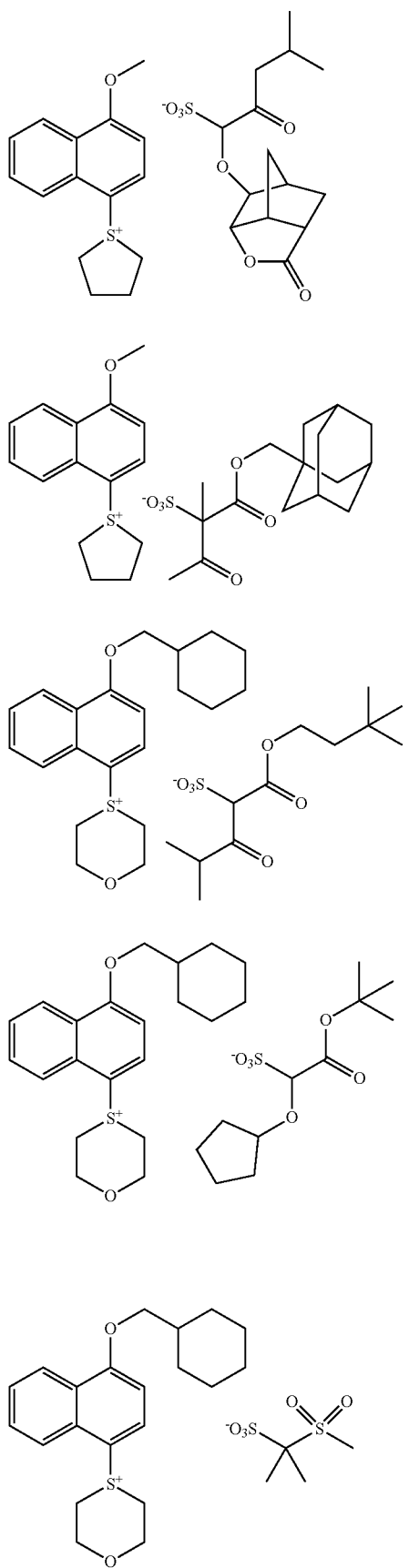
50
-continued
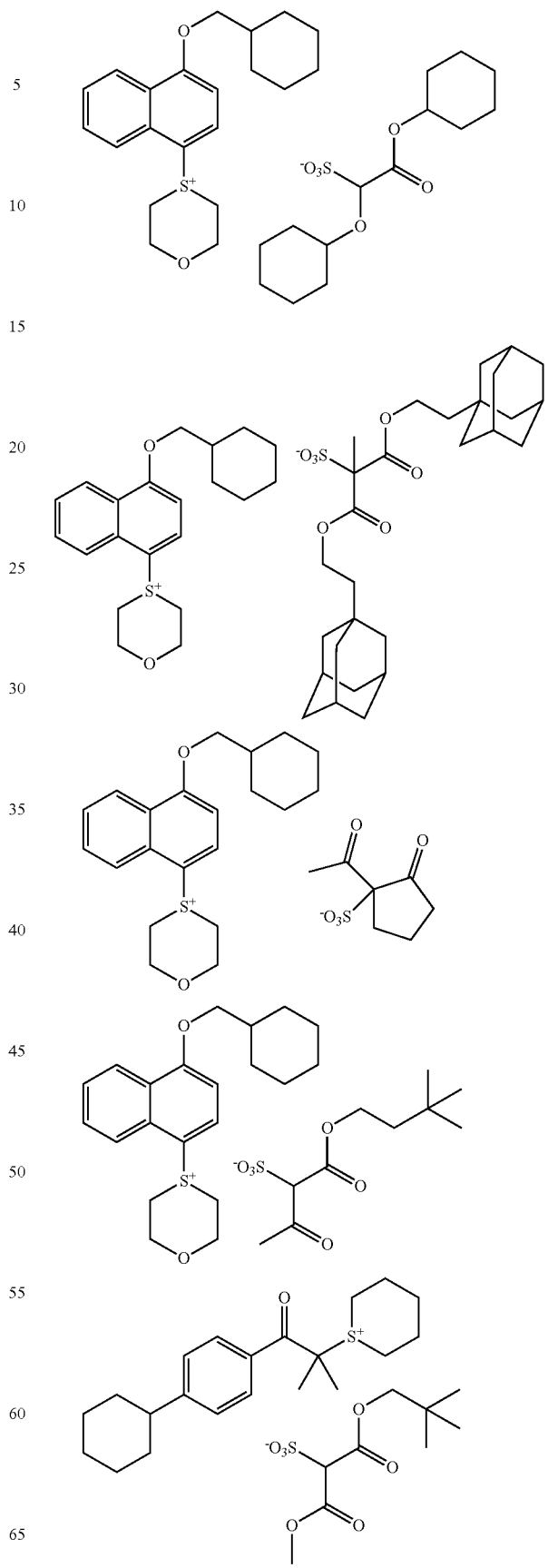

51
-continued
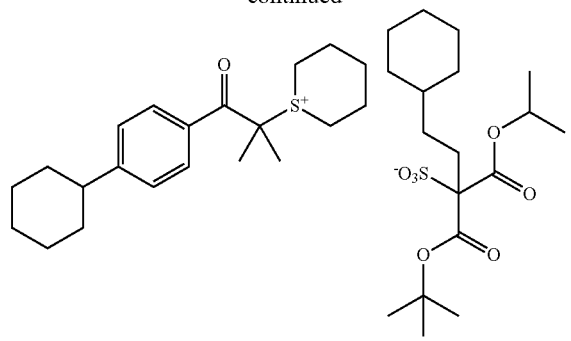
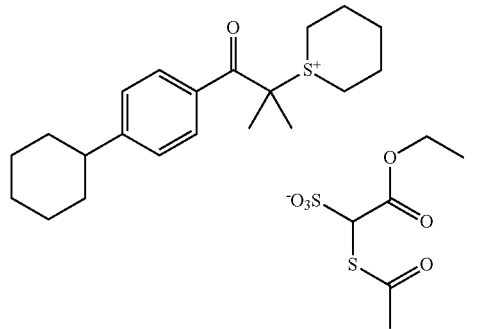
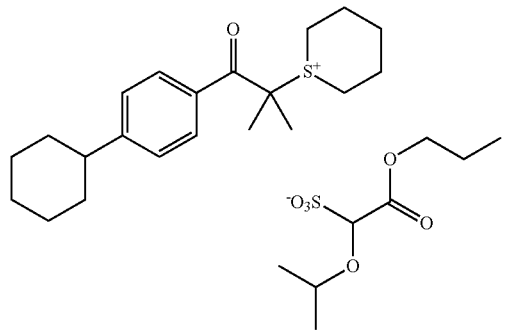
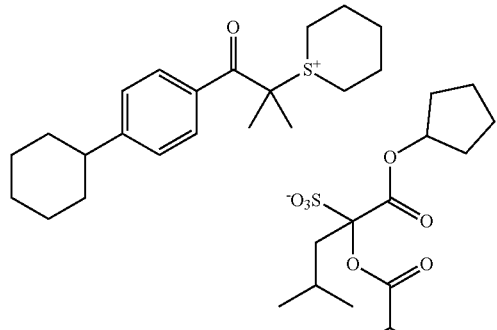
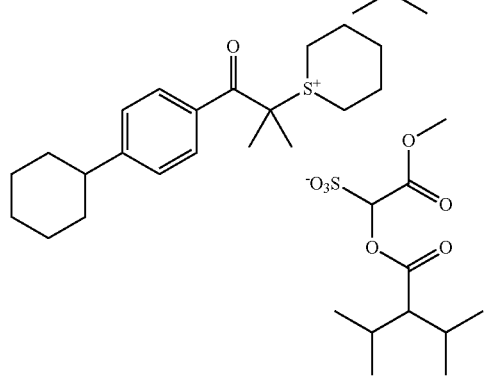
52
-continued
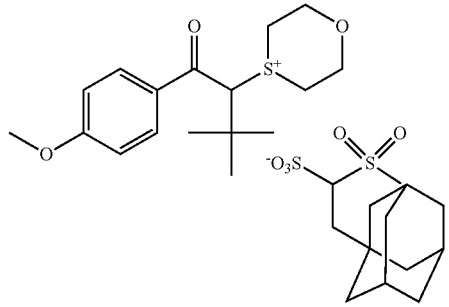
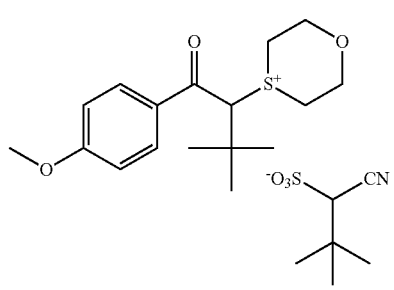
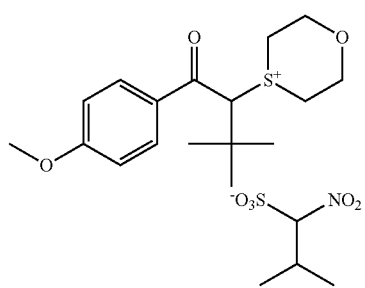
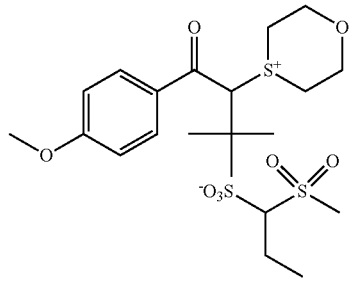
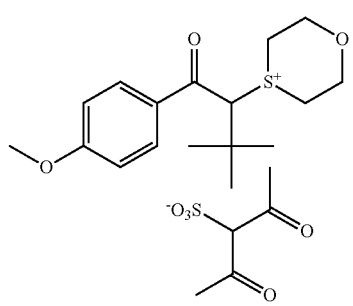

-continued

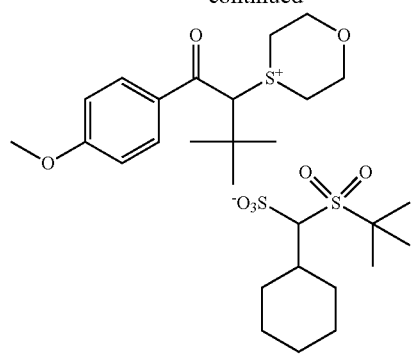

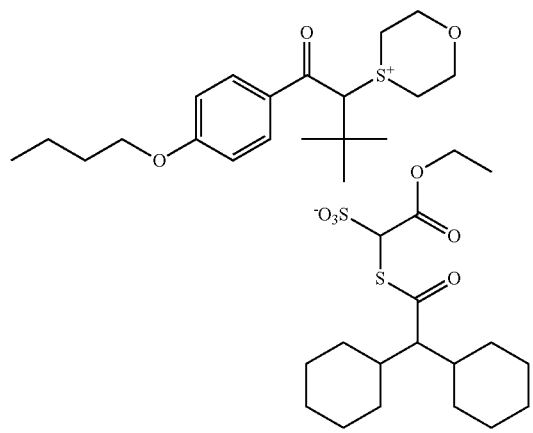

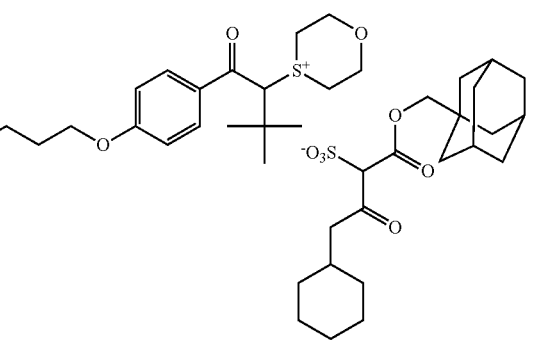

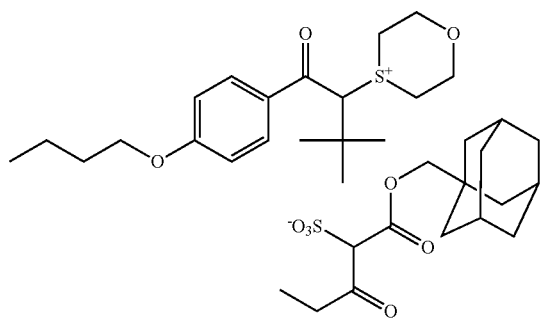

-continued

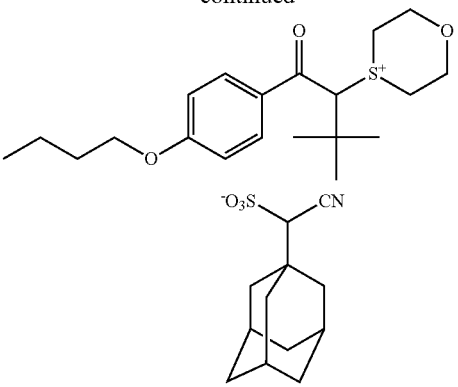

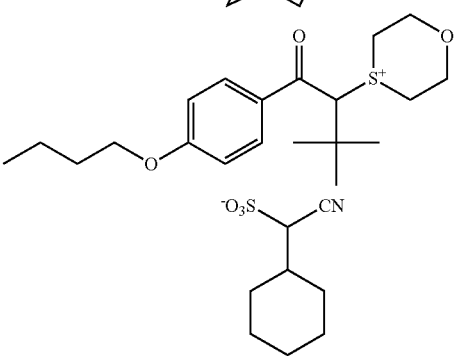

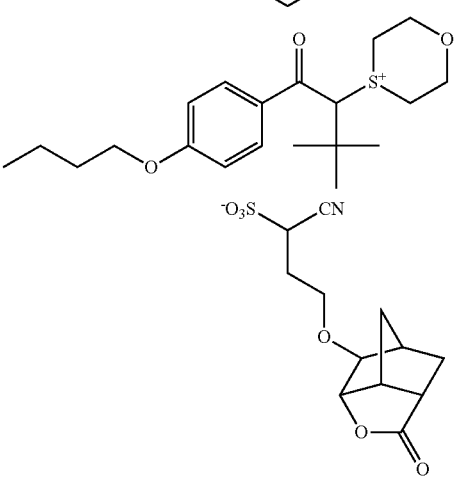

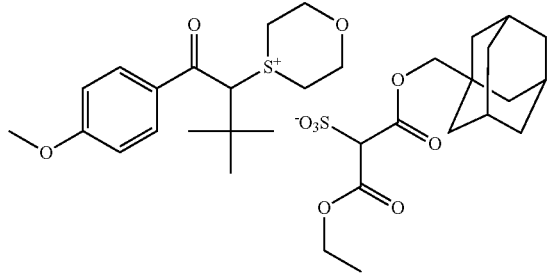

The photoacid generator (A) of the present invention may be in a form of a low-molecular-weight compound or in a form incorporated into a part of a polymer. Further, a combination of the form of a low-molecular-weight compound and the form incorporated into a part of a polymer may also be used.

In the present invention, the photoacid generator (A) is preferably a low-molecular-weight compound.

In a case where the photoacid generator (A) of the present invention is in the form of the low-molecular-weight compound, the molecular weight is preferably 3,000 or less, more preferably 2,000 or less, and still more preferably 1,000 or less.

In a case where the photoacid generator (A) of the present invention is in the form incorporated into a part of a polymer, it may be incorporated into a resin (B) which will be described later or into a resin other than the resin (B).

The photoacid generator (A) of the present invention can be synthesized by a known method, and can be synthesized in accordance with, for example, the method described in JP2007-161707A.

The photoacid generator (A) of the present invention may be used singly or in combination of two or more kinds thereof.

The content of the photoacid generator (A) of the present invention (a total sum of contents in a case where the acid generators are present in plural kinds) in the composition is preferably 0.1% to 30% by mass, more preferably 0.5% to 25% by mass, still more preferably 3% to 20% by mass, and particularly preferably 3% to 15% by mass, with respect to the total solid contents of the composition.

In a case where the compound represented by General Formula (ZI-3) or (ZI-4) is included as the photoacid generator (A) of the present invention, the content of the acid generator (a total sum of the contents in a case where the acid generators are present in plural kinds) included in the composition is preferably 5% to 35% by mass, and more preferably 7% to 30% by mass, with respect to the total solid contents of the composition.

In addition, the actinic ray-sensitive or radiation-sensitive resin composition of the embodiment of the present invention may or may not contain a photoacid generator that is different from the photoacid generator (A), but it is preferable that the actinic ray-sensitive or radiation-sensitive resin composition does not contain a photoacid generator that generates an acid having a pKa of less than −1.40 upon irradiation with actinic rays or radiation.

<Resin (B)>

The actinic ray-sensitive or radiation-sensitive resin composition of the embodiment of the present invention contains a resin which has a repeating unit containing an acid-decomposable group (hereinafter, also referred to as an "acid-decomposable resin" or a "resin (B)"). Here, the Eth sensitivity of the repeating unit containing an acid-decomposable group in the resin (B) is 5.64 or less.

The Eth sensitivity is an index corresponding to an "exposure dose required to form a pattern", and a smaller value thereof indicates that an acid-decomposable group sufficiently decomposes at a low exposure dose by an acid (typically, a protecting group in the acid-decomposable group leaves). The Eth sensitivity of the repeating unit (hereinafter also simply referred to as an "acid-decomposable repeating unit") containing an acid-decomposable group being 5.64 or less means that the acid-decomposition reactivity is high in the repeating unit containing an acid-decomposable group in a view that the upper limit of the Eth sensitivity is limited.

Next, a method for calculating the Eth sensitivity of the acid-decomposable repeating unit will be described.

<(A) Preparation of Resist Composition>

The components shown in the following table are dissolved in a solvent shown in the same table at a solid content of 3.5% by mass, and filtered through a polyethylene filter having a pore size of 0.03 μm to prepare a resist composition (actinic ray-sensitive or radiation-sensitive resin composition).

Here, the acid-decomposable resin in the resist composition is an acid-decomposable resin which has a following lactone group-containing repeating unit a and an acid-decomposable repeating unit which is a target for measurement of the Eth sensitivity at a molar ratio of 40:60 and a weight-average molecular weight (Mw) of 10,000.

TABLE 1

| Material | Concentration [wt %] of solid content |
|---|---|
| Acid-decomposable resin | 91.41 |
| PAG-a | 7.42 |
| Acid diffusion control agent a | 1.17 |
| Solvent | Ratio [wt %] |
| Propylene glycol monomethyl ether acetate (PGMEA) | 70 |
| Cyclohexanone (CyHx) | 30 |

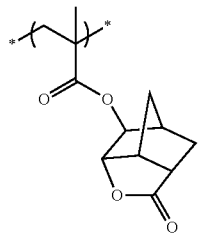

Lactone group-containing repeating unit a

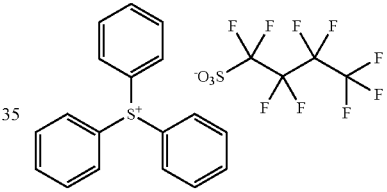

PAG-a

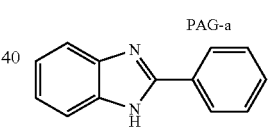

Acid diffusion control agent a

<(B) Formation of Resist Film>

ARC29A (manufactured by Nissan Chemical Industries, Ltd.) for forming an organic antireflection film is applied onto a silicon wafer, and bake at 205° C. for 60 seconds to form an antireflection film having a film thickness of 86 nm. The resist composition prepared above was applied thereonto and pre-baked (PB) at 100° C. for 60 seconds to form a resist film having a film thickness of 100 nm.

<(C) Evaluation of Eth Sensitivity>

The obtained resist film is subjected to entire-surface exposure at each exposure dose, changed within a range of 1.0 to 25.9 mJ/cm$^2$, using an ArF excimer laser scanner (PAS5500/1100 manufactured by ASML, NA 0.75, outer sigma 0.89). Further, even in a case where the composition of the embodiment of the present invention is for other uses (for example, uses for KrF exposure, EB exposure, EUV exposure, and the like) other than ArF exposure, evaluation of an Eth sensitivity is performed by ArF exposure under the condition.

Next, after performing post-exposure baking (PEB) at 85° C. for 60 seconds, puddle development is performed with butyl acetate for 30 seconds and then dried with high-speed rotation at a rotation speed (rpm) of 2,000 for 20 seconds. At this time, the film thickness after each of PEB and development was measured using VM-3110 (manufactured by Dainippon Screen Mfg. Co., Ltd.) to obtain an exposure dose-film thickness curve, from which an Eth sensitivity is determined.

In a case where a film thickness after development at an exposure dose E [mJ/cm²] is set to $T_E$ [nm], and an exposure dose at which $\gamma_E$ represented by Formula (I) becomes a maximum value $\gamma_{max}$ is denoted by $E_{max}$ and a film thickness after development is denoted by $T_{Emax}$, the Eth sensitivity is represented by Formula (2).

$$\gamma_E = \frac{(T_{E+0.3} - T_E)}{100} \times \frac{1}{\ln((E+0.3)/E)} \quad \text{Formula (1)}$$

$$E_{th} = E_{max} \times \frac{e^{(1-X_{max}/\gamma_{max}/100)}}{e^1} \quad \text{Formula (2)}$$

In Formula (2), $(1-X_{max}/\gamma_{max}/100)$ means "$1-X_{max} \div \gamma_{max} \div 100$", that is, $\{1-(X_{max}/\gamma_{max}/100)\}$.

In addition, $X_{max}$ is represented by Formula (3).

$$X_{max} = T_{Emax} - (0.0789 \times 0.7 \times E_{max} + 83.019) \quad \text{Formula (3)}$$

The method for calculating the Eth sensitivity of the acid-decomposable repeating unit has been described above, but the acid-decomposable resin used in the <(A) Preparation of Resist Composition> can be typically obtained by the following method.

A monomer corresponding to the lactone group-containing repeating unit a and a monomer corresponding to the acid-decomposable repeating unit which is a target for measurement of an Eth sensitivity at such a monomer amount ratio that the lactone group-containing repeating unit a and the acid-decomposable repeating unit which is a target for measurement of an Eth sensitivity are at a molar ratio of 40:60 in the acid-decomposable resin to be polymerized are dissolved in cyclohexanone, together with dimethyl 2,2'-azobisisobutyrate [V-601, manufactured by Wako Pure Chemical Industries, Co., Ltd.](polymerization initiator) in such an amount that the weight-average molecular weight (Mw) of the acid-decomposable resin to be polymerized becomes 10,000 (monomer concentration: 25% by mass), and polymerized at 80° C. in a nitrogen stream.

For example, a mixed cyclohexanone solution (the mass of cyclohexanone in this mixed solution is four times as the mass of the cyclohexanone in the flask) containing a polymerization initiator prepared separately and a monomer is added dropwise to cyclohexanone stored in a flask at 80° C. over 4 hours, and then further stirred at 80° C. for 2 hours. The reaction liquid was left to be cooled and then subjected to a reprecipitation treatment with a large amount of methanol/water (at a mass ratio of 9:1), and the precipitate is filtered. The obtained solid was dried in vacuo to obtain an acid-decomposable resin, which is used to determine the Eth sensitivity (acid-decomposition reactivity) of the acid-decomposable repeating unit.

As described above, the acid-decomposable resin is used in the pattern forming method of an embodiment of the present invention, and therefore, typically, in a case where an organic developer is used as the developer, a negative tone pattern is suitably formed, and in a case where an alkali developer is used as the developer, a positive tone pattern is suitably formed.

The acid-decomposable group is a group whose polarity increases through decomposition by the action of an acid, and preferably has a structure in which a polar group is protected with a group (leaving group) that leaves through decomposition by the action of an acid.

The Eth sensitivity of the acid-decomposable repeating unit tends to easily change depending to the type of the leaving group, and therefore, the Eth sensitivity of the acid-decomposable repeating unit can be set to 5.64 or less by selecting the structure of the leaving group.

Examples of the polar group include an acidic group (a group that dissociates in a 2.38%-by-mass aqueous tetramethylammonium hydroxide solution which has been used as a developer in a resist in the related art) such as a phenolic hydroxyl group, a carboxyl group, a fluorinated alcohol group (preferably a hexafluoroisopropanol group), a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, and an alcoholic hydroxyl group.

Furthermore, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol (for example, a fluorinated alcohol group (a hexafluoroisopropanol group or the like)) having the α-position substituted with an electron withdrawing group such as a fluorine atom is excluded as a hydroxyl group. The alcoholic hydroxyl group is preferably a hydroxyl group having an acid dissociation constant (pKa) from 12 to 20.

Preferred examples of the polar group include a carboxyl group, a fluorinated alcohol group (preferably a hexafluoroisopropanol group), and a sulfonic acid group.

A group which is preferable as the acid-decomposable group is a group in which a hydrogen atom of the polar group is substituted with a group that leaves by the action of an acid. Examples of the group (leaving group) that leaves by an acid include —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, an aralkyl group, or an alkenyl group.

As the alkyl group as $R_{36}$ to $R_{39}$, $R_{01}$, or $R_{02}$, an alkyl group having 1 to 8 carbon atoms is preferable, and examples thereof include a methyl group, an ethyl group, a propyl group, an n-butyl group, a sec-butyl group, a hexyl group, and an octyl group.

A cycloalkyl group as $R_{36}$ to $R_{39}$, $R_{01}$, or $R_{02}$ may be a monocyclic cycloalkyl group or a polycyclic cycloalkyl group. As the monocyclic cycloalkyl group, a cycloalkyl group having 3 to 8 carbon atoms is preferable, and examples thereof include a cyclopropyl group, a cyclobutyl group, a cyclopentyl group, a cyclohexyl group, and a cyclooctyl group. As the polycyclic cycloalkyl group, a cycloalkyl group having 6 to 20 carbon atoms is preferable, and examples thereof include an adamantyl group, a norbornyl group, an isobornyl group, a camphonyl group, a dicyclopentyl group, an α-pinene group, a tricyclodecanyl group, a tetracyclododecyl group, and an androstanyl group.

Further, at least one carbon atom in the cycloalkyl group may be substituted with heteroatoms such as an oxygen atom.

An aryl group as $R_{36}$ to $R_{39}$, $R_{O1}$, $R_{O2}$, or Ar is preferably an aryl group having 6 to 10 carbon atoms, and examples thereof include a phenyl group, a naphthyl group, and an anthryl group.

An aralkyl group as $R_{36}$ to $R_{39}$, $R_{O1}$, or $R_{O2}$ is preferably an aralkyl group with 7 to 12 carbon atoms, and is preferably, for example, a benzyl group, a phenethyl group, and a naphthylmethyl group.

An alkenyl group as $R_{36}$ to $R_{39}$, $R_{O1}$, or $R_{O2}$ is preferably an alkenyl group with 2 to 8 carbon atoms, and examples thereof include a vinyl group, an allyl group, a butenyl group, and a cyclohexenyl group.

A ring formed by the bonding of $R_{36}$ and $R_{37}$ is preferably a (monocyclic or polycyclic) cycloalkyl group. As the cycloalkyl group, monocyclic cycloalkyl groups such as a cyclopentyl group and a cyclohexyl group, and polycyclic cycloalkyl groups such as a norbornyl group, a tetracyclodecanyl group, a tetracyclododecanyl group, and an adamantyl group are preferable, monocyclic cycloalkyl groups having 5 or 6 carbon atoms are more preferable, and monocyclic cycloalkyl groups having 5 carbon atoms are particularly preferable.

The acid-decomposable group is preferably a cumyl ester group, an enol ester group, an acetal group, an acetal ester group, a tertiary alkyl ester group, or the like, and more preferably a tertiary alkyl ester group.

The resin (B) preferably has a repeating unit containing an acid-decomposable group, having an Eth sensitivity satisfying 5.64 or less, which is represented by General Formula (AI).

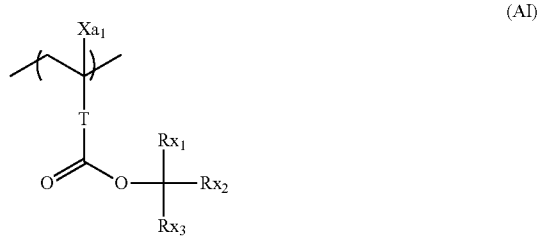

(AI)

In General Formula (AI), $Xa_1$ represents a hydrogen atom, an alkyl group, a cyano group, or a halogen atom.

T represents a single bond or a divalent linking group.

$Rx_1$ to $Rx_3$ each independently represent an alkyl group or a cycloalkyl group.

Two of $Rx_1$ to $Rx_3$ may be bonded to each other to form a ring structure.

Examples of the divalent linking group of T include an alkylene group, a —COO—Rt— group, an —O—Rt— group, and a phenylene group. In the formula, Rt represents an alkylene group or a cycloalkylene group.

T is preferably a single bond or a —COO—Rt— group. Rt is preferably an alkylene group having 1 to 5 carbon atoms, and more preferably a —CH$_2$— group, a —(CH$_2$)$_2$— group, or a —(CH$_2$)$_3$— group. T is more preferably a single bond.

The alkyl group of $Xa_1$ may have a substituent, and examples of the substituent include a hydroxyl group and a halogen atom (preferably a fluorine atom).

The alkyl group of $Xa_1$ is preferably an alkyl group having 1 to 4 carbon atoms, and examples thereof include a methyl group, an ethyl group, a propyl group, a hydroxymethyl group, and a trifluoromethyl group, with a methyl group being preferred.

$Xa_1$ is preferably a hydrogen atom or a methyl group.

The alkyl group of each of $Rx_1$, $Rx_2$, and $Rx_3$ may be linear or branched, and preferred examples thereof include a methyl group, an ethyl group, an n-propyl group, an isopropyl group, an n-butyl group, an isobutyl group, and a t-butyl group. The number of carbon atoms of the alkyl group is preferably 1 to 10, and more preferably 1 to 5.

The cycloalkyl group of each of $Rx_1$, $Rx_2$, and $Rx_3$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

As the ring structure formed by the bonding of two of $Rx_1$, $Rx_2$, and $Rx_3$, a monocyclic cycloalkane ring such as a cyclopentyl ring and a cyclohexyl ring, and a polycyclic cycloalkyl group such as a norbornane ring, a tetracyclodecane ring, a tetracyclododecane ring, and an adamantane ring are preferable, and a monocyclic cycloalkane ring having 5 or 6 carbon atoms is particularly preferable.

$Rx_1$, $Rx_2$, and $Rx_3$ are each independently preferably an alkyl group, and more preferably a linear or branched alkyl group having 1 to 4 carbon atoms.

Each of the groups may have a substituent, and examples of the substituent include an alkyl group (having 1 to 4 carbon atoms), a cycloalkyl group (having 3 to 8 carbon atoms), a halogen atom, an alkoxy group (having 1 to 4 carbon atoms), a carboxyl group, and an alkoxycarbonyl group (having 2 to 6 carbon atoms), with the groups having 8 or less carbon atoms being preferable. Among those, from the viewpoint of increasing a dissolution contrast for a developer (in particular, a developer including an organic solvent) before and after acid decomposition, the substituent is more preferably a substituent not having a heteroatom such as an oxygen atom, a nitrogen atom, and a sulfur atom (for example, a substituent other than an alkyl group substituted with a hydroxyl group is more preferable), still more preferably a group composed only of a hydrogen atom and a carbon atom, and particularly preferably a linear or branched alkyl group or a cycloalkyl group.

In General Formula (AI), $Rx_1$ to $Rx_3$ are each independently an alkyl group, and it is preferable that two of $Rx_1$ to $Rx_3$ are not bonded to each other to form a ring structure. Thus, there is tendency that an increase in the volume of a group represented by —C($Rx_1$)($Rx_2$)($Rx_3$) as the group capable of decomposing by the action of an acid to leave can be suppressed, and a decrease in the volume of the exposed area can be suppressed in an exposing step and a post-exposure baking step that may be carried out after the exposing step.

Specific examples of the repeating unit represented by General Formula (AI), which has an Eth sensitivity satisfying 5.64 or less, are shown below, but the present invention is not limited to these specific examples.

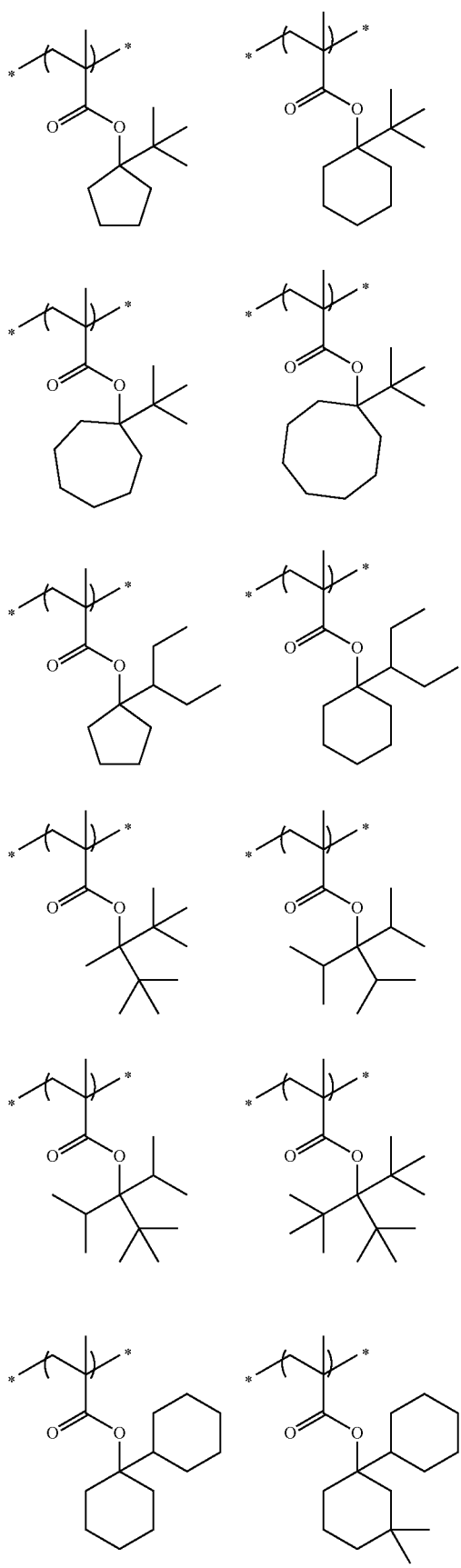
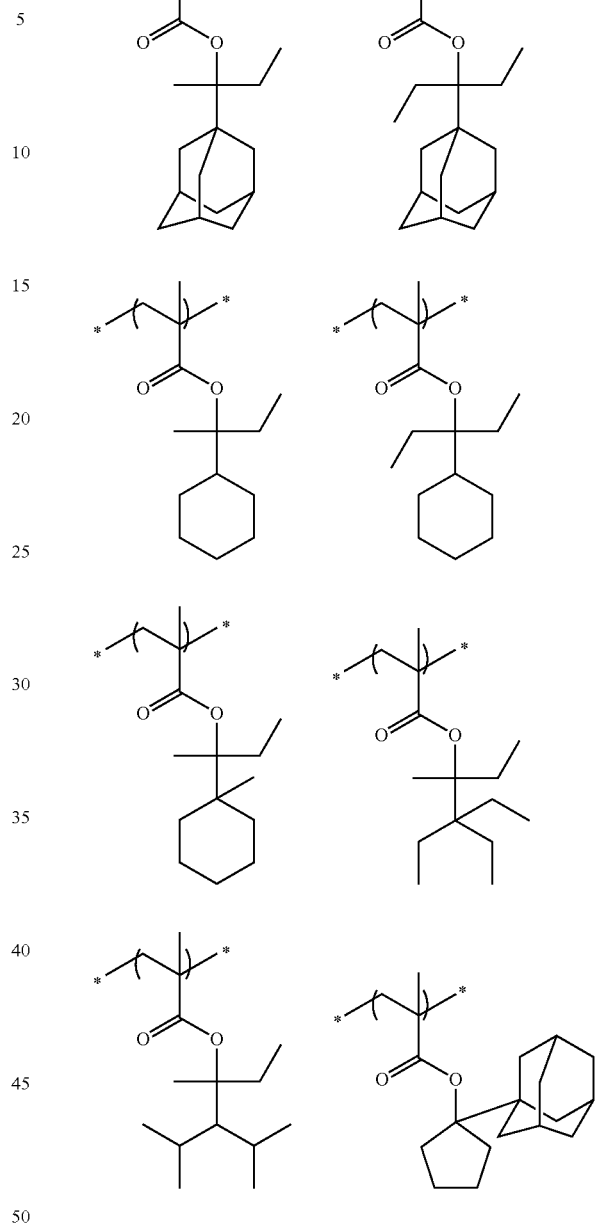
Moreover, the resin (B) preferably has a repeating unit containing an acid-decomposable group, having an Eth sensitivity satisfying 5.64 or less, which is represented by General Formula (A) or (B).
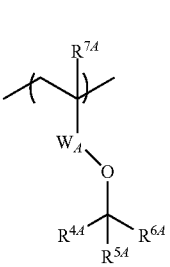
(A)

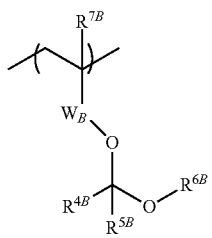

In General Formula (A), $R^{4A}$, $R^{5A}$, and $R^{6A}$ each independently represent a monovalent organic group. $W_A$ represents —CO— or a divalent aromatic ring group. $R^{7A}$ represents a hydrogen atom, a methyl group, or a trifluoromethyl group. $R^{5A}$ and $R^{6A}$ may be bonded to each other to form a ring.

In General Formula (B), $R^{4B}$, $R^{5A}$, and $R^{6B}$ each independently represent a hydrogen atom or a monovalent organic group. $R^{5B}$ and $R^{6B}$ may be bonded to each other to form a ring. $W_B$ represents —CO— or a divalent aromatic ring group. $R^{7B}$ represents a hydrogen atom, a methyl group, or a trifluoromethyl group.

The monovalent organic group as each of $R^{4A}$, $R^{5A}$, $R^{6A}$, $R^{4B}$, $R^{5B}$, and $R^{6B}$ preferably has 1 to 30 carbon atoms, more preferably has 1 to 20 carbon atoms, still more preferably has 1 to 10 carbon atoms, and examples thereof include an alkyl group, a cycloalkyl group, an aryl group, an aralkyl group, an alkenyl group, an alkylcarbonyl group, a cycloalkylcarbonyl group, and an alkyloxycarbonyl group. These groups may further have a substituent.

The substituent may be any one of a halogen atom, an alkyl group (which may be linear or branched, and preferably has 1 to 12 carbon atoms), a cycloalkyl group (which may be any one of a monocycle, a polycycle, or a spiro ring, and preferably has 3 to 20 carbon atoms), an aryl group (preferably having 6 to 14 carbon atoms), a hydroxy group, a carbonyl group, an ether group, a cyano group, an alkoxy group, an ester group, an amido group, a urethane group, a ureido group, a thioether group, a sulfonamido group, a sulfonic acid ester group, and a group formed by combination of two or more selected from these atoms and groups.

Examples of the divalent aromatic ring group as each of $W_A$ and $W_B$ include a phenylene group, a naphthylene group, and an anthracylene group, with the phenylene group being preferable.

The divalent aromatic ring group may further have a substituent, and specific examples of the substituent are the same as those mentioned as the specific examples of the substituent that may be contained in the monovalent organic group as each of $R^{4A}$, $R^{5A}$, $R^{6A}$, $R^{4B}$, $R^{5B}$, and $R^{6B}$.

Specific examples of the repeating unit represented by General Formula (A) or (B), which has an Eth sensitivity satisfying 5.64 or less, include the repeating units mentioned as specific examples of the repeating unit represented by General Formula (AI) or the following repeating units, but the present invention is not limited to these specific examples.

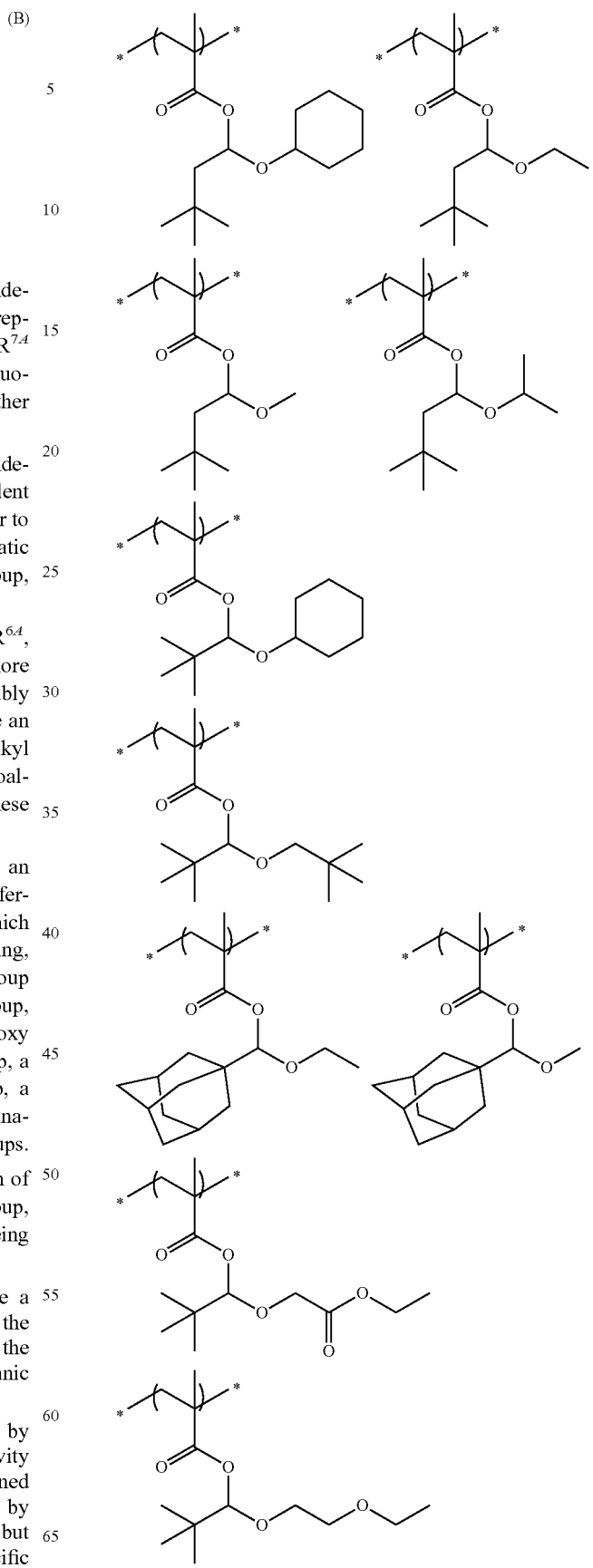

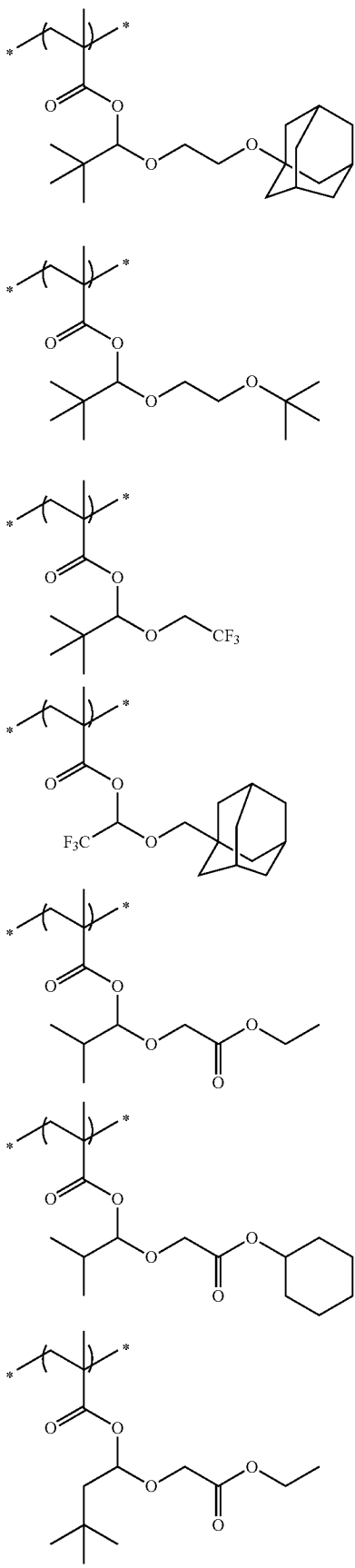
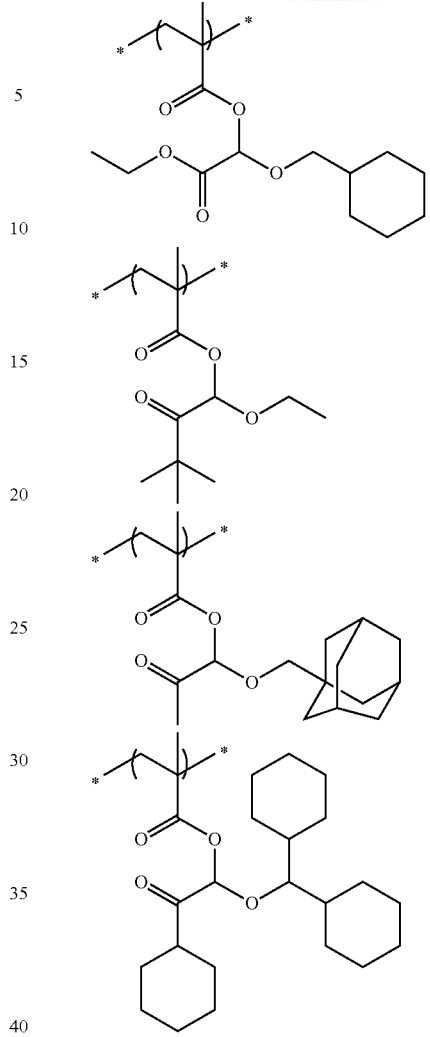

Furthermore, the resin (B) preferably has the repeating unit described in paragraphs [0057] to [0071] of JP2014-202969A, which has an Eth sensitivity satisfying 5.64 or less, as the repeating unit having an acid-decomposable group.

In addition, the resin (B) may have the repeating unit having an alcoholic hydroxyl group described in paragraphs [0072] and [0073] of JP2014-202969A, which has an Eth sensitivity satisfying 5.64 or less, as the repeating unit having an acid-decomposable group.

The Eth sensitivity of the acid-decomposable repeating unit contained in the resin (B) is usually 5.20 or more. The Eth sensitivity of the acid-decomposable repeating unit is preferably from 5.20 to 5.64, more preferably from 5.20 to 5.55, and still more preferably from 5.20 to 5.50.

The resin (B) may have one kind or two or more kinds of the repeating unit containing an acid-decomposable group.

Moreover, the resin (B) may have a repeating unit having an Eth sensitivity of more than 5.64 as the acid-decomposable repeating unit. In this case, the Eth sensitivity of the acid-decomposable repeating unit having an Eth sensitivity of more than 5.64 is usually 8.00 or less.

Examples of the repeating unit having an Eth sensitivity of more than 5.64 include the repeating units shown below.

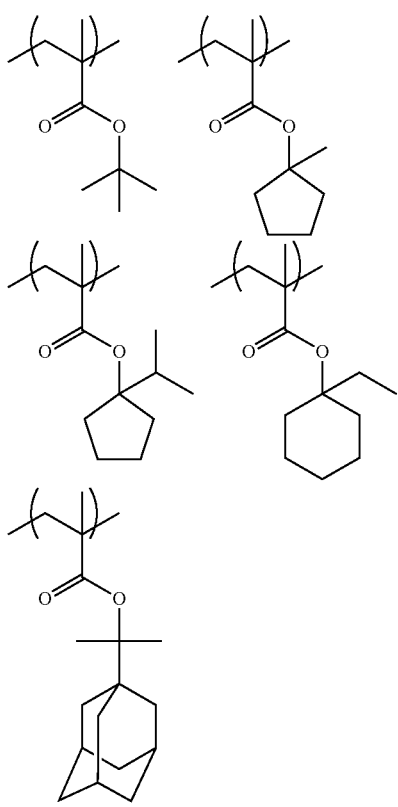

As described above, the resin (B) may have two or more kinds of the acid-decomposable repeating unit having an Eth sensitivity of 5.64 or less, and may also have a repeating unit having an Eth sensitivity of more than 5.64, in addition to the acid-decomposable repeating unit having an Eth sensitivity of 5.64 or less, but in any cases where the resin (B) has a plurality of kinds of the acid-decomposable repeating units, the Eth sensitivity of the acid-decomposable repeating unit in the resin (B) is a weighted average of the Eth sensitivity of the respective acid-decomposable repeating units, based on the weighted value of the number of moles of each acid-decomposable repeating unit. In other words, the Eth sensitivity of the acid-decomposable repeating unit is a sum of values obtained by multiplying the mole fractions of the respective acid-decomposable repeating units with respect to all the acid-decomposable repeating units by the Eth sensitivity of each acid-decomposable repeating unit.

Therefore, in a case where the resin (B) has a plurality of the acid-decomposable repeating units, the Eth sensitivity of the acid-decomposable repeating unit calculated from the weighted average is 5.64 or less, and a preferred range of the Eth sensitivity is also the same.

In a case where the resin (B) has a repeating unit having an Eth sensitivity of more than 5.64, in addition to the acid-decomposable repeating unit having an Eth sensitivity of 5.64 or less, the content of the acid-decomposable repeating unit having an Eth sensitivity of 5.64 or less is preferably 50% by mole or more with respect to all the acid-decomposable repeating units.

The content of the repeating unit containing an acid-decomposable group (a total sum of contents in a case where the repeating unit containing an acid-decomposable group are present in plural kinds) in the resin (B) is preferably 20% to 90% by mole, and more preferably 40% to 80% by mole, with respect to all the repeating units of the resin (B). It is preferable that the resin (B) has the repeating unit represented by General Formula (AI) and the content of the repeating unit represented by General Formula (AI) with respect to all the repeating units of the resin (B) is 40% by mole or more.

It is also preferable that the resin (B) has a repeating unit having at least one selected from the group consisting of a lactone structure, a sultone structure, and a carbonate structure.

As the lactone structure or the sultone structure, any one having a lactone structure or sultone structure can be used, and the structure is preferably a 5- to 7-membered ring lactone structure or a 5- to 7-membered ring sultone structure, and more preferably a 5- to 7-membered ring lactone structure to which another ring structure is fused so as to form a bicyclo structure or a spiro structure, or a 5- to 7-membered ring sultone structure to which another ring structure is fused so as to form a bicyclo structure or a spiro structure. The resin (B) still more preferably has a repeating unit having a lactone structure represented by any one of General Formulae (LC1-1) to (LC1-21), or a repeating unit having a sultone structure represented by any one of General Formulae (SL-1) to (SL-3). Further, the lactone structure or the sultone structure may be directly bonded to a main chain. A preferred lactone structure or sultone structure is (LC1-1), (LC1-4), (LC1-5), (LC1-6), (LC1-13), (LC-14), or (LC1-17), and a particularly preferred lactone structure is (LC1-4). By using such a specific lactone structure, LER and development defects are relieved.

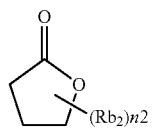

LC1-1

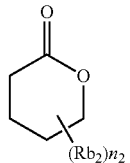

LC1-2

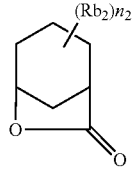

LC1-3

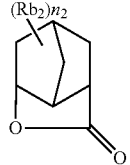

LC1-4

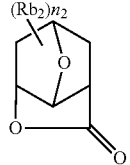

LC1-5

-continued
LC1-6
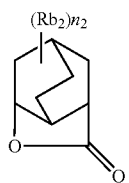
LC1-7
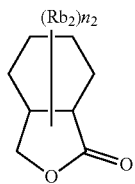
LC1-8
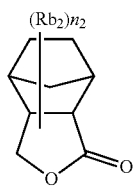
LC1-9
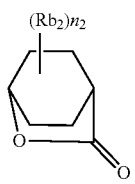
LC1-10
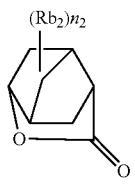
LC1-11
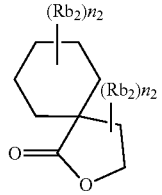
LC1-12
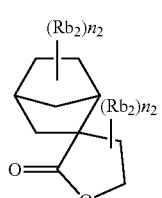
LC1-13
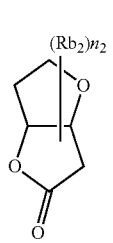
-continued
LC1-14
LC1-15
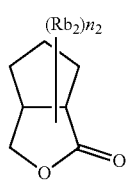
LC1-16
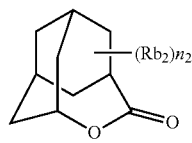
LC1-17
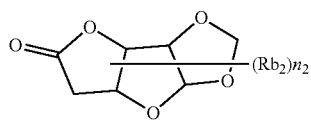
LC1-18
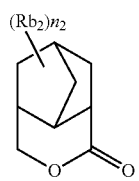
LC1-19
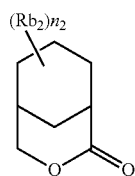
LC1-20
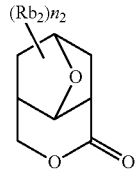
LC1-21
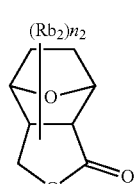
SL1-1
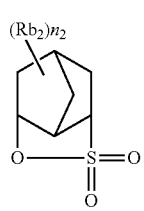

-continued

SL1-2

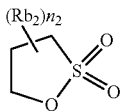

SL1-3

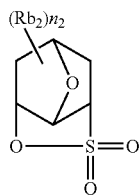

The lactone structure moiety or the sultone structure moiety may or may not have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, and an acid-decomposable group. Among these, an alkyl group having 1 to 4 carbon atoms, a cyano group, and an acid-decomposable group are more preferable. $n_2$ represents an integer of 0 to 4. In a case where $n_2$ is 2 or more, the substituents ($Rb_2$) which are present in plural numbers may be the same as or different from each other. Further, the substituents ($Rb_2$) which are present in plural numbers may be bonded to each other to form a ring.

The repeating unit having a lactone structure or sultone structure usually has optical isomers, and any of the optical isomers may be used. Further, one kind of optical isomer may be used singly or a plurality of optical isomers may be mixed and used. In a case of mainly using one kind of optical isomer, the optical purity (ee) thereof is preferably 90% or more, and more preferably 95% or more.

The repeating unit having a lactone structure or sultone structure is preferably a repeating unit represented by General Formula (III).

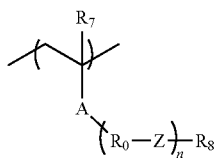

(III)

In General Formula (III),

A represents an ester bond (a group represented by —COO—) or an amide bond (a group represented by —CONH—).

In a case where $R_0$'s are present in plural numbers, they each independently represent an alkylene group, a cycloalkylene group, or a combination thereof.

In a case where Z's are present in plural numbers, they each independently represent a single bond, an ether bond, an ester bond, an amide bond, a urethane bond (a group represented by

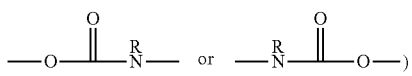

or a urea bond (a group represented by

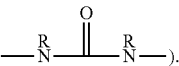

Here, R's each independently represent a hydrogen atom, an alkyl group, a cycloalkyl group, or an aryl group.

$R_8$ represents a monovalent organic group having a lactone structure or sultone structure.

n is the repetition number of the structure represented by —$R_0$—Z—, represents an integer of 0 to 5, and is preferably 0 or 1, and more preferably 0. In a case where n is 0, —$R_0$—Z— is not present, leading to a single bond.

$R_7$ represents a hydrogen atom, a halogen atom, or an alkyl group.

The alkylene group or the cycloalkylene group of $R_0$ may have a substituent.

Z is preferably an ether bond or an ester bond, and particularly preferably an ester bond.

The alkyl group of $R_7$ is preferably an alkyl group having 1 to 4 carbon atoms, more preferably a methyl group or an ethyl group, and particularly preferably a methyl group.

The alkylene group or the cycloalkylene group of $R_0$, and the alkyl group in $R_7$ may be each substituted, and examples of the substituent include a halogen atom such as a fluorine atom, a chlorine atom, and a bromine atom, a mercapto group, a hydroxyl group, an alkoxy group such as a methoxy group, an ethoxy group, an isopropoxy group, a t-butoxy group, and a benzyloxy group, and an acyloxy group such as an acetyloxy group and a propionyloxy group.

$R_7$ is preferably a hydrogen atom, a methyl group, a trifluoromethyl group, or a hydroxymethyl group.

The preferred chained alkylene group in $R_0$ is chained alkylene, preferably having 1 to carbon atoms, and more preferably having 1 to 5 carbon atoms, and examples thereof include a methylene group, an ethylene group, and a propylene group. Preferred examples of the cycloalkylene group include a cycloalkylene group having 3 to 20 carbon atoms, and examples thereof include a cyclohexylene group, a cyclopentylene group, a norbornylene group, and an adamantylene group. In order to express the effects of the present invention, a chained alkylene group is more preferable, and a methylene group is particularly preferable.

The monovalent organic group having a lactone structure or sultone structure represented by $R_8$ is not limited as long as it has the lactone structure or sultone structure, specific examples thereof include a lactone structure or sultone structure represented by any one of General Formulae (LC1-1) to (LC1-21) and (SL1-1) to (SL1-3), and among these, the structure represented by (LC1-4) is particularly preferable. Further, $n_2$ in each of (LC1-1) to (LC1-21) is more preferably 2 or less.

Furthermore, $R_8$ is preferably a monovalent organic group having an unsubstituted lactone structure or sultone structure, or a monovalent organic group having a lactone structure or sultone structure having a methyl group, a cyano group, or an alkoxycarbonyl group as a substituent, and more preferably a monovalent organic group having a lactone structure having a cyano group as a substituent (cyanolactone).

Specific examples of the repeating unit having a lactone structure or sultone structure are shown below, but the present invention is not limited thereto.

(In the fomulae, Rx represents H, CH₃, CH₂OH, or CF₃.)
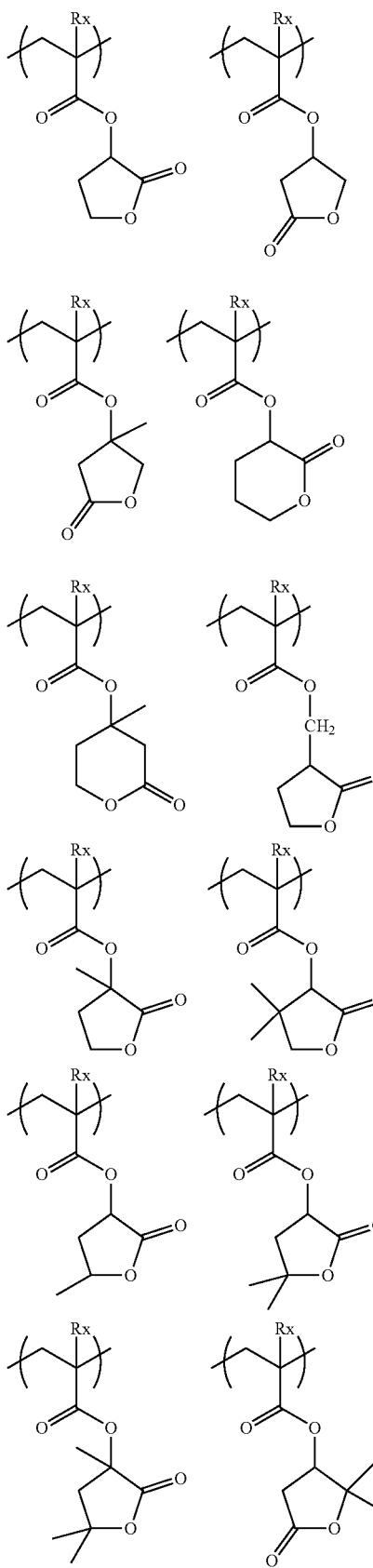
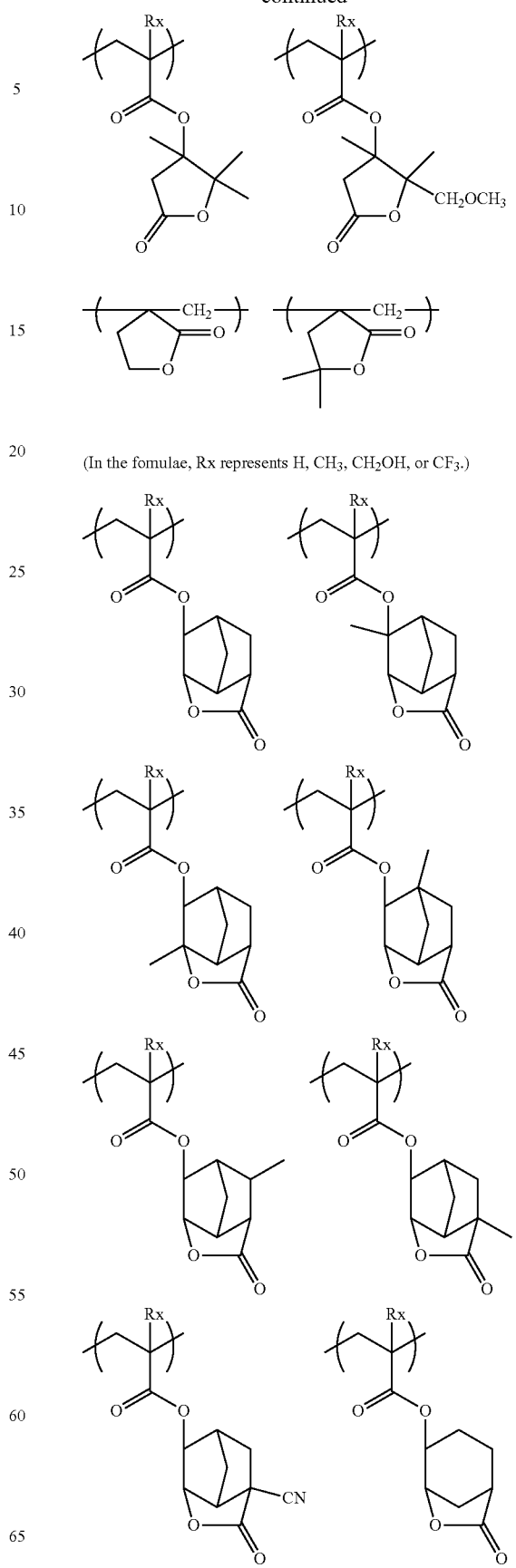
-continued
(In the fomulae, Rx represents H, CH₃, CH₂OH, or CF₃.)

-continued
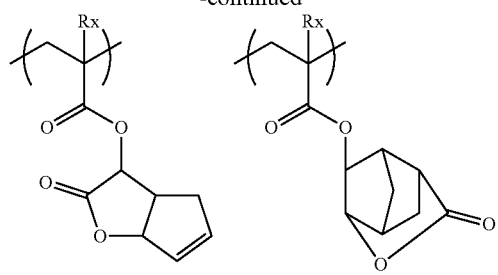
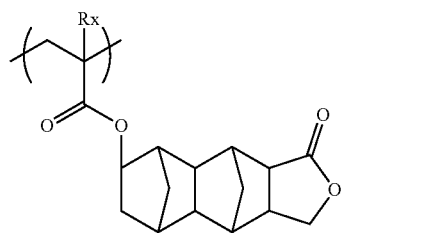
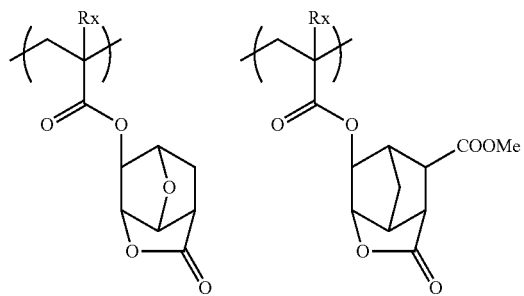
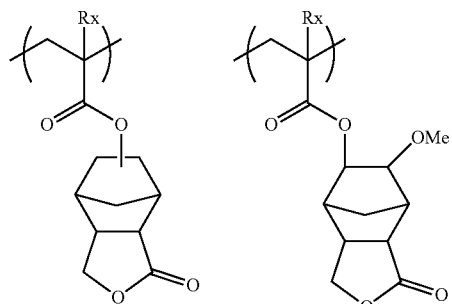
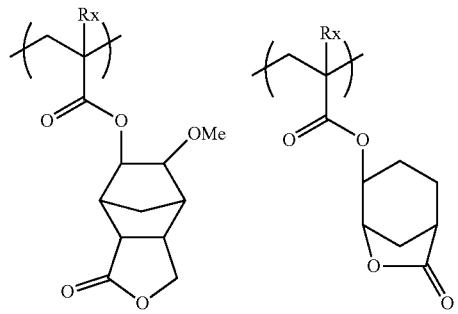
-continued
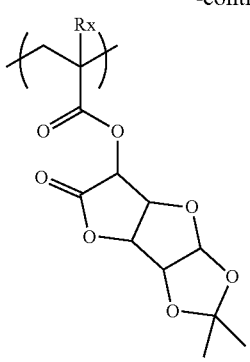
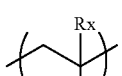
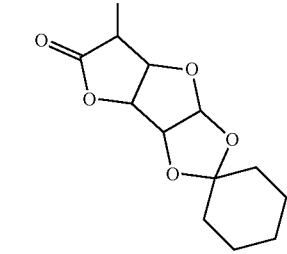
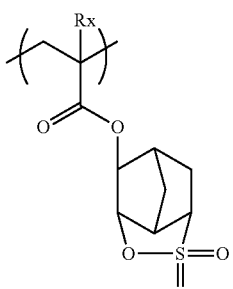
(In the formulae, Rx represents H, CH$_3$, CH$_2$OH, or CF$_3$.)
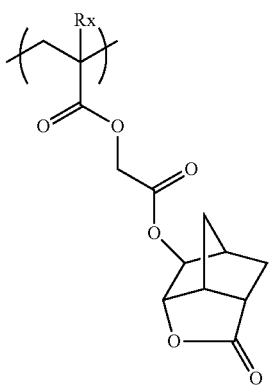

77
-continued
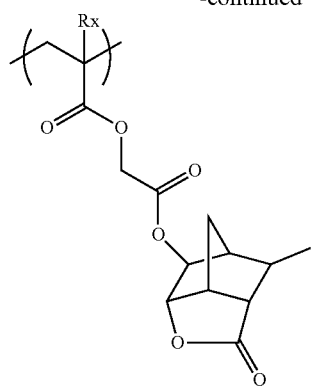
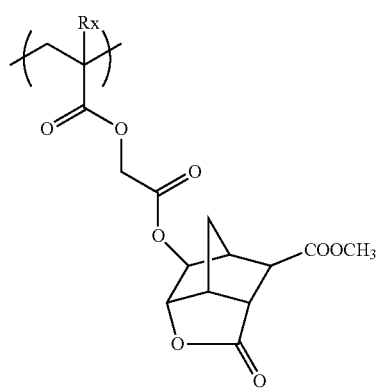
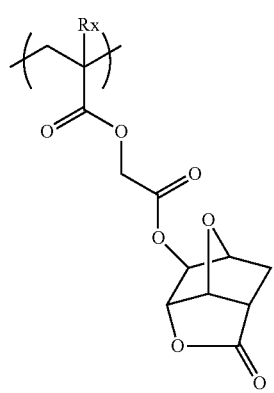
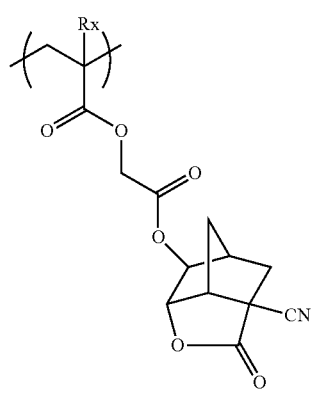
78
-continued
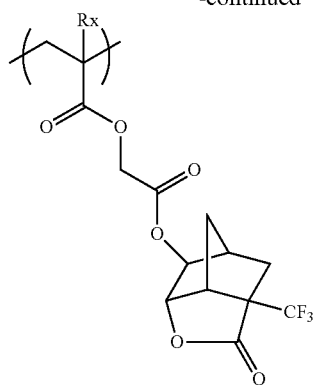
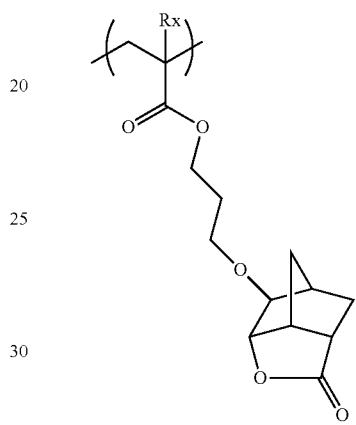
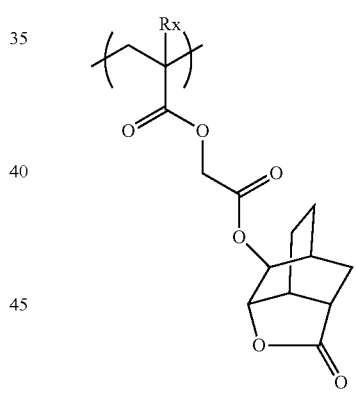
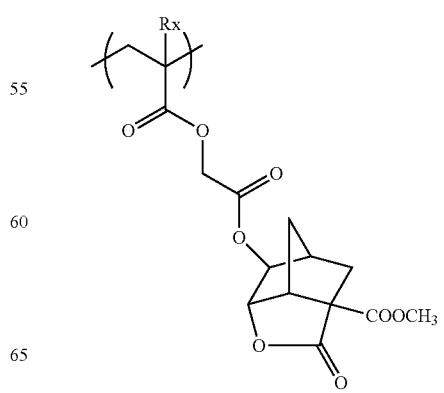

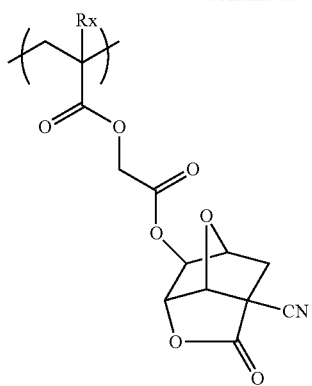
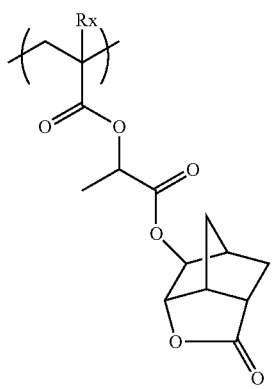
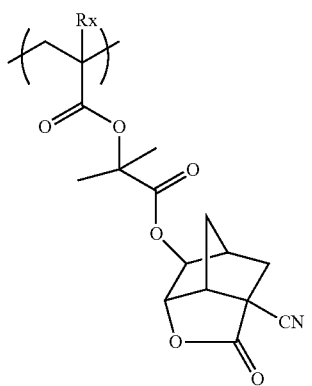
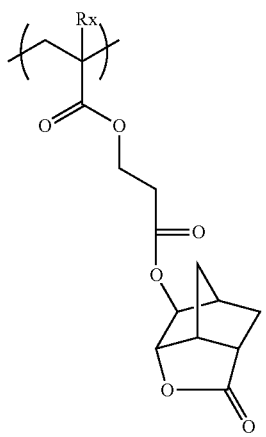

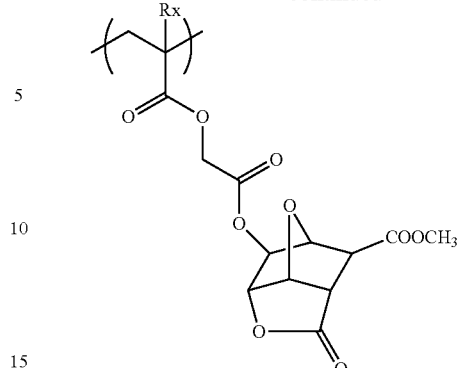
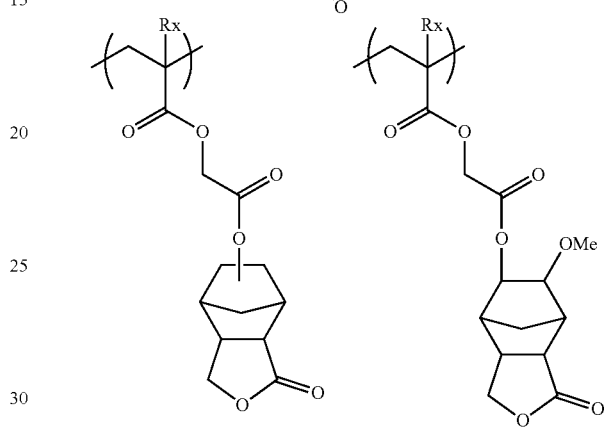

It is also possible to use a combination of two or more kinds of repeating units having a lactone structure or sultone structure.

In a case where the resin (B) contains a repeating unit having a lactone structure or sultone structure, the content of the repeating unit having a lactone structure or sultone structure is preferably 5% to 60% by mole, more preferably 5% to 55% by mole, and still more preferably 10% to 50% by mole, with respect to all the repeating units in the resin (B).

Moreover, the resin (B) may have a repeating unit having a carbonate structure. In this case, the carbonate structure is preferably a cyclic carbonate ester structure. As the repeating unit having a cyclic carbonate ester structure, a hydrophilic repeating unit is preferable, whereby swelling during the development is suppressed.

The repeating unit having a cyclic carbonate ester structure is preferably a repeating unit represented by General Formula (A-1).

(A-1)

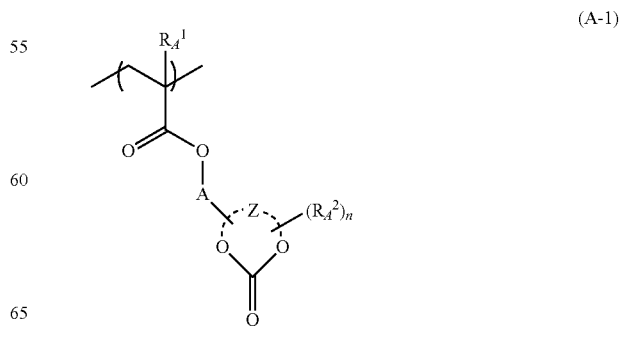

In General Formula (A-1), $R_A^1$ represents a hydrogen atom or an alkyl group.

In a case where n is 2 or more, $R_A^2$'s each independently represent a substituent.

A represents a single bond or a divalent linking group.

Z represents an atomic group which forms a monocyclic or polycyclic structure together with a group represented by —O—C(=O)—O— in the formula.

n represents an integer of 0 or more.

General Formula (A-1) will be described in detail.

The alkyl group represented by $R_A^1$ may have a substituent such as a fluorine atom. $R_A^1$ is preferably a hydrogen atom, a methyl group, or a trifluoromethyl group, and more preferably a methyl group.

The substituent represented by $R_A^2$ is, for example, an alkyl group, a cycloalkyl group, a hydroxyl group, an alkoxy group, an amino group, or an alkoxycarbonylamino group. The substituent is preferably an alkyl group having 1 to 5 carbon atoms, and examples thereof include a linear alkyl group having 1 to 5 carbon atoms, such as a methyl group, an ethyl group, a propyl group, and a butyl group, and a branched alkyl group having 3 to 5 carbon atoms, such as an isopropyl group, an isobutyl group, and a t-butyl group. The alkyl group may have a substituent such as a hydroxyl group.

n is an integer of 0 or more, which represents the number of substituents. For example, n is preferably 0 to 4, and more preferably 0.

Examples of the divalent linking group represented by A include an alkylene group, a cycloalkylene group, an ester bond, an amide bond, an ether bond, a urethane bond, a urea bond, and combinations thereof. As the alkylene group, an alkylene group having 1 to 10 carbon atoms is preferable, an alkylene group having 1 to 5 carbon atoms is more preferable, and examples thereof include a methylene group, an ethylene group, and a propylene group.

In one aspect of the present invention, A is preferably a single bond or an alkylene group.

Examples of a monocycle including —O—C(=O)—O—, which is represented by Z, include a 5- to 7-membered ring having nA of 2 to 4, in the cyclic carbonic acid ester represented by the following General Formula (a), and the monocycle is preferably a 5-membered ring or a 6-membered ring ($n_A$=2 or 3), and more preferably a 5-membered ring ($n_A$=2).

Examples of a polycycle including —O—C(=O)—O—, which is represented by Z, include a structure in which a fused ring is formed by cyclic carbonic acid ester represented by the following General Formula (a) together with one or two more other ring structures or a structure in which a spiro ring is formed. "Other ring structures" capable of forming a fused ring or a spiro ring may be an alicyclic hydrocarbon group, may be an aromatic hydrocarbon group, or may be a heterocycle.

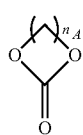

(a)

The monomer corresponding to the repeating unit represented by General Formula (A-1) can be synthesized by, for example, the method known in the related art described in Tetrahedron Letters, Vol. 27, No. 32 p. 3741 (1986), Organic Letters, Vol. 4, No. 15, p. 2561 (2002), or the like.

The resin (B) may include one kind or two or more kinds of the repeating units represented by General Formula (A-1).

In the resin (B), the content of the repeating unit having a cyclic carbonic acid ester structure (preferably the repeating unit represented by General Formula (A-1)) is preferably 3% to 80% by mole, more preferably 3% to 60% by mole, particularly preferably 3% to 30% by mole, and most preferably 10% to 15% by mole, with respect to all the repeating units constituting the resin (B). By setting the content to be within such the range, developability, low defects, low line width roughness (LWR), low post-exposure bake (PEB) temperature dependence, profiles, and the like as a resist can be improved.

Specific examples of the repeating unit represented by General Formula (A-1) are shown below, but the present invention is not limited thereto.

Moreover, $R_A^1$ in the following specific examples has the same definition as $R_A^1$ in General Formula (A-1).

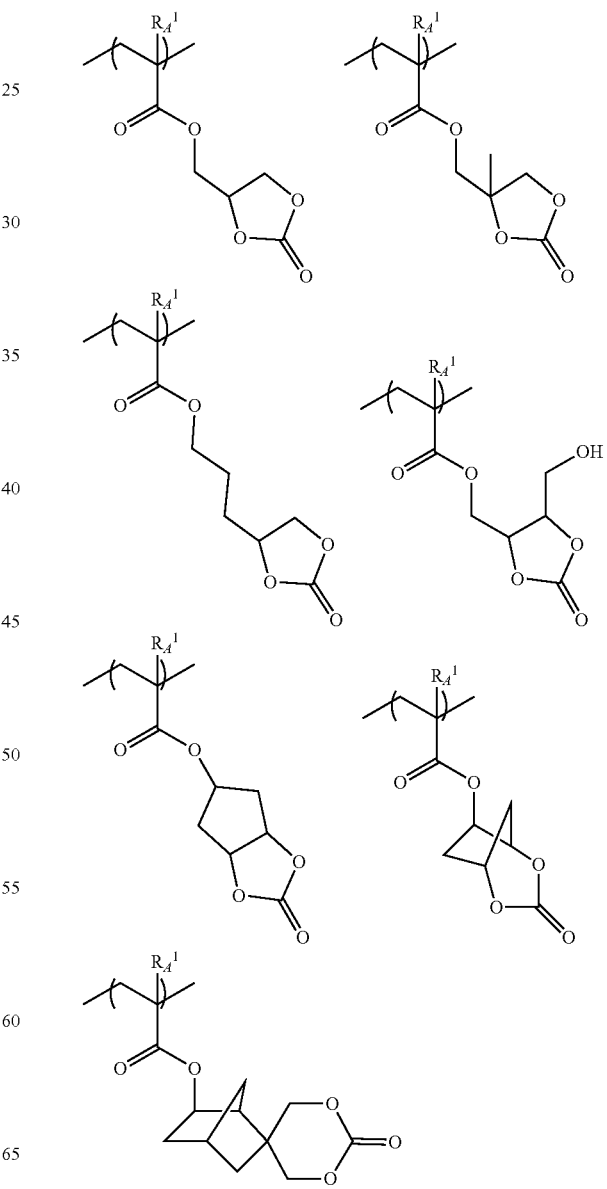

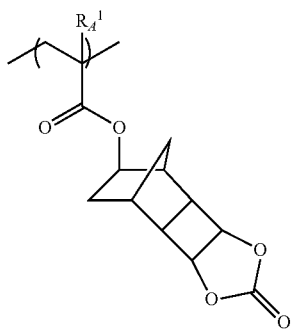

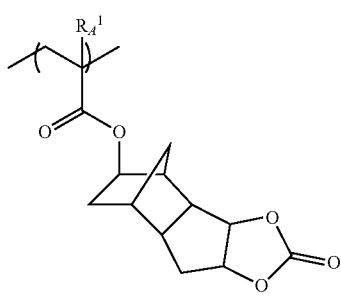

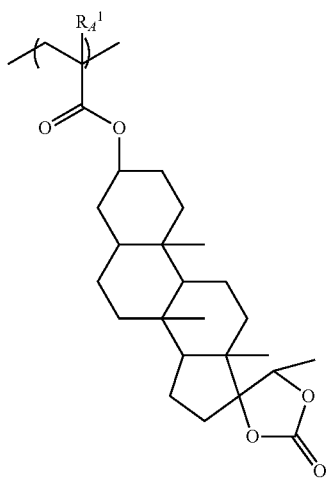

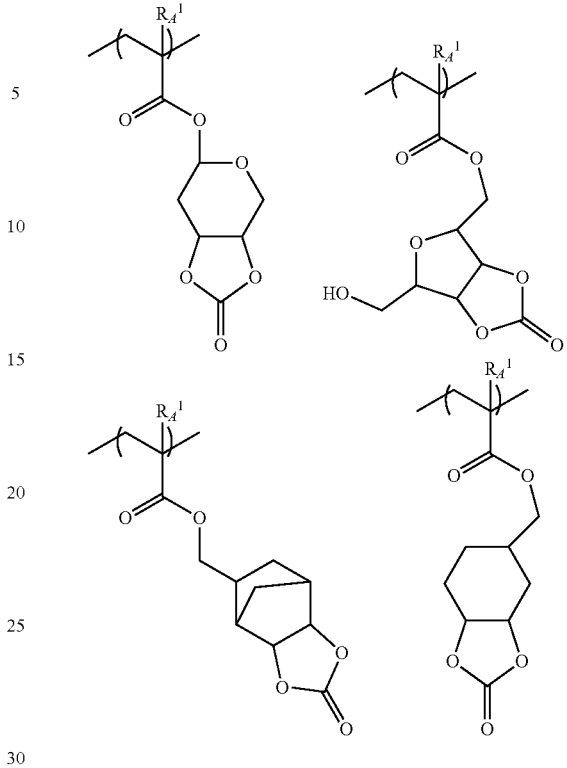

The resin (B) may have a repeating unit having a hydroxyl group or a cyano group. Examples of such the repeating unit include the repeating units described in paragraphs [0081] to [0084] of JP2014-098921A.

Furthermore, the resin (B) may have a repeating unit having an acid group. Examples of the acid group include a carboxyl group, a sulfonamido group, a sulfonylimido group, a bissulfonylimido group, and an aliphatic alcohol group with the α-position being substituted with an electron withdrawing group (for example, a hexafluoroisopropanol group). Examples of the repeating unit having an acid group include the repeating units described in paragraphs [0085] and [0086] of JP2014-098921A.

Moreover, the resin (B) can have a repeating unit which has an alicyclic hydrocarbon structure not having a polar group (for example, an acid group, a hydroxyl group, and a cyano group), and does not exhibit acid decomposability. Examples of such a repeating unit include the repeating units described in paragraphs [0114] to [0123] of JP2014-106299A.

Furthermore, the resin (B) may include the repeating units described in, for example, paragraphs [0045] to [0065] of JP2009-258586A.

In addition to the repeating structural units, the resin (B) used in the method of the present invention can have a variety of repeating structural units for the purpose of adjusting dry etching resistance or suitability for a standard developer, adhesiveness to a substrate, and a resist profile, and in addition, resolving power, heat resistance, sensitivity, and the like, which are characteristics generally required for the resist. Examples of such repeating structural units include, but are not limited to, repeating structural units corresponding to the following monomers.

Thus, it becomes possible to perform fine adjustments to performance required for the resin (B) used in the method of the present invention, in particular, (1) solubility with

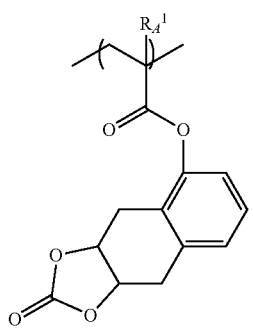 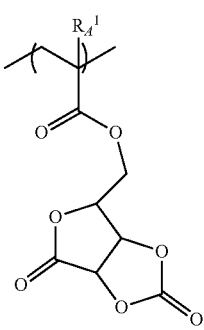

respect to a coating solvent, (2) film forming properties (glass transition point), (3) alkali developability, (4) film reduction (selection of hydrophilic, hydrophobic, or alkali-soluble groups), (5) adhesiveness of an unexposed area to a substrate, (6) dry etching resistance, and the like.

Examples of such a monomer include a compound having one addition-polymerizable unsaturated bond, selected from acrylic acid esters, methacrylic acid esters, acrylamides, methacrylamides, allyl compounds, vinyl ethers, vinyl esters, and the like.

In addition to these, an addition-polymerizable unsaturated compound that is copolymerizable with the monomers corresponding to various repeating structural units as described above may be copolymerized.

In the resin (B), the molar ratio of each repeating structural unit content is appropriately set in order to adjust dry etching resistance or suitability for a standard developer, adhesiveness to a substrate, and a resist profile of the resist, and in addition, resolving power, heat resistance, sensitivity, and the like, each of which is performance generally required for the resist.

In a case where the composition of embodiment of the present invention is for ArF exposure, it is preferable that the resin (B) does not substantially have an aromatic group in terms of transparency to ArF light. More specifically, the proportion of repeating units having an aromatic group in all the repeating units of the resin (B) is preferably 5% by mole or less, and more preferably 3% by mole or less, and ideally 0% by mole of all the repeating units, that is, it is even more preferable that the resin (B) does not have a repeating unit having an aromatic group. Further, it is preferable that the resin (B) has a monocyclic or polycyclic alicyclic hydrocarbon structure.

The resin (B) is preferably a resin in which all the repeating units are constituted with (meth)acrylate-based repeating units. In this case, any of a resin in which all of the repeating units are methacrylate-based repeating units, a resin in which all of the repeating units are acrylate-based repeating units, and a resin in which all of the repeating units are methacrylate-based repeating units and acrylate-based repeating units can be used, but it is preferable that the acrylate-based repeating units account for 50% by mole or less of all of the repeating units.

In a case where the composition of the embodiment of the present invention is for KrF exposure, EB exposure, or EUV exposure, it is preferable that the resin (B) has an aromatic group. It is more preferable that the resin (B) includes a repeating unit containing a phenolic hydroxyl group, and examples of the repeating unit containing a phenolic hydroxyl group include a hydroxystyrene repeating unit and a hydroxystyrene (meth)acrylate repeating unit.

The resin (B) may be any of a random polymer, a block polymer, and a graft polymer.

The resin (B) can be synthesized in accordance with an ordinary method (for example, radical polymerization). Examples of the general synthesis method include a bulk polymerization method in which polymerization is carried out by dissolving monomer species and an initiator in a solvent and heating the solution, a dropwise addition polymerization method in which a solution of monomer species and an initiator is added dropwise to a heating solvent for 1 to 10 hours, with the dropwise addition polymerization method being preferable. In the dropwise addition polymerization method, a part of monomer species may be introduced into a polymerization container in advance. By such introduction, a copolymer having a uniform compositional ratio from the initiation of polymerization to the completion of polymerization can be obtained, and the solubility in a developer becomes uniform. For example, in the present invention, it is preferable to perform dropwise addition polymerization in a state where at least one of a monomer having an Si atom or a monomer having an acid-decomposable group is introduced into a polymerization container in advance. Examples of the reaction solvent include ethers such as tetrahydrofuran, 1,4-dioxane, and diisopropyl ether, ketones such as methyl ethyl ketone and methyl isobutyl ketone, ester solvents such as ethyl acetate, amide solvents such as dimethyl formamide and dimethyl acetamide, and a solvent which dissolves the composition of embodiment of the present invention, such as propylene glycol monomethyl ether acetate, propylene glycol monomethyl ether, and cyclohexanone, which will be described later. It is more preferable to perform polymerization using the same solvent as the solvent used in the composition of embodiment of the present invention. Thus, generation of the particles during storage can be suppressed.

It is preferable that the polymerization reaction is carried out in an inert gas atmosphere such as nitrogen and argon. As the polymerization initiator, commercially available radical initiators (an azo-based initiator, a peroxide, or the like) are used to initiate the polymerization. As the radical initiator, an azo-based initiator is preferable, and the azo-based initiator having an ester group, a cyano group, or a carboxyl group is preferable. Preferred examples of the initiator include azobisisobutyronitrile, azobisdimethylvaleronitrile, and dimethyl 2,2'-azobis(2-methyl propionate). The initiator is added or added in portionwise, as desired, a desired polymer is recovered after the reaction is completed, the reaction mixture is poured into a solvent, and then a method such as powder or solid recovery is used. The concentration of the solid of the reaction solution is 5% to 50% by mass, and preferably 10% to 30% by mass. The reaction temperature is normally 10° C. to 150° C., preferably 30° C. to 120° C., and more preferably 60° C. to 100° C.

The weight-average molecular weight of the resin (B) is preferably 1,000 to 200,000, more preferably 2,000 to 20,000, still more preferably 3,000 to 15,000, and particularly preferably 3,000 to 11,000. By setting the weight-average molecular weight to 1,000 to 200,000, it is possible to prevent the deterioration of heat resistance or dry etching resistance, and also prevent the deterioration of film forming properties due to deteriorated developability or increased viscosity.

The dispersity (molecular weight distribution) is usually 1.0 to 3.0, and the dispersity in the range of preferably 1.0 to 2.6, more preferably 1.0 to 2.0, and particularly preferably 1.1 to 2.0 is used. As the molecular weight distribution is smaller, the resolution and the resist shape are better, the side wall of the resist pattern is smoother, and the roughness is better.

In the present invention, the resin (B) may be used alone or in combination of two or more kinds thereof.

In a case where a plurality of the resins (B) are used in combination, the Eth sensitivity of the acid-decomposable repeating unit in the resin (B) is a weighted average of the Eth sensitivities of the respective acid-decomposable repeating units of the respective acid-decomposable resins, based on the weighted value of the masses of the respective acid-decomposable resins. In other words, the Eth sensitivity of the acid-decomposable repeating unit is a sum of values obtained by multiplying the Eth sensitivities of the acid-decomposable repeating units of the respective acid-decomposable resins by the mass fractions of the respective acid-decomposable resins with respect to the total mass of the acid-decomposable resins.

In a case where the composition of the embodiment of the present invention contains an acid-decomposable resin having an Eth sensitivity of the acid-decomposable repeating unit of 5.64 or less and an acid-decomposable resin having an Eth sensitivity of the acid-decomposable repeating unit of more than 5.64 as the resin (B), it is preferable that the content ratio of the acid-decomposable resin having an Eth sensitivity of the acid-decomposable repeating unit of 5.64 or less with respect to the total amount of the acid-decomposable resin is larger than the content ratio of the acid-decomposable resin having an Eth sensitivity of the acid-decomposable repeating unit of acid-decomposable resin having an Eth sensitivity of the acid-decomposable repeating unit of more than 5.64 with respect to the total amount of the acid-decomposable resin.

The content of the resin (B) in the total solid content of the composition of the embodiment of the present invention is 20% by mass or more. Among those, the content is preferably 40% by mass or more, more preferably 60% by mass or more, and still more preferably 80% by mass or more. The upper limit is not particularly limited, but is preferably 99% by mass or less, more preferably 97% by mass or less, and still more preferably 95% by mass or less.

<Hydrophobic Resin>

The composition of embodiment of the present invention may contain a hydrophobic resin (hereinafter also referred to as a "hydrophobic resin (D)" or simply a "resin (D)"). Further, the hydrophobic resin (D) is preferably different from the acid-decomposable resin.

Although the hydrophobic resin (D) is preferably designed to be unevenly distributed on an interface as described above, it does not necessarily have to have a hydrophilic group in its molecule as different from the surfactant, and does not need to contribute to uniform mixing of polar/nonpolar materials.

Examples of the effect of addition of the hydrophobic resin include control of the static/dynamic contact angle of the resist film surface with respect to water, improvement of the immersion liquid tracking properties, and suppression of out gas.

The hydrophobic resin (D) preferably has any one of a "fluorine atom", a "silicon atom", and a "$CH_3$ partial structure which is contained in a side chain moiety of a resin" from the viewpoint of uneven distribution on the film surface layer, and more preferably has two or more kinds.

In a case where hydrophobic resin (D) includes a fluorine atom and/or a silicon atom, the fluorine atom and/or the silicon atom in the hydrophobic resin (D) may be contained in the main chain or the side chain of the resin.

In a case where the hydrophobic resin (D) includes a fluorine atom, it is preferably a resin having an alkyl group having a fluorine atom, a cycloalkyl group having a fluorine atom, or an aryl group having a fluorine atom, as a partial structure having a fluorine atom.

The alkyl group having a fluorine atom (preferably having 1 to 10 carbon atoms, and more preferably having 1 to 4 carbon atoms) is a linear or branched alkyl group in which at least one hydrogen atom is substituted with a fluorine atom, and may further have a substituent other than a fluorine atom.

The cycloalkyl group having a fluorine atom and the aryl group having a fluorine atom are a cycloalkyl group in which at least one hydrogen atom is substituted with a fluorine atom, and an aryl group having a fluorine atom, respectively, and they may further have a substituent other than a fluorine atom.

Preferred examples of the alkyl group having a fluorine atom, the cycloalkyl group having a fluorine atom, and the aryl group having a fluorine atom include groups represented by General Formulae (F2) to (F4), but the present invention is not limited thereto.

(F2)

(F3)

(F4)

In General Formulae (F2) to (F4), $R_{57}$ to $R_{68}$ each independently represent a hydrogen atom, a fluorine atom, or an (linear or branched) alkyl group, provided that at least one of $R_{57}$, ..., or $R_{61}$, at least one of $R_{62}$, ..., or $R_{64}$, and at least one of $R_{65}$, ..., or $R_{68}$ each independently represent a fluorine atom or an alkyl group (preferably having 1 to 4 carbon atoms) in which at least one hydrogen atom is substituted with a fluorine atom.

It is preferable that all of $R_{57}$ to $R_{61}$, and $R_{65}$ to $R_{67}$ are fluorine atoms. $R_{62}$, $R_{63}$, and $R_{68}$ are each preferably an alkyl group (preferably having 1 to 4 carbon atoms) in which at least one hydrogen atom is substituted with a fluorine atom, and more preferably a perfluoroalkyl group having 1 to 4 carbon atoms. $R_{62}$ and $R_{63}$ may be bonded to each other to form a ring.

The hydrophobic resin (D) may contain a silicon atom. The hydrophobic resin is preferably a resin having an alkylsilyl structure (preferably a trialkylsilyl group) or a cyclic siloxane structure as the partial structure having a silicon atom.

Examples of the repeating unit having a fluorine atom or a silicon atom include those exemplified in [0519] of US2012/0251948A1.

Moreover, it is also preferable that the hydrophobic resin (D) includes a $CH_3$ partial structure in the side chain moiety as described above.

Here, the $CH_3$ partial structure contained in the side chain moiety (hereinafter also simply referred to as a "side chain $CH_3$ partial structure") in the hydrophobic resin (D) includes a $CH_3$ partial structure contained in an ethyl group, a propyl group, and the like.

On the other hand, a methyl group (for example, an α-methyl group in the repeating unit having a methacrylic acid structure) bonded directly to the main chain of the hydrophobic resin (D) makes only a small contribution of uneven distribution to the surface of the hydrophobic resin (D) due to the effect of the main chain, and it is therefore not included in the CH$_3$ partial structure in the present invention.

More specifically, in a case where the hydrophobic resin (D) includes a repeating unit derived from a monomer having a polymerizable site with a carbon-carbon double bond, such as a repeating unit represented by General Formula (M), and in addition, R$_{11}$ to R$_{14}$ are each CH$_3$ "itself", such the CH$_3$ is not included in the CH$_3$ partial structure contained in the side chain moiety in the present invention.

On the other hand, a CH$_3$ partial structure which is present via a certain atom from a C—C main chain corresponds to the CH$_3$ partial structure in the present invention. For example, in a case where R$_{11}$ is an ethyl group (CH$_2$CH$_3$), the hydrophobic resin (D) has "one" CH$_3$ partial structure in the present invention.

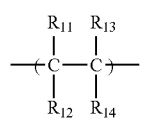

(M)

In General Formula (M),

R$_{11}$ to R$_{14}$ each independently represent a side chain moiety.

Examples of R$_{11}$ to R$_{14}$ at the side chain moiety include a hydrogen atom and a monovalent organic group.

Examples of the monovalent organic group for R$_{11}$ to R$_{14}$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group, and these groups may further have a substituent.

The hydrophobic resin (D) is preferably a resin including a repeating unit having the CH$_3$ partial structure in the side chain moiety thereof. Further, the hydrophobic resin more preferably has, as such a repeating unit, at least one repeating unit (x) selected from a repeating unit represented by General Formula (II) or a repeating unit represented by General Formula (III).

Hereinafter, the repeating unit represented by General Formula (II) will be described in detail.

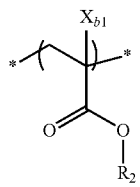

(II)

In General Formula (II), X$_{b1}$ represents a hydrogen atom, an alkyl group, a cyano group, or a halogen atom, and R$_2$ represents an organic group which has one or more CH$_3$ partial structures and is stable against an acid. Here, more specifically, the organic group which is stable against an acid is preferably an organic group which does not have an "acid-decomposable group" described with respect to the resin (B).

The alkyl group of X$_{b1}$ is preferably an alkyl group having 1 to 4 carbon atoms, and examples thereof include a methyl group, an ethyl group, a propyl group, a hydroxymethyl group, and a trifluoromethyl group, with the methyl group being preferable.

X$_{b1}$ is preferably a hydrogen atom or a methyl group.

Examples of R$_2$ include an alkyl group, a cycloalkyl group, an alkenyl group, a cycloalkenyl group, an aryl group, and an aralkyl group, each of which has one or more CH$_3$ partial structures. Each of the cycloalkyl group, the alkenyl group, the cycloalkenyl group, the aryl group and the aralkyl group may further have an alkyl group as a substituent.

R$_2$ is preferably an alkyl group or an alkyl-substituted cycloalkyl group, each of which has one or more CH$_3$ partial structures.

The number of the CH$_3$ partial structures contained in the organic group which has one or more CH$_3$ partial structures and is stable against an acid as R$_2$ is preferably from 2 to 10, and more preferably from 2 to 8.

Preferred specific examples of the repeating unit represented by General Formula (II) are as follow. The present invention is not limited thereto.

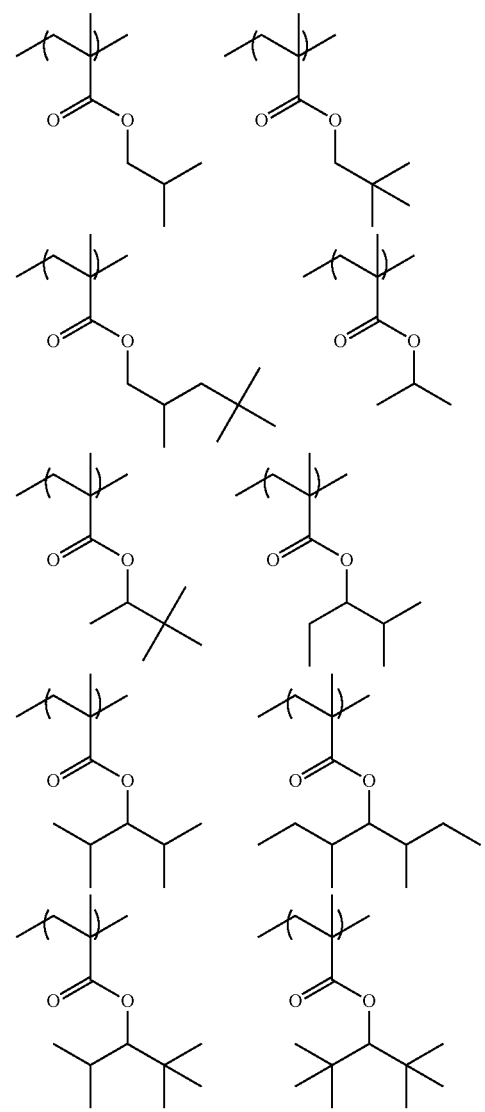

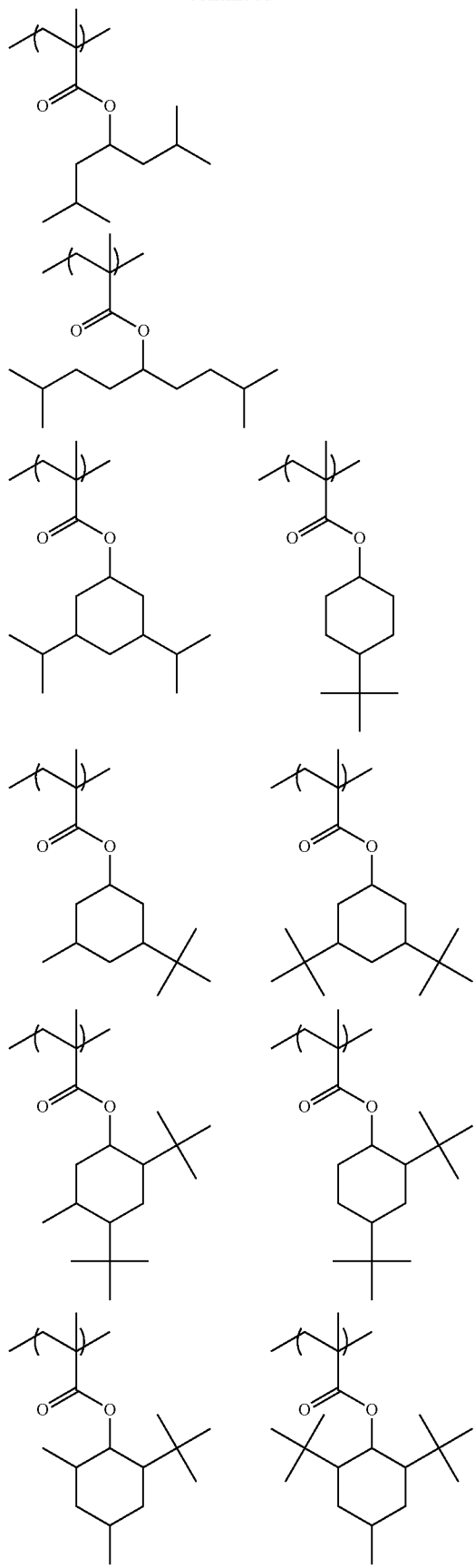
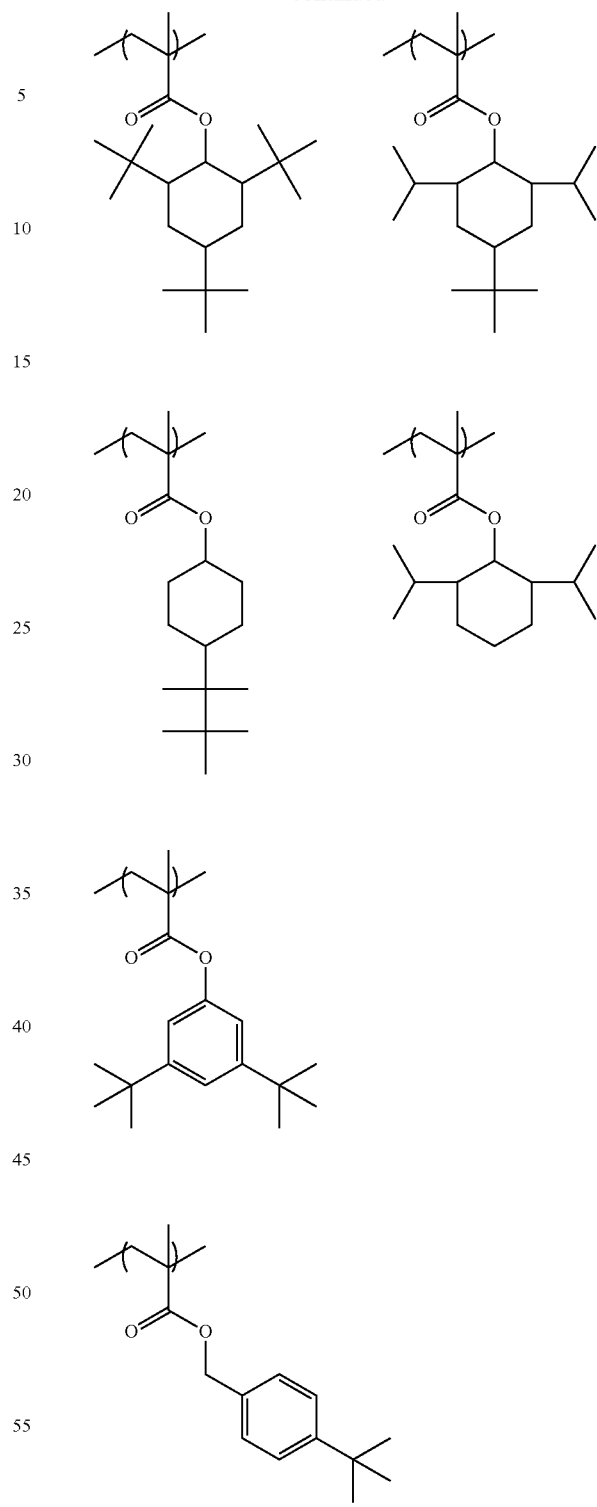

The repeating unit represented by General Formula (II) is preferably a repeating unit which is stable against an acid (non-acid-decomposable), and specifically, it is preferably a repeating unit not having a group capable of decomposing by the action of an acid to generate a polar group.

Hereinafter, the repeating unit represented by General Formula (III) will be described in detail.

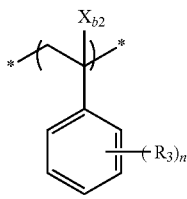
(III)

In General Formula (III), $X_{b2}$ represents a hydrogen atom, an alkyl group, a cyano group, or a halogen atom, $R_3$ represents an organic group which has one or more $CH_3$ partial structures and is stable against an acid, and n represents an integer of 1 to 5.

The alkyl group of $X_{b2}$ is preferably an alkyl group having 1 to 4 carbon atoms, and examples thereof include a methyl group, an ethyl group, a propyl group, a hydroxymethyl group, and a trifluoromethyl group, but a hydrogen atom is preferable.

$X_{b2}$ is preferably a hydrogen atom.

Since $R_3$ is an organic group stable against an acid, more specifically, $R_3$ is preferably an organic group which does not have the "acid-decomposable group" described for the resin (B).

Examples of $R_3$ include an alkyl group having one or more $CH_3$ partial structures.

The number of the $CH_3$ partial structures contained in the organic group which has one or more $CH_3$ partial structures and is stable against an acid as $R_3$ is preferably from 1 to 10, more preferably from 1 to 8, and still more preferably from 1 to 4.

n represents an integer of 1 to 5, more preferably 1 to 3, and still more preferably 1 or 2.

Preferred specific examples of the repeating unit represented by General Formula (III) are as follow. The present invention is not limited thereto.

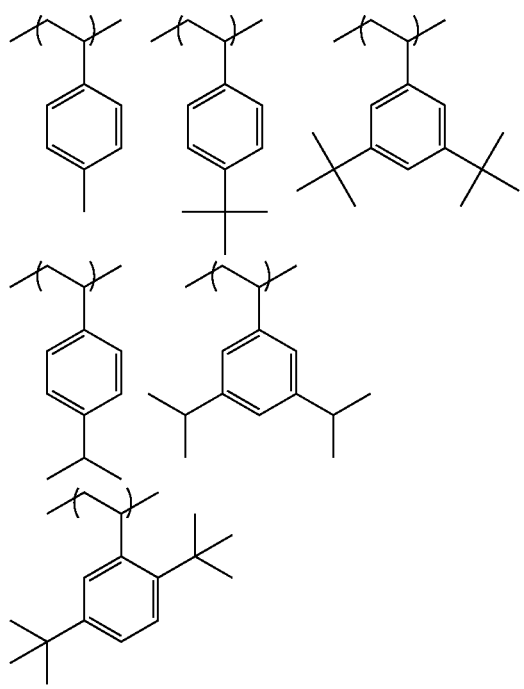

The repeating unit represented by General Formula (III) is preferably a repeating unit which is stable against an acid (non-acid-decomposable), and specifically, it is preferably a repeating unit which does not have "a group that decomposes by the action of an acid to generate a polar group".

In a case where the hydrophobic resin (D) includes a $CH_3$ partial structure in the side chain moiety thereof, and in particular, it has neither a fluorine atom nor a silicon atom, the content of at least one repeating unit (x) of the repeating unit represented by General Formula (II) or the repeating unit represented by General Formula (III) is preferably 90% by mole or more, and more preferably 95% by mole or more, with respect to all the repeating units of the hydrophobic resin (D). Further, the content is usually 100% by mole or less with respect to all the repeating units of the hydrophobic resin (D).

By incorporating at least one repeating unit (x) of the repeating unit represented by General Formula (II) or the repeating unit represented by General Formula (III) in a proportion of 90% by mole or more with respect to all the repeating units of the hydrophobic resin (D) into the hydrophobic resin (D), the surface free energy of the hydrophobic resin (D) is increased. As a result, it is difficult for the hydrophobic resin (D) to be unevenly distributed on the surface of the resist film and the static/dynamic contact angle of the resist film with respect to water can be securely increased, thereby enhancing the immersion liquid tracking properties.

In addition, in a case where the hydrophobic resin (D) contains (i) a fluorine atom and/or a silicon atom or (ii) a $CH_3$ partial structure in the side chain moiety, the hydrophobic resin may have at least one group selected from the following groups (x) to (z):
(x) an acid group,
(y) a group having a lactone structure, an acid anhydride group, or an acid imido group, and
(z) a group that decomposes by the action of an acid.

Examples of the acid group (x) include a phenolic hydroxyl group, a carboxylic acid group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

Preferred examples of the acid group include a fluorinated alcohol group (preferably a hexafluoroisopropanol group), a sulfonimido group, and a bis(alkylcarbonyl)methylene group.

Examples of the repeating unit having an acid group (x) include a repeating unit in which the acid group is directly bonded to the main chain of the resin, such as a repeating unit by an acrylic acid or a methacrylic acid, and a repeating unit in which the acid group is bonded to the main chain of the resin through a linking group, and the acid group may also be introduced into the polymer chain terminal by using a polymerization initiator or chain transfer agent containing an acid group during the polymerization. All of these cases are preferable. The repeating unit having an acid group (x) may have at least one of a fluorine atom or a silicon atom.

The content of the repeating units having an acid group (x) is preferably 1% to 50% by mole, more preferably 3% to 35% by mole, and still more preferably 5% to 20% by mole, with respect to all the repeating units in the hydrophobic resin (D).

Specific examples of the repeating unit having an acid group (x) are shown below, but the present invention is not limited thereto. In the formulae, $R_x$ represents a hydrogen atom, $CH_3$, $CF_3$, or $CH_2OH$.
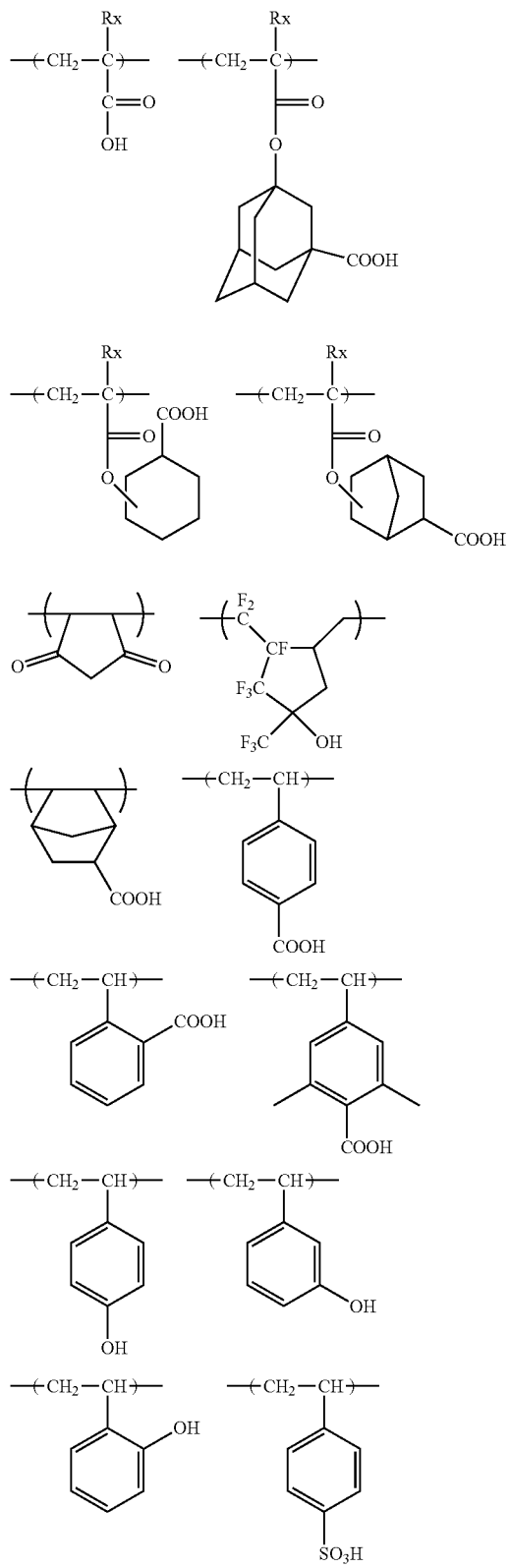
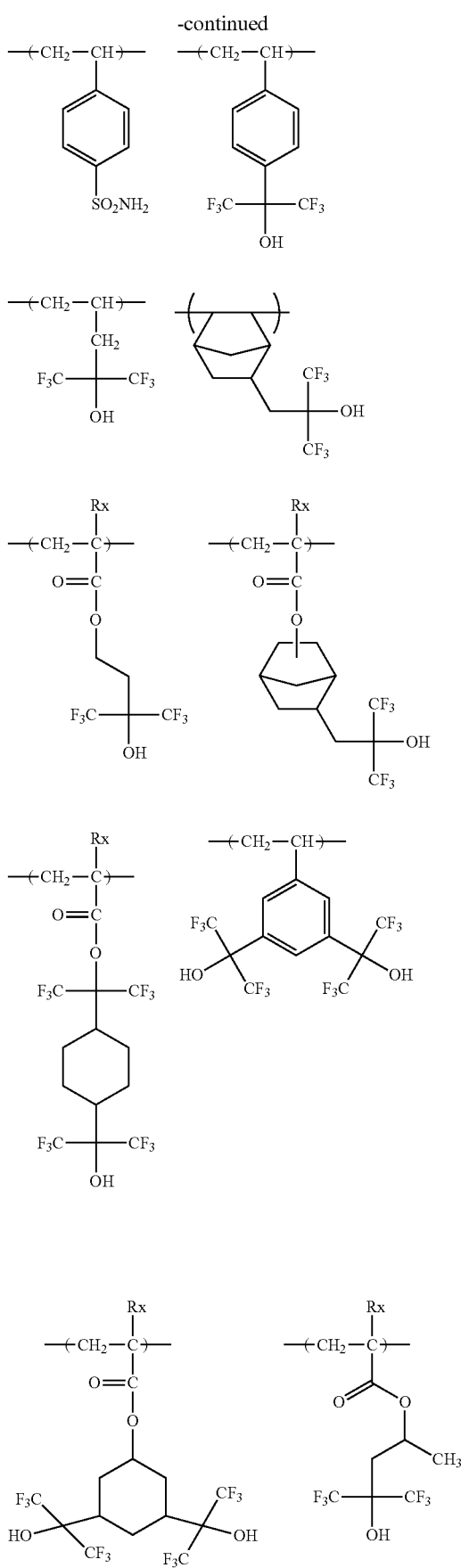

-continued

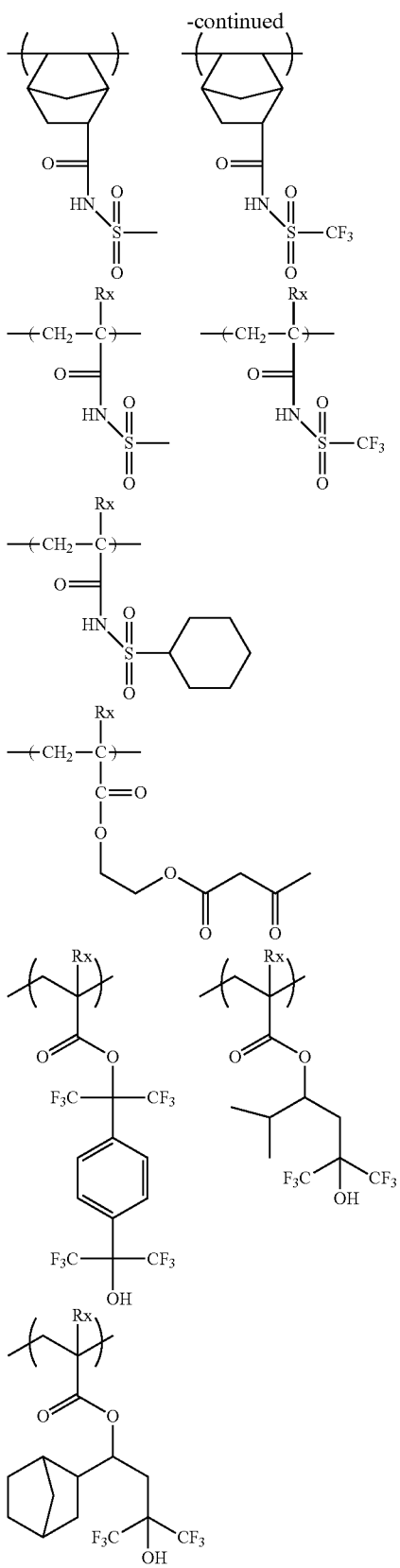

As the group having a lactone structure, the acid anhydride group, or the acid imido group (y), a group having a lactone structure is particularly preferable.

The repeating unit including the group is, for example, a repeating unit in which the group is directly bonded to the main chain of the resin, such as a repeating unit by an acrylic ester or a methacrylic ester. This repeating unit may be a repeating unit in which the group is bonded to the main chain of the resin through a linking group. Alternatively this repeating unit may be introduced into the terminal of the resin by using a polymerization initiator or chain transfer agent containing the group during the polymerization.

Examples of the repeating unit containing a group having a lactone structure include the same ones as the repeating unit having a lactone structure as described earlier in the section of the resin (B).

The content of the repeating units having a group having a lactone structure, an acid anhydride group, or an acid imido group is preferably 1% to 100% by mole, more preferably 3% to 98% by mole, and still more preferably 5% to 95% by mole, with respect to all the repeating units in the hydrophobic resin (D).

With respect to the hydrophobic resin (D), examples of the repeating unit having a group (z) that decomposes by the action of an acid include the same ones as the repeating units having an acid-decomposable group, as exemplified in the resin (B). The repeating unit having a group (z) that decomposes by the action of an acid may have at least one of a fluorine atom or a silicon atom. With respect to the hydrophobic resin (D), the content of the repeating units having a group (z) that decomposes by the action of an acid is preferably 1% to 80% by mole, more preferably 10% to 80% by mole, and still more preferably 20% to 60% by mole, with respect to all the repeating units in the hydrophobic resin (D).

The hydrophobic resin (D) may have a repeating unit other than the above-mentioned repeating units.

The repeating unit containing a fluorine atom is preferably in the amount of 10% to 100% by mole, and more preferably in the amount of 30% to 100% by mole, with respect to all the repeating units included in the hydrophobic resin (D). Further, the repeating unit containing a silicon atom is preferably in the amount of 10% to 100% by mole, and more preferably in the amount of 20% to 100% by mole, with respect to all the repeating units in the hydrophobic resin (D).

On the other hand, in particular, in a case where the hydrophobic resin (D) includes a $CH_3$ partial structure in the side chain moiety thereof, it is also preferable that the hydrophobic resin (D) has a form substantially not containing a fluorine atom and a silicon atom. In addition, it is preferable that the hydrophobic resin (D) is substantially composed only of repeating units which are composed only of atoms selected from a carbon atom, an oxygen atom, a hydrogen atom, a nitrogen atom, and a sulfur atom.

The weight-average molecular weight in terms of standard polystyrene, of the hydrophobic resin (D), is preferably 1,000 to 100,000, and more preferably 1,000 to 50,000. Furthermore, the hydrophobic resin (D) may be used singly or in combination of two or more kinds thereof.

The content of the hydrophobic resin (D) in the composition is preferably 0.01% to 10% by mass, and more preferably 0.05% to 8% by mass, with respect to the total solid contents of the composition of embodiment of the present invention.

It is natural that the hydrophobic resin (D) contains a small amount of impurities such as metals, but the amount of residual monomers and oligomer components in the hydrophobic resin is preferably 0.01% to 5% by mass, and more preferably 0.01% to 3% by mass. Further, the molecular weight distribution (Mw/Mn, also referred to as a dispersity) is preferably in a range of 1 to 5, and more preferably in a range of 1 to 3.

As the hydrophobic resin (D), various commercial products can also be used, or the resin can be synthesized by an ordinary method (for example, radical polymerization).

<Acid Diffusion Control Agent>

The composition of embodiment of the present invention preferably contains an acid diffusion control agent. The acid diffusion control agent acts as a quencher that inhibits a reaction of the acid-decomposable resin in the unexposed area by excessive generated acids by trapping the acids generated from a photoacid generator or the like upon exposure. As the acid diffusion control agent, a basic compound, a low-molecular-weight compound which has a nitrogen atom and a group that leaves by the action of an acid, a basic compound whose basicity is reduced or lost upon irradiation with actinic rays or radiation, or an onium salt which becomes a relatively weak acid with respect to the photoacid generator upon irradiation with actinic rays or radiation can be used.

Preferred examples of the basic compound include compounds having structures represented by Formulae (A) to (E).

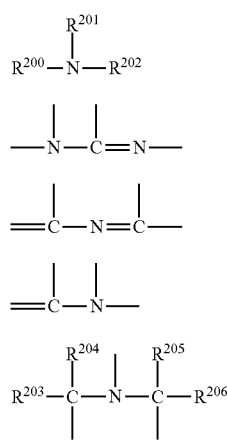

In General Formulae (A) and (E), $R^{200}$, $R^{201}$, and $R^{202}$ may be the same as or different from each other, and each represent a hydrogen atom, an alkyl group (preferably having 1 to 20 carbon atoms), a cycloalkyl group (preferably having 3 to 20 carbon atoms), or an aryl group (having 6 to 20 carbon atoms), and $R^{201}$ and $R^{202}$ may be bonded to each other to form a ring.

$R^{203}$, $R^{204}$, $R^{205}$, and $R^{206}$ may be the same as or different from each other, and each represent an alkyl group having 1 to 20 carbon atoms.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl groups in General Formulae (A) and (E) are more preferably unsubstituted.

Preferred examples of the compound include guanidine, aminopyrrolidine, pyrazole, pyrazoline, piperazine, aminomorpholine, aminoalkylmorpholine, and piperidine. More preferred examples of the compound include a compound having an imidazole structure, a diazabicyclo structure, an onium hydroxide structure, an onium carboxylate structure, a trialkylamine structure, an aniline structure, or a pyridine structure; an alkylamine derivative having a hydroxyl group and/or an ether bond; and an aniline derivative having a hydroxyl group and/or an ether bond.

Specific preferred examples of the compound include the compounds exemplified in [0379] of US2012/0219913A1.

Preferred examples of the basic compound include an amine compound having a phenoxy group, an ammonium salt compound having a phenoxy group, an amine compound containing a sulfonic ester group, and an ammonium salt compound having a sulfonic ester group.

These basic compounds may be used singly or in combination of two or more kinds thereof.

The composition of embodiment of the present invention may or may not contain a basic compound, but in a case where it contains the basic compound, the content of the basic compound is usually 0.001% to 10% by mass, and preferably 0.01% to 5% by mass, with respect to the solid content of the composition.

The ratio of the photoacid generator to the basic compound to be used in the composition is preferably photoacid generator/basic compound (molar ratio)=2.5 to 300, more preferably 5.0 to 200, and still more preferably 7.0 to 150.

The low-molecular-weight compound (hereinafter also referred to as a "compound (C)") which has a nitrogen atom and a group that leaves by the action of an acid is preferably an amine derivative having a group that leaves by the action of an acid on a nitrogen atom.

As the group that leaves by the action of an acid, an acetal group, a carbonate group, a carbamate group, a tertiary ester group, a tertiary hydroxyl group, or a hemiaminal ether group is preferable, and a carbamate group or a hemiaminal ether group is particularly preferable.

The molecular weight of the compound (C) is preferably 100 to 1,000, more preferably 100 to 700, and particularly preferably 100 to 500.

The compound (C) may have a carbamate group having a protecting group on a nitrogen atom. The protecting group constituting the carbamate group can be represented by General Formula (d-1).

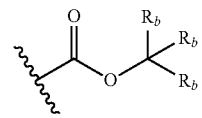

(d-1)

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). $R_b$'s may be bonded to each other to form a ring.

The alkyl group, the cycloalkyl group, the aryl group, or the aralkyl group represented by $R_b$ may be substituted with a functional group such as a hydroxyl group, a cyano group, an amino group, a pyrrolidino group, a piperidino group, a morpholino group, and an oxo group, an alkoxy group, or a halogen atom. This is the same as for the alkoxyalkyl group represented by $R_b$.

$R_b$ is preferably a linear or branched alkyl group, a cycloalkyl group, or an aryl group, and more preferably a linear or branched alkyl group, or a cycloalkyl group.

Examples of the ring formed by the mutual bonding of two $R_b$'s include an alicyclic hydrocarbon group, an aromatic hydrocarbon group, a heterocyclic hydrocarbon group, and derivatives thereof.

Examples of the specific structure of the group represented by General Formula (d-1) include, but are not limited to, the structures disclosed in [0466] of US2012/0135348A1.

It is particularly preferable that the compound (C) has a structure represented by General Formula (6).

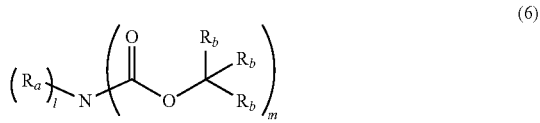

(6)

In General Formula (6), $R_a$ represents a hydrogen atom, an alkyl group, a cycloalkyl group, an aryl group, or an aralkyl group. In a case where l is 2, two $R_a$'s may be the same as or different from each other. Two $R_a$'s may be bonded to each other to form a heterocycle may be bonded to each other to form, together with a carbon atom to which they are bonded with the nitrogen atom in the formula. The heterocycle may include a heteroatom other than the nitrogen atom in the formula.

$R_b$ has the same definition as $R_b$ in General Formula (d-1), and preferred examples are also the same.

l represents an integer of 0 to 2, and m represents an integer of 1 to 3, satisfying l+m=3.

In General Formula (6), the alkyl group, the cycloalkyl group, the aryl group, and the aralkyl group as $R_a$ may be substituted with the same groups as the group mentioned above as a group which may be substituted in the alkyl group, the cycloalkyl group, the aryl group, and the aralkyl group as $R_b$.

Specific examples of the alkyl group, the cycloalkyl group, the aryl group, and the aralkyl group (such the alkyl group, a cycloalkyl group, an aryl group, and aralkyl group may be substituted with the groups as described above) of $R_a$ include the same groups as the specific examples as described above with respect to $R_b$.

Specific examples of the particularly preferred compound (C) in the present invention include, but are not limited to, the compounds disclosed in paragraph [0475] of US2012/0135348A1.

The compounds represented by General Formula (6) can be synthesized in accordance with JP2007-298569A, JP2009-199021 A, and the like.

In the present invention, the low-molecular-weight compound (C) having a group that leaves by the action of an acid on a nitrogen atom may be used singly or as a mixture of two or more kinds thereof.

The content of the compound (C) in the composition of embodiment of the present invention is preferably 0.001% to 20% by mass, more preferably 0.001% to 10% by mass, and still more preferably 0.01% to 5% by mass, with respect to the total solid content of the composition.

The basic compound whose basicity is reduced or lost upon irradiation with actinic rays or radiation (hereinafter also referred to as a "compound (PA)") is a compound which has a functional group with proton-accepting properties, and decomposes under irradiation with actinic rays or radiation to exhibit deterioration in proton-accepting properties, no proton-accepting properties, or a change from the proton-accepting properties to acidic properties.

The functional group with proton-accepting properties refers to a functional group having a group or an electron which is capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

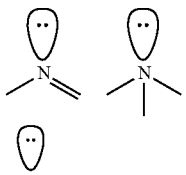

Unshared electron pair

Preferred examples of the partial structure of the functional group with proton-accepting properties include crown ether, azacrown ether, primary to tertiary amines, pyridine, imidazole, and pyrazine structures.

The compound (PA) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the functional group with proton-accepting properties, and specifically a decrease in the equilibrium constant at chemical equilibrium in a case where a proton adduct is generated from the compound (PA) having the functional group with proton-accepting properties and the proton.

The proton-accepting properties can be confirmed by carrying out pH measurement.

In the present invention, the acid dissociation constant pKa of the compound generated by the decomposition of the compound (PA) upon irradiation with actinic rays or radiation preferably satisfies pKa<−1, more preferably −13<pKa<−1, and still more preferably −13<pKa<−3.

The compound (PA) generates a compound represented by General Formula (PA-1), for example, as the proton adduct generated by decomposition upon irradiation with actinic rays or radiation. The compound represented by General Formula (PA-1) is a compound exhibiting deterioration in proton-accepting properties, no proton-accepting properties, or a change from the proton-accepting properties to acidic properties since the compound has a functional group with proton-accepting properties as well as an acidic group, as compared with the compound (PA).

$$Q\text{-}A\text{-}(X)_n\text{—}B\text{—}R \qquad (PA\text{-}1)$$

In General Formula (PA-1), Q represents —SO$_3$H, —CO$_2$H, or —W$_1$NHW$_2$R$_f$, in which R$_f$ represents an alkyl group (preferably having 1 to 20 carbon atoms), a cycloalkyl group (preferably having 3 to 20 carbon atoms), or an aryl group (preferably having 6 to 30 carbon atoms), and W$_1$ and W$_2$ each independently represent —SO$_2$— or —CO—.

A represents a single bond or a divalent linking group.
X represents —SO$_2$— or —CO—.
n is 0 or 1.

B represents a single bond, an oxygen atom, or —N(R$_x$)R$_y$—, in which R$_x$ represents a hydrogen atom or a monovalent organic group, and R$_y$ represents a single bond or a divalent organic group, provided that R$_x$ may be bonded to R$_y$ to form a ring or may be bonded to R to form a ring.

The compound (PA) is preferably an ionic compound. The functional group with proton-accepting properties may be included in an anionic moiety or a cationic moiety, but is preferably included in the anionic moiety.

Furthermore, in the present invention, compounds (PA) other than a compound capable of generating the compound represented by General Formula (PA-1) can also be appropriately selected. For example, a compound having a proton acceptor site at its cationic moiety may be used as an ionic compound. More specific examples thereof include a compound represented by General Formula (7).

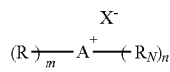

(7)

In the formula, A represents a sulfur atom or an iodine atom.

m represents 1 or 2 and n represents 1 or 2, provided that m+n=3 in a case where A is a sulfur atom and that m+n=2 in a case where A is an iodine atom.

R represents an aryl group.

R$_N$ represents an aryl group substituted with the functional group with proton-accepting properties, and X— represents a counter anion.

Specific examples of X— include the anions described in paragraphs [0149] to [0183] of JP2016-042199A.

Specific preferred examples of the aryl group of each of R and R$_N$ include a phenyl group.

Specific examples of the functional group with proton-accepting properties contained in R$_N$ are the same as those of the functional group with proton-accepting properties as described above in Formula (PA-1).

Specific examples of the ionic compounds having a proton acceptor site at a cationic moiety include the compounds exemplified in [0291] of US2011/0269072A1.

Furthermore, such compounds can be synthesized, for example, with reference to the methods described in JP2007-230913A, JP2009-122623A, and the like.

The compound (PA) may be used singly or in combination of two or more kinds thereof. The content of the compound (PA) is preferably 0.1% to 10% by mass, and more preferably 1% to 8% by mass, with respect to the total solid content of the composition.

In the composition of embodiment of the present invention, an onium salt which becomes a relatively weak acid with respect to the photoacid generator can be used as an acid diffusion control agent.

In a case of mixing the photoacid generator and the onium salt that generates an acid which is a relatively weak acid with respect to an acid generated from the photoacid generator, and then using the mixture, in a case where the acid generated from the photoacid generator upon irradiation with actinic rays or radiation collides with an onium salt having an unreacted weak acid anion, a weak acid is discharged by salt exchange, thereby generating an onium salt having a strong acid anion. In this process, the strong acid is exchanged with a weak acid having a lower catalytic ability, and therefore, the acid is deactivated in appearance, and thus, it is possible to carry out the control of acid diffusion.

As the onium salt which becomes a relatively weak acid with respect to the photoacid generator, compounds represented by General Formulae (d1-1) to (d1-3) are preferable.

(d1-1)

(d1-2)

(d1-3)

In the formulae, R$^{51}$ is a hydrocarbon group which may have a substituent, Z$^{2c}$ is a hydrocarbon group (provided that carbon adjacent to S is not substituted with a fluorine atom) having 1 to 30 carbon atoms, which may have a substituent, R$^{52}$ is an organic group, Y$^3$ is a linear, branched, or cyclic alkylene group or arylene group, Rf is a hydrocarbon group including a fluorine atom, and M$^+$'s are each independently a sulfonium or iodonium cation.

Preferred examples of the sulfonium cation or the iodonium cation represented by M$^+$ include the sulfonium cations exemplified for General Formula (ZI) and the iodonium cations exemplified for General Formula (ZII).

Preferred examples of the anionic moiety of the compound represented by General Formula (d1-1) include the structures exemplified in paragraph [0198] of JP2012-242799A. Preferred examples of the anionic moiety of the compound represented by General Formula (d1-2) include the structures exemplified in paragraph [0201] of JP2012-242799A. Preferred examples of the anionic moiety of the compound represented by General Formula (d1-3) include the structures exemplified in paragraphs [0209] and [0210] of JP2012-242799A.

The onium salt which becomes a relatively weak acid with respect to the photoacid generator may be a compound (C) (hereinafter also referred to as a "compound (CA)") having a cationic moiety and an anionic moiety in the same molecule, in which the cationic moiety and the anionic moiety are linked to each other through a covalent bond.

As the compound (CA), a compound represented by any one of General Formulae (C-1) to (C-3) is preferable.

(C-1)

(C-2)

(C-3)

In General Formulae (C-1) to (C-3), $R_1$, $R_2$, and $R_3$ represent a substituent having 1 or more carbon atoms.

$L_1$ represents a divalent linking group that links a cationic moiety with an anionic moiety, or a single bond.

—X— represents an anionic moiety selected from —COO—, —SO$_3$—, —SO$_2^-$, and —N$^-$—R$_4$. R$_4$ represents a monovalent substituent having a carbonyl group: —C(=O)—, a sulfonyl group: —S(=O)$_2$—, or a sulfinyl group: —S(=O)— at a site for linking to an adjacent N atom.

$R_1$, $R_2$, $R_3$, $R_4$, and $L_1$ may be bonded to one another to form a ring structure. Further, in (C-3), two of $R_1$ to $R_3$ may be bonded to each other to form a double bond with an N atom.

Examples of the substituent having 1 or more carbon atoms in $R_1$ to $R_3$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group, and preferably an alkyl group, a cycloalkyl group, and an aryl group.

Examples of $L_1$ as a divalent linking group include a linear or branched alkylene group, a cycloalkylene group, an arylene group, a carbonyl group, an ether bond, ester bond, amide bond, a urethane bond, a urea bond, and a group formed by a combination of two or more kinds of these groups. $L_1$ is more preferably an alkylene group, an arylene group, an ether bond, ester bond, and a group formed by a combination of two or more kinds of these groups.

Preferred examples of the compound represented by General Formula (C-1) include the compounds exemplified in paragraphs [0037] to [0039] of JP2013-006827A and paragraphs [0027] to [0029] of JP2013-008020A.

Preferred examples of the compound represented by General Formula (C-2) include the compounds exemplified in paragraphs [0012] and [0013] of JP2012-189977A.

Preferred examples of the compound represented by General Formula (C-3) include the compounds exemplified in paragraphs [0029] to [0031] of JP2012-252124A.

The content of the onium salt which becomes a relatively weak acid with respect to the photoacid generator is preferably 0.5% to 10.0% by mass, more preferably 0.5% to 8.0% by mass, and still more preferably 1.0% to 8.0% by mass, with respect to the solid content of the composition.

<Solvent>

The composition of embodiment of the present invention usually contains a solvent.

Examples of the solvent which can be used in the preparation of the composition include organic solvents such as alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

Specific examples of these solvents include those described in [0441] to [0455] of US2008/0187860A.

In the present invention, a mixed solvent obtained by mixing a solvent containing a hydroxyl group and a solvent containing no hydroxyl group in the structure may be used as the organic solvent.

As the solvent containing a hydroxyl group and the solvent containing no hydroxyl group, the above-mentioned exemplary compounds can be appropriately selected and used, but as the solvent containing a hydroxyl group, an alkylene glycol monoalkyl ether, alkyl lactate, or the like is preferable, and propylene glycol monomethyl ether (PGME, alternative name: 1-methoxy-2-propanol), ethyl lactate, or methyl 2-hydroxyisobutyate is more preferable. Further, as the solvent containing no hydroxyl group, alkylene glycol monoalkyl ether acetate, alkyl alkoxy propionate, a monoketone compound which may contain a ring, cyclic lactone, alkyl acetate, and the like are preferable. Among these, propylene glycol monomethyl ether acetate (PGMEA, alternative name: 1-methoxy-2-acetoxypropane), ethyl ethoxypropionate, 2-heptanone, γ-butyrolactone, cyclohexanone, and butyl acetate are more preferable, and propylene glycol monomethyl ether acetate, ethyl ethoxypropionate, and 2-heptanone are still more preferable.

The mixing ratio (mass) of the solvent containing a hydroxyl group and the solvent containing no hydroxyl group is 1/99 to 99/1, preferably 10/90 to 90/10, and more preferably 20/80 to 60/40. A mixed solvent whose proportion of the solvent containing no hydroxyl group is 50% by mass or more is particularly preferable from the viewpoint of coating evenness. The solvent preferably includes propylene glycol monomethyl ether acetate, and is preferably a solvent formed of propylene glycol monomethyl ether acetate singly or a mixed solvent of two or more kinds of solvents including propylene glycol monomethyl ether acetate.

<Surfactant>

The composition of the embodiment of the present invention may or may not further contain a surfactant. In a case where the composition contains the surfactant, it is more preferable that the composition contains any one or two or more of fluorine-based and/or silicon-based surfactants (a fluorine-based surfactant, a silicon-based surfactant, and a surfactant having both a fluorine atom and a silicon atom).

By incorporating the surfactant into the composition of the embodiment of the present invention, it becomes possible to provide a resist pattern having improved adhesiveness and decreased development defects with good sensitivity and resolution in a case where an exposure light source of 250 nm or less, and particularly 220 nm or less, is used.

Examples of the fluorine-based and/or silicon-based surfactants include the surfactants described in paragraph [0276] in US2008/0248425A.

In addition, in the present invention, surfactants other than the fluorine-based and/or silicon-based surfactants described in paragraph [0280] in US2008/0248425A can also be used.

These surfactants may be used singly or in combination of a few surfactants.

In a case where the composition of the embodiment of the present invention contains a surfactant, the content of the surfactant is preferably 0.0001% to 2% by mass, and more preferably 0.0005% to 1% by mass, with respect to the total solid contents of the composition.

On the other hand, by setting the amount of the surfactant to be added to 10 ppm or less with respect to the total amount (excluding the solvent) of the composition, the hydrophobic resin is more unevenly distributed to the surface, so that the resist film surface can be made more hydrophobic, which can enhance the water tracking properties during the liquid immersion exposure.

<Other Additives>

The composition of embodiment of the present invention may or may not contain an onium carboxylate salt. Examples of such an onium carboxylate salt include those described in [0605] and [0606] in the specification of US2008/0187860A.

The onium carboxylate salt can be synthesized by reacting sulfonium hydroxide, iodonium hydroxide, ammonium hydroxide and carboxylic acid with silver oxide in a suitable solvent.

In a case where the composition of embodiment of the present invention contains the onium carboxylate salt, the content of the salt is generally 0.1% to 20% by mass, preferably 0.5% to 10% by mass, and more preferably 1% to 7% by mass, with respect to the total solid content of the composition.

The composition of embodiment of the present invention may further contain an acid proliferation agent, a dye, a plasticizer, a light sensitizer, a light absorber, an alkali-soluble resin, a dissolution inhibitor, a compound promoting solubility in a developer (for example, a phenol compound with a molecular weight of 1,000 or less, and an alicyclic or aliphatic compound having a carboxyl group), and the like, if desired.

Such a phenol compound having a molecular weight of 1,000 or less may be easily synthesized by those skilled in the art with reference to the method disclosed in, for example, JP1992-122938A (JP-H04-122938A), JP1990-028531A (JP-H02-028531A), U.S. Pat. No. 4,916,210A, EP219294B, and the like.

Specific examples of the alicyclic compound or aliphatic compound having a carboxyl group include, but not limited to, a carboxylic acid derivative having a steroid structure such as a cholic acid, deoxycholic acid or lithocholic acid, an adamantane carboxylic acid derivative, adamantane dicarboxylic acid, cyclohexane carboxylic acid, and cyclohexane dicarboxylic acid.

The concentration of the solid contents of the composition of embodiment of the present invention is usually 1.0% to 10% by mass, preferably 2.0% to 5.7% by mass, and more preferably 2.0% to 5.3% by mass. By setting the concentration of the solid contents to these ranges, it is possible to uniformly coat the resist solution on a substrate and additionally, it is possible to form a resist pattern having excellent line width roughness. The reason is not clear, but it is considered that, by setting the concentration of the solid contents to 10% by mass or less, and preferably 5.7% by mass or less, the aggregation of materials, particularly the photoacid generator, in the resist solution is suppressed, and as the result, it is possible to form a uniform resist film.

The concentration of the solid contents is the weight percentage of the weight of other resist components excluding the solvent with respect to the total weight of the composition.

A method for preparing the composition of embodiment of the present invention is not particularly limited, but the composition is preferably prepared by dissolving the above-mentioned respective components in a predetermined organic solvent, and preferably in the mixed solvent, and filtering the solution through a filter. The filter for use in filtration through a filter is preferably a polytetrafluoroethylene-, polyethylene-, or nylon-made filter with a pore size of 0.1 µm or less, more preferably 0.05 µm or less, and still more preferably 0.03 µm or less. In the filtration through a filter, as described in, for example, JP2002-062667A, circulating filtration may be carried out, or the filtration may be carried out by connecting plural kinds of filters in series or in parallel. In addition, the composition may be filtered in plural times. Furthermore, the composition may be subjected to a deaeration treatment or the like before or after filtration through a filter.

[Pattern Forming Method]

The present invention also relates to a pattern forming method using the actinic ray-sensitive or radiation-sensitive resin composition. Hereinafter, the pattern forming method of the embodiment of the present invention will be described. Further, the actinic ray-sensitive or radiation-sensitive film (typically a resist film) of an embodiment of the present invention will also be described, in addition to the pattern forming method.

The pattern forming method of the embodiment of the present invention includes:
  (i) a step of forming an actinic ray-sensitive or radiation-sensitive film using the above-mentioned actinic ray-sensitive or radiation-sensitive resin composition (film forming step),
  (ii) a step of irradiating the actinic ray-sensitive or radiation-sensitive film with actinic rays or radiation (exposing step), and
  (iii) a step of developing the actinic ray-sensitive or radiation-sensitive film irradiated with the actinic rays or radiation, using a developer.

The pattern forming method of the embodiment of the present invention is not particularly limited as long as it includes the steps (i) to (iii), and may further have the following step.

In the pattern forming method of the embodiment of the present invention, the exposing method in the (ii) exposing step is preferably liquid immersion exposure.

The pattern forming method of the embodiment of the present invention preferably includes (iv) a prebaking step before (ii) the exposing step.

The pattern forming method of the embodiment of the present invention preferably includes (v) a post-exposure baking step after (ii) the exposing step.

The pattern forming method of the embodiment of the present invention may include (ii) the exposing step in plural times.

The pattern forming method of the embodiment of the present invention may include (iv) the prebaking step in plural times.

The pattern forming method of the embodiment of the present invention preferably includes (v) the post-exposure baking step in plural times.

The actinic ray-sensitive or radiation-sensitive film in the embodiment of the present invention is a film formed using the above-mentioned actinic ray-sensitive or radiation-sensitive resin composition, and specifically, it is preferably a film formed by applying the composition onto a substrate.

In the pattern forming method of the embodiment of the present invention, (i) the actinic ray-sensitive or radiation-sensitive film forming step, (ii) the exposing step, and (iii) the developing step, each as described above, can be performed by a method that is generally known.

In addition, an antireflection film may further be formed between the actinic ray-sensitive or radiation-sensitive film and the substrate, as desired. As the antireflection film, a known organic or inorganic antireflection film can be appropriately used.

The substrate is not particularly limited, and a substrate which is generally used in a process for manufacturing a semiconductor such as an IC, and a process for manufacture of a circuit board for a liquid crystal, a thermal head, or the like, and other lithographic processes of photofabrication can be used. Specific examples of the substrate include an inorganic substrate such as silicon, $SiO_2$, and SiN, and a coating type inorganic substrate such as spin on glass (SOG).

It is also preferable that the pattern forming method of the embodiment of the present invention further includes (iv) a prebaking (PB) step after (i) the actinic ray-sensitive or radiation-sensitive film forming step and before (ii) the exposing step.

In addition, it is also preferable that the pattern forming method further includes (v) a post-exposure baking (PEB) step after (ii) the exposing step and before (iii) the developing step.

Such the baking accelerates a reaction in an exposed area, and thus, the sensitivity and/or the pattern profile is enhanced.

For both of PB and PEB, the heating temperature is preferably 70° C. to 130° C., and more preferably 80° C. to 120° C.

For both of PB and PEB, the heating time is preferably 30 to 300 seconds, more preferably 30 to 180 seconds, and still more preferably 30 to 90 seconds.

Heating may be performed using a means provided in ordinary exposure machines and development machines, or may also be performed using a hot plate or the like.

The light source wavelength used in the exposure device used in the present step is not particularly limited, and examples thereof include infrared rays, visible light, ultraviolet rays, far ultraviolet rays, extreme ultraviolet rays, X-rays, and electron beams, with the far ultraviolet rays at a wavelength of 250 nm or less being preferable, the far ultraviolet rays at a wavelength of 220 nm or less being more preferable, and the far ultraviolet rays at a wavelength of 1 to 200 nm being still more preferable. The light source wavelength is specifically a KrF excimer laser (248 nm), an ArF excimer laser (193 nm), an $F_2$ excimer laser (157 nm), X-rays, EUV (13 nm), electron beams, or the like, preferably the KrF excimer laser, the ArF excimer laser, EUV, or the electron beams, and more preferably the ArF excimer laser.

In the pattern forming method of the embodiment of the present invention, a liquid immersion exposing method can be applied to (ii) the exposing step. It is possible to combine the liquid immersion exposing method with super-resolution technology such as a phase shift method and a modified illumination method. The liquid immersion exposure can be performed by the method described in, for example, paragraphs [0594] to [0601] of JP2013-242397A.

In the (iii) developing step, a developer containing an organic solvent (hereinafter also referred to as an organic developer) or an alkali developer may also be used, but the organic developer is preferably used.

As the alkali developer, a quaternary ammonium salt typified by tetramethylammonium hydroxide is usually used, but in addition, aqueous alkali solutions of inorganic alkalis, primary to tertiary amines, alcohol amines, cyclic amines, or the like can also be used.

Specifically, as the alkali developer, aqueous alkali solutions of inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyldiethylamine; alcohol amines such as dimethylethanolamine and triethanolamine; quaternary ammonium salts such as tetramethylammonium hydroxide and tetraethylammonium hydroxide; cyclic amines such as pyrrole and piperidine; or the like are preferably used. Among those, an aqueous alkali solution of tetraethylammonium hydroxide is preferably used.

Furthermore, an appropriate amount of alcohols and a surfactant may also be added to the alkali developer. The alkali concentration of the alkali developer is usually 0.1% to 20% by mass. The pH of the alkali developer is usually 10.0 to 15.0.

The time for performing the development using the alkali developer is usually 10 to 300 seconds.

It is possible to appropriately adjust and use the alkali concentration (and pH) and the developing time of the alkali developer, depending on a pattern formed.

As the organic developer, a polar solvent such as a ketone-based solvent, an ester-based solvent, an alcohol-based solvent, an amide-based solvent, and an ether-based solvent, or a hydrocarbon-based solvent can be used.

Examples of the ketone-based solvent include 1-octanone, 2-octanone, 1-nonanone, 2-nonanone, acetone, 2-heptanone (methyl amyl ketone), 4-heptanone, I-hexanone, 2-hexanone, diisobutyl ketone, cyclohexanone, methylcyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butanoate, methyl 2-hydroxyisobutyrate, isoamyl acetate, isobutyl isobutyrate, and butyl propionate.

Examples of the alcohol-based solvent include alcohols such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol, and n-decanol; glycol-based solvents such as ethylene glycol, diethylene glycol, and triethylene glycol; and glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include dioxane and tetrahydrofuran, in addition to the glycol ether-based solvents.

Examples of the amide-based solvent include N-methyl-2-pyrrolidone, N,N-dimethylacetamide, N,N-dimethylformamide, hexamethylphosphoric triamide, and 1,3-dimethyl-2-imidazolidinone.

Examples of the hydrocarbon-based solvent include aromatic hydrocarbon-based solvents such as toluene and xylene, and aliphatic hydrocarbon-based solvents such as pentane, hexane, octane, and decane.

Furthermore, in an aliphatic hydrocarbon-based solvent which is a hydrocarbon-based solvent, a mixture of compounds having the same carbon atoms and different structures may be included. For example, in a case where decane is used as the aliphatic hydrocarbon-based solvent, 2-methylnonane, 2,2-dimethyloctane, 4-ethyloctane, isodecane, or the like, which is a compound having the same carbon atoms and different structures, may be included in the aliphatic hydrocarbon-based solvent.

Incidentally, one kind of the compound having the same carbon atoms and different structures may be included, or a plurality of kinds of the compound may be included as described above.

The solvents may be used by mixing a plurality of the solvents or by mixing the solvent of water or solvents other than the solvents. However, in order to sufficiently exhibit the effects of the present invention, it is preferable that the moisture content in the entire developer is less than 10% by mass, but it is more preferable that the developer substantially does not contain water.

That is, the content of the organic solvent with respect to the organic developer is preferably from 90% by mass to 100% by mass, and preferably from 95% by mass to 100% by mass, with respect to the total amount of the developer.

In particular, the organic developer is preferably a developer containing at least one organic solvent selected from the group consisting of a ketone-based solvent, an ester-based solvent, an alcohol-based solvent, an amide-based solvent, and an ether-based solvent.

The vapor pressure of the organic developer at 20° C. is preferably 5 kPa or less, more preferably 3 kPa or less, and particularly preferably 2 kPa or less. By setting the vapor pressure of the organic developer to 5 kPa or less, the evaporation of the developer on a substrate or in a development cup is inhibited, and the temperature uniformity within a wafer plane is improved, whereby the dimensional uniformity within a wafer plane is enhanced.

An appropriate amount of a surfactant may be added to the organic developer, if desired.

The surfactant is not particularly limited, but it is possible to use, for example, ionic or non-ionic fluorine-based and/or silicon-based surfactants, or the like. Examples of the fluorine-based and/or silicon-based surfactant include the surfactants described in JP1987-036663A (JP-S62-036663A), JP1986-226746A (JP-S61-226746A), JP1986-226745A (JP-S61-226745A), JP1987-170950A (JP-S62-170950A), JP1988-034540A (JP-S63-034540A), JP1995-230165A (JP-H07-230165A), JP1996-062834A (JP-H08-062834A), JP1997-054432A (JP-H09-054432A), JP1997-005988A (JP-H09-005988A), U.S. Pat. Nos. 5,405,720A, 5,360,692A, 5,529,881A, 5,296,330A, 5,436,098A, 5,576,143A, 5,294,511A, and 5,824,451A, and non-ionic surfactants are preferable. The non-ionic surfactant is not particularly limited, but it is more preferable to use a fluorine-based surfactant or a silicon-based surfactant.

The amount of the surfactant to be used is usually 0.001% to 5% by mass, preferably 0.005% to 2% by mass, and more preferably 0.01% to 0.5% by mass, with respect to the total amount of the developer.

The organic developer may include a basic compound. Examples of the basic compound include amine compounds, amido group-containing compounds, urea compounds, and nitrogen-containing heterocyclic compounds. Further, examples of the basic compound include those described for the basic compound that can be included in the composition as described above as an acid diffusion control agent.

Examples of the developing method include a method in which a substrate is immersed in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), and a method in which a developer is continuously discharged onto a substrate spun at a constant rate while scanning a developer discharging nozzle at a constant rate (a dynamic dispense method). Further, suitable ranges of the discharge pressure of the developer to be discharged, methods for adjusting the discharge pressure of the developer, and the like are not particularly limited, and for example, the ranges and the methods described in paragraphs [0631] to [0636] of JP2013-242397A can be used.

In the pattern forming method of the embodiment of the present invention, a step of performing development by using a developer including an organic solvent (organic solvent developing step) and a step of carrying out development by using an aqueous alkali solution (alkali developing step) may be used in combination. Thus, a finer pattern can be formed.

In the present invention, an area with a low exposure intensity is removed in the organic solvent developing step, and by further carrying out the alkali developing step, an area with a high exposure intensity is also removed. By virtue of multiple development processes in which development is carried out in a plurality of times in such a manner, a pattern can be formed by keeping only a region with an intermediate exposure intensity from not being dissolved, so that a finer pattern than usual can be formed (the same mechanism as in [0077] of JP2008-292975A).

After (iii) the developing step (after (V) a post-exposure baking step in a case where (V) the post-exposure baking step is included), a step of performing washing using a rinsing liquid (rinsing step) is preferably included.

As the rinsing liquid used in the rinsing step after performing development using an alkali developer, pure water is used as the rinsing liquid, and the rinsing liquid can also be used after adding an appropriate amount of a surfactant thereto. In this case, a treatment of removing the developer or the rinsing liquid adhering to the pattern by a supercritical fluid after the developing treatment or the rinsing treatment can be performed. In addition, a heating treatment of removing the moisture remaining in the pattern after the rinsing treatment or the treatment using a supercritical fluid can be performed.

The rinsing liquid used in the rinsing step after the step of performing development using a developer including an organic solvent is not particularly limited as long as the rinsing liquid does not dissolve the resist pattern, and a solution including a common organic solvent can be used. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is more preferably used.

Specific examples of the hydrocarbon-based solvent, the ketone-based solvent, the ester-based solvent, the alcohol-based solvent, the amide-based solvent, and the ether-based solvent include the same solvents as described for the developer including an organic solvent.

After the developing step using a developer including an organic solvent, it is more preferable to carry out a step of performing washing using a rinsing liquid containing at least one organic solvent selected from the group consisting of a ketone-based solvent, an ester-based solvent, an alcohol-based solvent, an amide-based solvent, and a hydrocarbon-based solvent, it is still more preferable to carry out a step of performing washing using a rinsing liquid containing an alcohol-based solvent or an ester-based solvent, it is particularly preferable to carry out a step of performing washing using a rinsing liquid containing a monohydric alcohol, and it is the most preferable to carry out a step of performing washing using a rinsing liquid containing a monohydric alcohol having 5 or more carbon atoms.

Here, examples of the monohydric alcohol used in the rinsing step include linear, branched, or cyclic monohydric alcohols, and specifically, 1-butanol, 2-butanol, 3-methyl-1- butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol, and methyl isobutyl carbinol. Examples of the monohydric alcohol having 5 or more carbon atoms include 1-hexanol, 2-hexanol, 4-methyl-2-pentanol, 1-pentanol, 3-methyl-1-butanol, and methyl isobutyl carbinol.

The rinsing liquid containing the hydrocarbon-based solvent is preferably a hydrocarbon compound having 6 to 30 carbon atoms, more preferably a hydrocarbon compound having 8 to 30 carbon atoms, and particularly preferably a hydrocarbon compound having 10 to 30 carbon atoms. By using the rinsing liquid including decane and/or undecane among those, pattern collapse can be suppressed.

In a case where the ester-based solvent is used as the rinsing liquid, a glycol ether-based solvent may be used, in addition to the ester-based solvent (one kind or two or more kinds). Specific examples of such a case include uses of an ester-based solvent (preferably butyl acetate) as a main component and a glycol ether-based solvent (preferably propylene glycol monomethyl ether (PGME)) as a side component. Thus, residue defects can be suppressed.

The respective components in plural numbers may be mixed, or the components may be mixed with an organic solvent other than the above solvents, and used.

The moisture content of the rinsing liquid is preferably 10% by mass or less, more preferably 5% by mass or less, and still more preferably 3% by mass or less. By setting the moisture content to 10% by mass or less, good development characteristics can be obtained.

The vapor pressure at 20° C. of the rinsing liquid which is used after the step of carrying out development using a developer including an organic solvent is preferably from 0.05 kPa to 5 kPa, more preferably from 0.1 kPa to 5 kPa, and still more preferably from 0.12 kPa to 3 kPa. By setting the vapor pressure of the rinsing liquid to be from 0.05 kPa to 5 kPa, the temperature uniformity within a wafer surface is improved, and further, the dimensional uniformity within a wafer surface is enhanced by suppression of swelling due to the permeation of the rinsing liquid.

The rinsing liquid can be used after an appropriate amount of a surfactant is added thereto. In the rinsing step, a wafer which has been developed using a developer including an organic solvent is subjected to a washing treatment using a rinsing liquid including an organic solvent. A method for the washing treatment is not particularly limited, and examples thereof include a method in which a rinsing liquid is continuously discharged on a substrate spun at a constant rate (a rotation application method), a method in which a substrate is immersed in a tank filled with a rinsing liquid for a certain period of time (a dip method), and a method in which a rinsing liquid is sprayed on a substrate surface (a spray method). Among these, a method in which a washing treatment is carried out using a rotation application method, and a substrate is rotated at a rotation speed of 2,000 rpm to 4,000 rpm after washing, thereby removing the rinsing liquid from the substrate, is preferable. Further, it is preferable that a heating step (post-baking) is carried out after the rinsing step. The residual developer and the rinsing liquid between and inside the patterns are removed by the baking. The heating step after the rinsing step is carried out at usually 40° C. to 160° C., and preferably at 70° C. to 95° C., and usually for 10 seconds to 3 minutes, and preferably for 30 seconds to 90 seconds.

It is preferable that various materials (for example, a resist solvent, a developer, a rinsing liquid, a composition for forming an antireflection film, and a composition for forming a topcoat) used in the actinic ray-sensitive or radiation-sensitive resin composition of the embodiment of the present invention, and the pattern forming method of the embodiment of the present invention do not include impurities such as metals. The content of the impurities included in these materials is preferably 1 ppm or less, more preferably 100 ppt or less, and still more preferably 10 ppt or less, but the material not having substantially the impurities (at a detection limit of a measurement device or less) is particularly preferable.

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a polytetrafluoroethylene-made filter, a polyethylene-made filter, and a nylon-made filter are preferable. As the filter, a filter which had been washed with an organic solvent in advance may be used. In the step of filtration using a filter, plural kinds of filters may be connected in series or in parallel, and used. In a case of using plural kinds of filters, a combination of filters having different pore diameters and/or materials may be used. In addition, various materials may be filtered plural times, and a step of filtering plural times may be a circulatory filtration step.

Moreover, examples of the method for reducing the impurities such as metals included in the various materials include a method involving selecting raw materials having a small content of metals as raw materials constituting various materials, a method involving subjecting raw materials constituting various materials to filtration using a filter, and a method involving performing distillation under the condition with contamination being suppressed to the largest degree by, for example, lining the inside of a device with TEFLON (registered trademark). The preferred conditions for filtration using a filter, which is carried out for raw materials constituting various materials, are the same as described above.

In addition to the filtration using a filter, removal of impurities by an adsorbing material may be carried out, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

A method for improving the surface roughness of a pattern may be applied to the pattern formed by the pattern forming method of the embodiment of the present invention. Examples of the method for improving the surface roughness of a pattern include the method of treating a resist pattern by plasma of a hydrogen-containing gas disclosed in WO2014/002808A. In addition, known methods as described in JP2004-235468A, US2010/0020297A, JP2009-019969A, and Proc. of SPIE Vol. 8328 83280N-1 "EUV Resist Curing Technique for LWR Reduction and Etch Selectivity Enhancement" may be applied.

The pattern forming method of the embodiment of the present invention can be used for a guide pattern formation in a directed self-assembly (DSA) (see, for example, ACS Nano Vol. 4, No. 8, Pages 4815 to 4823).

In addition, a resist pattern formed by the method can be used as a core material (core) of the spacer process disclosed in JP1991-270227A (JP-H03-270227A) and JP2013-164509A.

[Method for Manufacturing Electronic Device]

In addition, the present invention also relates to a method for manufacturing an electronic device, including the above-mentioned pattern forming method of the embodiment of the present invention. An electronic device manufactured by the method for manufacturing an electronic device of an embodiment of the present invention is suitably mounted on electric or electronic equipment (for example, home electronics, office automation (OA)-related equipment, media-related equipment, optical equipment, and telecommunication equipment).

EXAMPLES

Hereinafter, the present invention will be described in more detail with reference to Examples, but the present invention is not limited thereto.

Synthesis Example: Synthesis of Compound (PAG-2)

As in the following synthesis scheme, 200 mL of acetonitrile (MeCN) and 100 mL of water were added to 50 g of ethyl bromofluoroacetate and 34.1 g of sodium sulfite ($Na_2SO_3$), and the mixture was stirred at 85° C. for 6 hours. The reaction liquid was filtered, acetonitrile was evaporated under reduced pressure, the reaction liquid was then transferred to a separatory funnel, and the aqueous layer was washed with 100 mL of hexane. 36 g of sodium chloride was added to the aqueous layer and then the aqueous layer was extracted three times with 100 mL of acetonitrile. Acetonitrile was evaporated under reduced pressure to obtain a compound 1 as a white solid. (28 g, yield: 50%) $^1$H-NMR, 400 MHz, δ ((d-DMSO) ppm: 1.34 (3H, d), 4.32 (2H, q), 5.50 (1H, d).

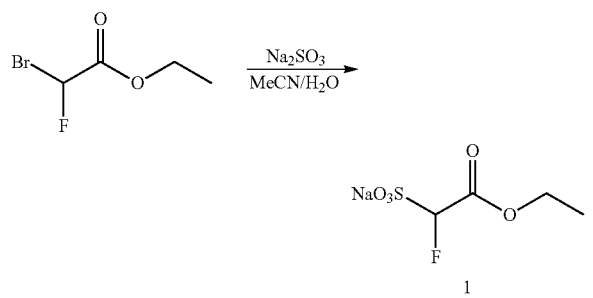

As in the following synthesis scheme, 160 mL of tetrahydrofuran (THF) and 24 mL of methanol (MeOH) were added to 20 g of the compound 1, and the mixture was cooled to 0° C. 5.4 g of sodium borohydride ($NaBH_4$) was added in portions such that the inner temperature did not exceed 10° C., and then the reaction liquid was warmed to room temperature. After the mixture was stirred at room temperature for 2 hours, the reaction liquid was cooled to 0° C. and 50 mL of water was added thereto. The solvent was evaporated under reduced pressure to obtain a compound 2 as a white solid. (25 g, purity 79%) $^1$H-NMR, 400 MHz, δ ((MeOD) ppm: 3.86-3.96 (1H, m), 4.08 (1H, ddd), 5.02 (1H, ddd).

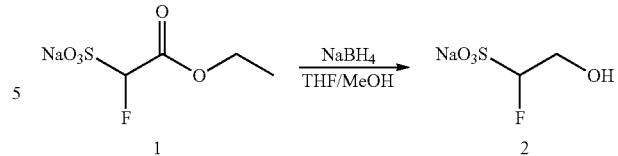

As in the following synthesis scheme, 120 mL of water and 27 mL of tetrahydrofuran (THF) were added to 15.5 g of the compound 2 (purity 79%) and dissolved therein, and then 2.9 g of sodium hydroxide (NaOH) was added thereto. After the mixture was stirred at room temperature for 1 hour, the reaction liquid was cooled to 0° C. and 14.42 g of 1-adamantanecarbonyl chloride was added thereto. The mixture was stirred at 0° C. for 2 hours, neutralized by the addition of 1 N hydrochloric acid, and warmed to room temperature. 10.0 g of triphenylsulfonium bromide and 120 mL of chloroform added to the reaction liquid and the mixture was stirred for 1 hour. The reaction solution was transferred to a separatory funnel and the organic layer was washed three times with 100 mL of water. Chloroform was evaporated under reduced pressure and crystallized from isopropyl ether to obtain a compound (PAG-2) as a white solid. (14.9 g, yield 36%) $^1$H-NMR, 400 MHz, δ ($CDCl_3$) ppm: 1.70 (6H, m), 1.90 (6H, m), 2.00 (3H, m), 4.51 (1H, m), 4.70 (1H, ddd), 5.26 (1H, ddd), 7.68-7.80 (15H, m).

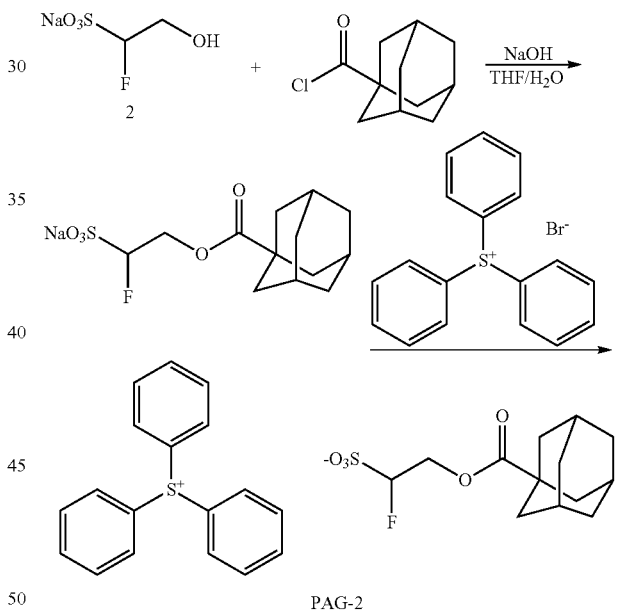

<Synthesis Example: Synthesis of Compound (PAG-5)

Based on the following synthesis scheme, a compound (PAG-5) was synthesized.

(Synthesis of Compound (A-1))

A solution obtained by dissolving 450 g of methylene chloride in 52.7 g of adamantane ethanol was cooled to −20° C. and 90.0 g of trifluoromethanesulfonic acid anhydride ($Tf_2O$) was added dropwise thereto. After dropwise addition, 43.4 g of diisopropylethylamine ($iPr_2EtN$) was added dropwise thereto. After completion of dropwise addition, the mixture was stirred at a temperature between −10° C. and 0° C. for 2 hours. The reaction liquid was poured into 500 mL of a cooled aqueous ammonium chloride solution and 1 L of hexane to extract the organic layer, and then washed with an aqueous ammonium solution, water, and a saturated aqueous sodium chloride solution. After drying over sodium sulfate, the solvent was evaporated to obtain 89.4 g of a compound (A-1). (Yield 98%) ¹H-NMR, 400 MHz, δ (CDCl₃) ppm: 1.52-1.56 (6H, m), 1.59-1.76 (8H, m), 1.94-2.02 (3H, m), 4.61 (2H, t).

(Synthesis of Compound (A-2))

A solution of 120 g of isobutanol and 600 g of methylene chloride (CH₂Cl₂) was cooled to 0° C., and 204 g of mesyl chloride (MsCl) was added dropwise thereto. Thereafter, 251 g of diisopropylethylamine (iPr₂EtN) was added dropwise to the mixture, and after the dropwise addition, the mixture was stirred at 0° C. for 1 hour. Thereafter, water was added to the reaction liquid, and the organic layer was washed with saturated sodium bicarbonate, and subsequently with saturated saline. The residue was dried over sodium sulfate and then the solvent was evaporated to obtain a crude product. The crude product was distilled under reduced pressure to obtain 199.6 g of a compound (A-2). (Yield 81%) ¹H-NMR, 400 MHz, δ (CDCl₃) ppm: 0.99 (6H, d), 2.04 (1H, m), 3.00 (3H, s), 4.00 (2H, d).

(Synthesis of Compound (A-3))

A mixed liquid of 36.5 g of the compound (A-2), 460 mL of tetrahydrofuran (THF), and 40 mL of dimethylimidazolidinone (DMI) was cooled to −60° C., and 90 mL of n-butyllithium (nBuLi) (a 2.67 M hexane solution) was added dropwise thereto. After dropwise addition, the mixture was stirred at −60° C. for 1 hour, a solution of 50.0 g of the compound (A-1) and 90 mL of tetrahydrofuran was added dropwise thereto, and then after dropwise addition, the mixture was stirred at −20° C. to 0° C. for 4 hours. Thereafter, a saturated aqueous ammonium chloride solution was added to the reaction liquid, and tetrahydrofuran was evaporated under reduced pressure. Ethyl acetate was added thereto, the mixture was washed with saturated saline, the organic layer was dried over sodium sulfate, and then the solvent was evaporated. The crude product was purified by silica gel column to obtain 32.2 g of a compound (A-3). (Yield 64%) ¹H-NMR, 400 MHz, δ (CDCl₃) ppm: 0.99 (6H, d), 1.16 (2H, m), 1.45-1.50 (6H, m), 1.58-1.75 (6H, m), 1.76-1.88 (2H, m), 1.91-2.10 (4H, m), 3.00-3.07 (2H, m), 3.98 (2H, d).

(Synthesis of Compound (A-4))

A solution of 11.9 g of the compound (A-3) and 160 mL of tetrahydrofuran was cooled to −60° C., and 16 mL of n-butyllithium (a 2.67 M hexane solution) was added dropwise thereto. After dropwise addition, the mixture was warmed to 0° C. and stirred for 1 hour, and then cooled to −40° C. 13.2 g of N-fluorobenzene sulfonimide was added to the reaction liquid, and then the mixture was warmed to 0° C. and stirred for 2 hours. Thereafter, a saturated aqueous ammonium chloride solution was added thereto and tetrahydrofuran was evaporated under reduced pressure. Ethyl acetate was added thereto, the mixture was washed with saturated saline and then dried over sodium sulfate, and the solvent was evaporated under reduced pressure to obtain a crude product. This crude product was purified by silica gel column to obtain 5.3 g of a compound (A-4). (Yield 42%) ¹H-NMR, 400 MHz, δ (CDCl₃) ppm: 0.99 (6H, d), 1.12-1.44 (2H, m), 1.45-1.50 (6H, m), 1.58-1.76 (6H, m), 1.90-2.10 (6H, m), 4.14 (2H, d), 5.17 (1H, dddd).

(Synthesis of Compound (PAG-5))

5.3 g of compound (A-4), 2.4 g of sodium iodide (NaI), and 56 g of acetonitrile (MeCN) were heated at 60° C. and the mixture was stirred for 4 hours. Thereafter, the solvent was evaporated under reduced pressure to obtain 4.7 g of a compound (A-5). (Yield 99%)

4.7 g of compound (A-5), 5.4 g of triphenylsulfonium bromide, 65 g of dichloromethane, and 65 g of ion exchange water were stirred at room temperature. Thereafter, the organic layer was extracted and washed with ion exchange water, and then the solvent was evaporated. The obtained crude product in the form of an oil was crystallized by the addition of diisopropyl ether to obtain 6.2 g of a compound (PAG-5) as a desired product. (Yield 73%) ¹H-NMR, 400 MHz, δ (CDCl₃) ppm: 1.11-1.24 (1H, m), 1.34-1.53 (7H, m), 1.54-1.72 (6H, m), 1.84-2.14 (5H, m), 4.83-5.04 (1H, m), 7.64-7.87 (15H, m).

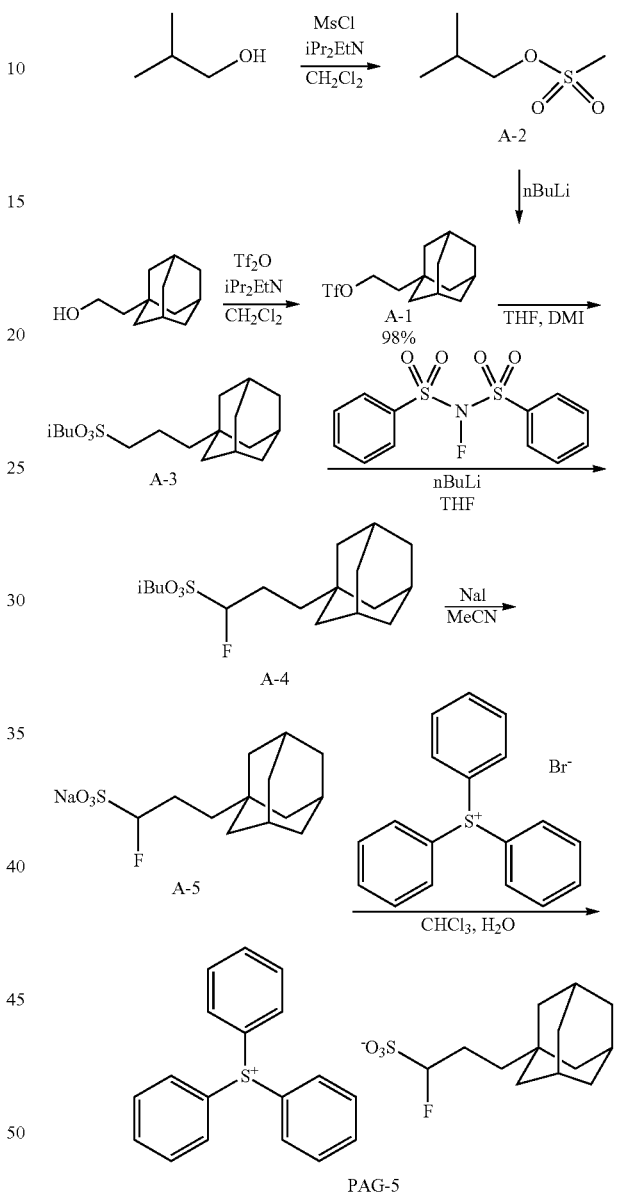

Compounds (PAG-1), (PAG-3), (PAG-4), and (PAG-6) to (PAG-19) described later were also synthesized based on the same method as the above synthesis examples.

Examples 1 to 23 and Comparative Examples 1 and 2

<Preparation of Resist Composition>

The respective components described in Table 2 below were dissolved in a solvent to prepare a solution having a concentration of the solid contents of 3.8% by mass. Then, the obtained solution was filtered through a polyethylene filter having a pore size of 0.1 μm to prepare an actinic ray-sensitive or radiation-sensitive resin composition (resist composition).

<Method for Forming Resist Pattern>

A composition for forming an organic antireflection film, ARC29SR (manufactured by Nissan Chemical Industries, Ltd.), was applied onto a silicon wafer and baked at 205° C. for 60 seconds to form an antireflection film having a film thickness of 95 nm. A resist composition was applied onto the obtained antireflection film and pre-baked (PB) at 100° C. for 60 seconds to form a resist film having a film thickness of 85 nm.

The obtained wafer was exposed through a 6% halftone mask with a 1:1 line-and-space pattern having a line width of 44 nm, using an ArF excimer laser liquid immersion scanner (manufactured by ASML; XTI700i, NA 1.20, C-Quad, outer sigma 0.900, inner sigma 0.812, and XY polarization). Ultrapure water was used as an immersion liquid. Thereafter, the wafer was post-exposure baked (PEB) at 105° C. for 60 seconds. Then, the wafer was developed by puddling it with an organic developer (butyl acetate) for 30 seconds, and puddled and rinsed with a rinsing liquid [methyl isobutyl carbinol (MIBC)] for 30 seconds. Subsequently, the wafer was spun at a rotation speed of 4,000 rpm for 30 seconds to form a 1:1 line-and-space pattern having a line width of 44 nm.

<Evaluation of Resist Pattern>

For the obtained resist pattern, the line width roughness, the exposure latitude, and the depth of focus were evaluated, based on the following evaluation method. The results are shown in Table 2 below.

[Evaluation of Roughness Performance (Line Width Roughness; LWR)]

The obtained 1:1 line-and-space pattern with a line width of 44 nm was observed from the upper part of the pattern, using a length-measuring scanning electron microscope (SEM S-8840, manufactured by Hitachi High Technologies Corp.), line widths were measured at 50 points within a range of 2 μm of edges in the longitudinal direction of the line pattern, the standard deviation of the measured variation was determined, and 3a was calculated therefrom. A smaller value thereof indicates better performance.

<Evaluation of Exposure Latitude (EL)>

An exposure dose that reproduces a 1:1 line-and-space pattern with a line width of 44 nm was defined as an optimal exposure dose, Eopt. Subsequently, an exposure dose at which the line width of the line reached a desired value 44 nm±10% (that is, 39.6 nm and 48.4 nm) was determined. In addition, an exposure latitude (EL) defined by the following equation was calculated. Further, the evaluation standards (A to D) are as follows. A larger value of EL indicates that a change in the line width with respect to a change in the exposure dose is small, which is thus preferable.

EL (%)=[[(Exposure dose at which the line width of the line becomes 48.4 nm)−(Exposure dose at which the line width of the line becomes 39.6 nm)]/$E$opt]×100

<Method for Evaluating Depth of Focus (DOF)>

At the optimal exposure dose, Eopt, for forming a line pattern with a line width of 44 nm, exposure and development were performed by changing the conditions of the exposure focus at an interval of 10 nm in the focus direction, the space line width (CD) of each of the obtained patterns was measured using a line-width length-measuring dimension scanning electron microscope SEM (S-9380 manufactured by Hitachi High Technologies Corp.). A focus corresponding to the minimum value or the maximum value in a curve obtained by plotting the respective CDs was defined as a best focus. In a case where the focus was changed while being centered on the best focus, a variation width of the focus with which a line width of 44 nm±10% was allowable, that is, a depth of focus (DOF) (nm) was calculated. A larger value of the depth of focus is more preferable.

TABLE 2

| | Acid-decomposable resin (10 g) | Eth | Acid generator (g) | pKa | Basic compound (g) | Hydrophobk resin (0.05 g) | Solvent (mass ratio) | Surfactant (0.03 g) | LWR (nm) | EL (%) | DOF (nm) |
|---|---|---|---|---|---|---|---|---|---|---|---|
| Example 1 | Resin 1 | 5.64 | PAG-1 (2.0) | −1.40 | N-4 (0.35) | 1b | SL-1/SL-2 (80/20) | — | 3.45 | 17.1 | 109 |
| Example 2 | Resin 2 | <5.20 | PAG-2 (2.2) | −0.81 | N-4 (0.32) | 2b | SL-1/SL-2 (80/20) | — | 3.25 | 18.8 | 113 |
| Example 3 | Resin 3 | 5.2 | PAG-3 (2.0) | −0.66 | N-4 (0.32) | 3b | SL-1/SL-2 (80/20) | — | 3.45 | 17.6 | 115 |
| Example 4 | Resin 4 | 5.43 | PAG-4 (2.3) | −0.05 | N-6 (0.31) | 1b | SL-1/SL-2 (75/25) | — | 3.40 | 18.6 | 114 |
| Example 5 | Resin 5 | 5.36 | PAG-5 (2.0) | −0.02 | N-2 (0.29) | 1b | SL-1/SL-2 (90/10) | — | 3.16 | 18.6 | 118 |
| Example 6 | Resin 6 | 5.31 | PAG-1 (2.0) | −1.40 | N-3 (0.30) | 3b | SL-1/SL-3 (80/20) | — | 3.40 | 17.0 | 111 |
| Example 7 | Resin 7 | <5.20 | PAG-7 (2.6) | 0.77 | N-6 (0.33) | 1b | SL-1 | — | 3.29 | 18.6 | 117 |
| Example 8 | Resin 8 | <5.20 | PAG-8 (2.3) | 1.05 | N-4 (0.35) | 2b | SL-3 | W-1 | 3.21 | 18.4 | 114 |
| Example 9 | Resin 9 | <5.20 | PAG-9 (2.3) | −0.81 | N-5 (0.35) | 1b | SL-1 | — | 3.37 | 18.1 | 116 |
| Example 10 | Resin 10 | 5.46 | PAG-10 (2.2) | 1.87 | N-4 (0.32) | 3b | SL-3 | — | 3.20 | 19.9 | 121 |
| Example 11 | Resin 11 | 5.59 | PAG-11 (2.1) | −0.81 | N-02/N-4 (0.15/0.17) | 3b | SL-1/SL-4 (90/10) | — | 3.48 | 19.7 | 119 |
| Example 12 | Resin 4 | 5.43 | PAG-3 (2.0) | −0.66 | N-2 (0.29) | 1b | SL-1/SL-2/SL-4 (8/10/10) | — | 3.43 | 17.5 | 109 |
| Example 13 | Resin 12 | 5.64 | PAG-13 (2.0) | −0.02 | N-2 (0.29) | 3b | SL-1/SL-2/SL-4 (80/10/10) | — | 3.11 | 19.7 | 117 |
| Example 14 | Resin 7 | <5.20 | PAG-1 (2.0) | −1.40 | N-6 (0.31) | 2b | SL-1 | — | 3.31 | 20.1 | 120 |
| Example 15 | Resin 2 | <5.20 | PAG-5/PAG-13 (1.0/1.0) | PAG-13(−0.02)/PAG-5(−0.02) | N-1 (0.30) | 1b | SL-1/SL-2 (80/20) | — | 3.21 | 19.0 | 113 |
| Example 16 | Resin 11 | 5.59 | PAG-6 (2.1) | 1.87 | N-7 (0.31) | 1b | SL-1 | — | 3.18 | 19.7 | 117 |

TABLE 2-continued

| | Acid-decomposable resin (10 g) | Eth | Acid generator (g) | pKa | Basic compound (g) | Hydrophobic resin (0.05 g) | Solvent (mass ratio) | Surfactant (0.03 g) | LWR (nm) | EL (%) | DOF (nm) |
|---|---|---|---|---|---|---|---|---|---|---|---|
| Example 17 | Resin 2 | <5.20 | PAG-12 (2.1) | 0.77 | N-4 (0.35) | 1b | SL-1/SL-2 (80/20) | — | 3.15 | 18.7 | 116 |
| Example 18 | Resin 11 | 5.59 | PAG-14 (2.1) | 1.87 | N-2 (0.35) | 1b | SL-1 | W-1 | 3.16 | 19.6 | 118 |
| Example 19 | Resin 16 | 5.45 | PAG-13 (2.0) | -0.02 | N-3 (0.35) | 1b | SL-1/SL-3 (80/20) | — | 3.15 | 20.0 | 115 |
| Example 20 | Resin 10 | 5.46 | PAG-2/PAG-5 (1.0/1.0) | PAG-2(-0.81)/PAG-5(-0.02) | N-4 (0.35) | 1b | SL-1 | — | 3.25 | 20.2 | 120 |
| Example 21 | Resin 11 | 5.59 | PAG-13 (2.0) | -0.02 | N-2 (0.35) | 1b | SL-3 | — | 3.13 | 20.1 | 121 |
| Example 22 | Resin 10 | 5.46 | PAG-4 (2.3) | -0.05 | N-5 (0.30) | 1b | SL-1 | — | 3.22 | 19.8 | 119 |
| Example 23 | Resin 2/Resin 3 (5.0 g/5.0 g) | <5.20 | PAG-11 (2.1) | -0.81 | N-5 (0.35) | 1b | SL-1/SL-2 (70/30) | W-1 | 3.32 | 18.6 | 116 |
| Example 24 | Resin 13 | <5.20 | PAG-6 (2.1) | 1.87 | N-4 (0.35) | 1b | SL-1/SL-4 (90/10) | — | 3.15 | 19.9 | 121 |
| Example 25 | Resin 14 | <5.20 | PAG-6 (2.1) | 1.87 | N-7 (0.35) | 3b | SL-1/SL-4 (90/10) | — | 3.11 | 19.7 | 118 |
| Example 26 | Resin 1 | 5.64 | PAG-17/PAG-19 (1.2/1.2) | -0.82 | — | 3b | SL-1/SL-4 2 (80/20) | — | 3.30 | 17.4 | 115 |
| Example 27 | Resin 1 | 5.64 | PAG-5/PAG-16 (1.0/1.0) | -0.02 | — | 3b | SL-1/SL-4 (90/10) | — | 3.20 | 19.0 | 118 |
| Example 28 | Resin 6 | 5.31 | PAG-18 (2.2) | -0.81 | N-7 (0.35) | 2b | SL-1/SL-2 (80/20) | — | 3.22 | 18.3 | 111 |
| Example 29 | Resin 15 | 5.64 | PAG-5/PAG-16 (0.7/1.3) | -0.02 | — | 1b | SL-1/SL-2 (80/20) | — | 3.28 | 19.4 | 119 |
| Comparative Example 1 | Resin 17 | 6.71 | PAG-2 (2.2) | -0.81 | N-4 (0.35) | 1b | SL-1/SL-2 (80/20) | | 3.63 | 15.2 | 98 |
| Comparative Example 2 | Resin 1 | 5.64 | PAG-15 (2.0) | -1.90 | N-2 (0.29) | 1b | SL-1/SL-2/SL-4 (80/10/10) | | 3.66 | 15.5 | 99 |

The resins (acid-decomposable resins), the photoacid generators, the acid diffusion control agents, the hydrophobic resins, the surfactants, and the solvents in Table 2 are as follows.

[Acid-Decomposable Resin]

The molar ratios, the weight-average molecular weights (Mw), and the dispersities (Mw/Mn) of the repeating units are also shown below, in addition to the structures of the repeating units in the respective resins.

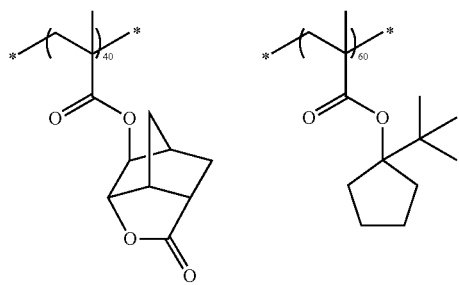

Resin 1

Mw = 10000
Mw/Mn = 1.64

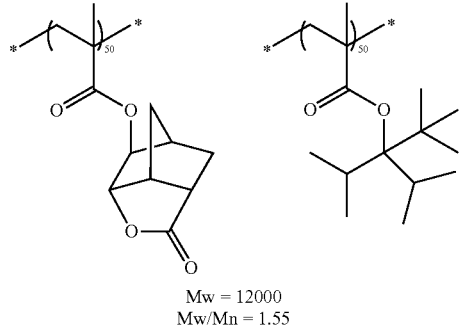

Resin 2

Mw = 12000
Mw/Mn = 1.55

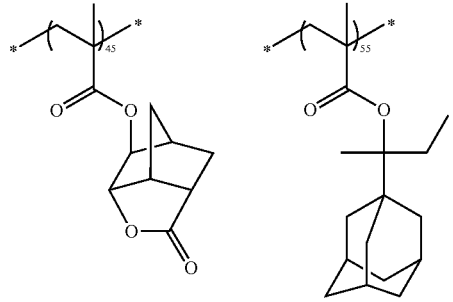

Resin 3

Mw = 13500
Mw/Mn = 1.66

-continued
Resin 4
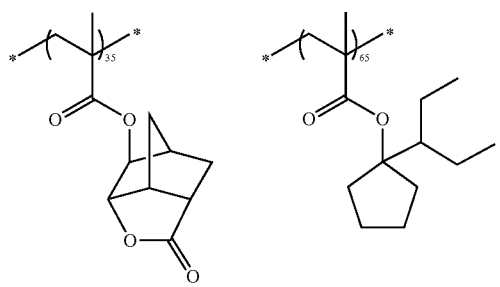
Mw = 9000
Mw/Mn = 1.70
Resin 5
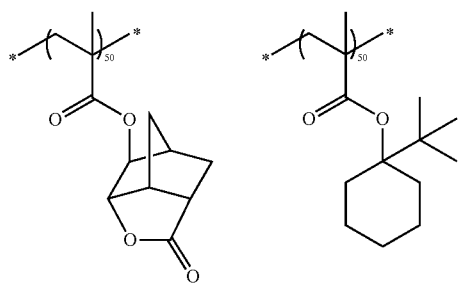
Mw = 11000
Mw/Mn = 1.54
Resin 6
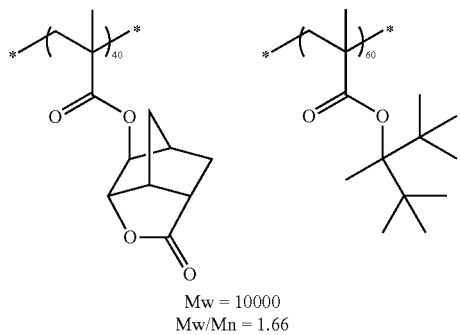
Mw = 10000
Mw/Mn = 1.66
Resin 7
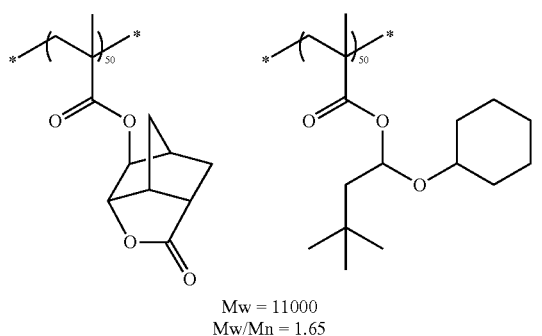
Mw = 11000
Mw/Mn = 1.65
-continued
Resin 8
Mw = 14500
Mw/Mn = 1.65
Resin 9
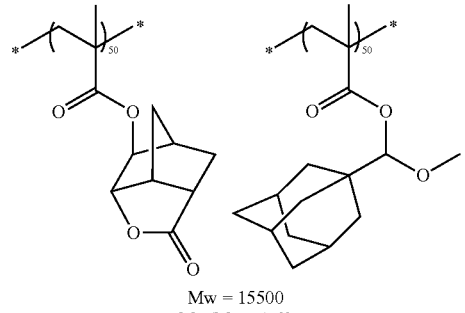
Mw = 15500
Mw/Mn = 1.69
Resin 10
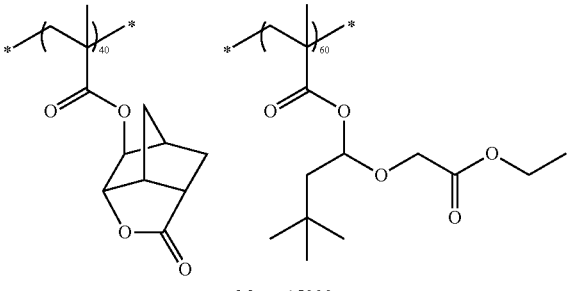
Mw = 15000
Mw/Mn = 1.64
Resin 11
Mw = 13000
Mw/Mn = 1.59

125
-continued
Resin 12
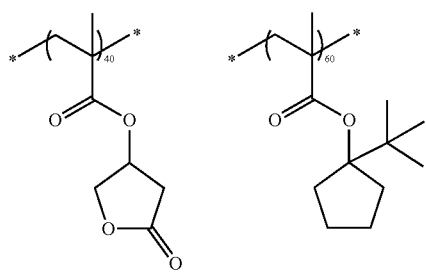
Mw = 8000
Mw/Mn = 1.66
Resin 13
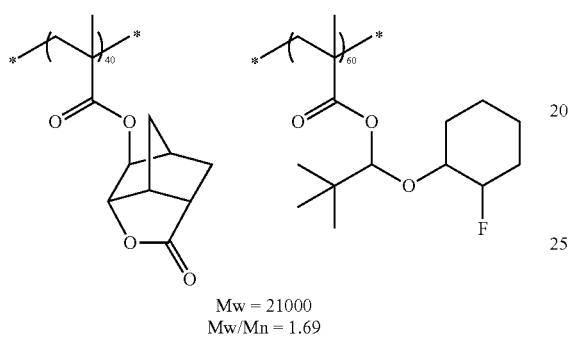
Mw = 21000
Mw/Mn = 1.69
Resin 14
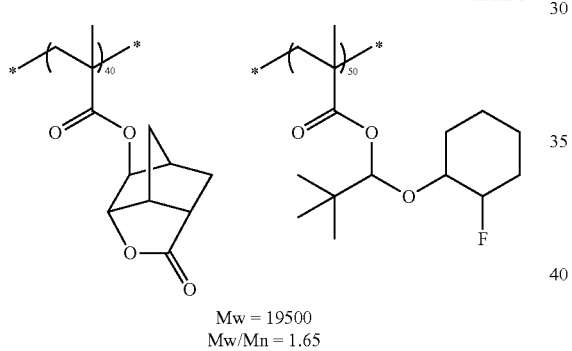
Mw = 19500
Mw/Mn = 1.65
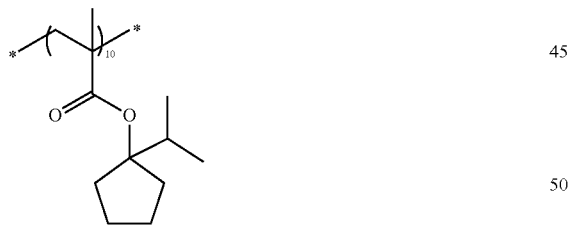
Resin 15
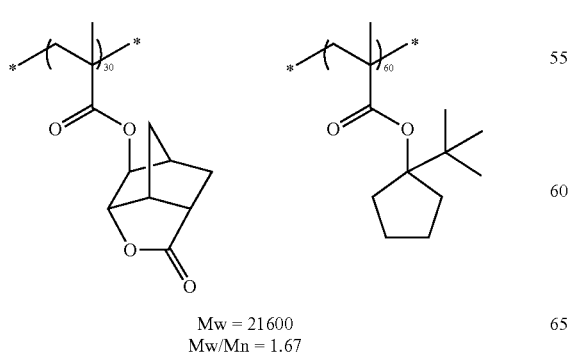
Mw = 21600
Mw/Mn = 1.67
126
-continued
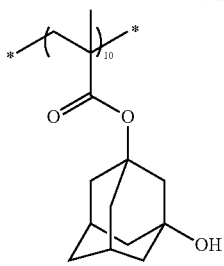
Resin 16
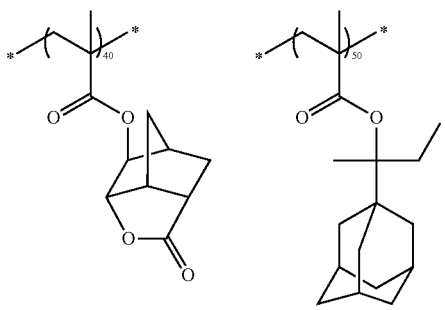
Mw = 12000
Mw/Mn = 1.56
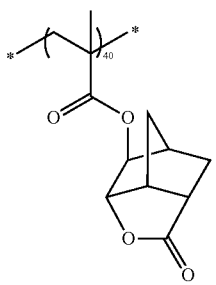
Resin 17
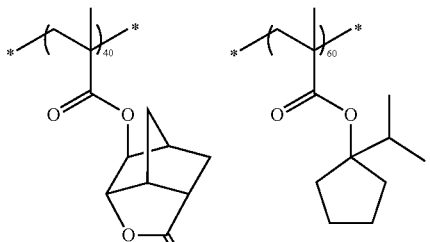
Mw = 10000
Mw/Mn = 1.65
[Photoacid Generator]
PAG-1
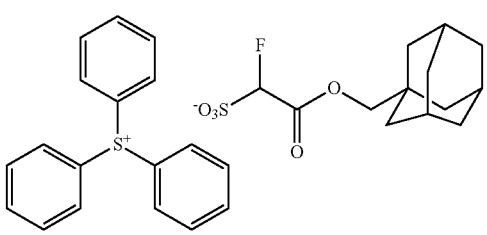

-continued
PAG-2
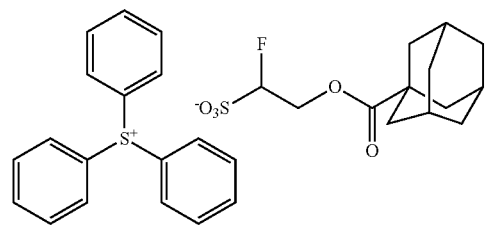
PAG-3
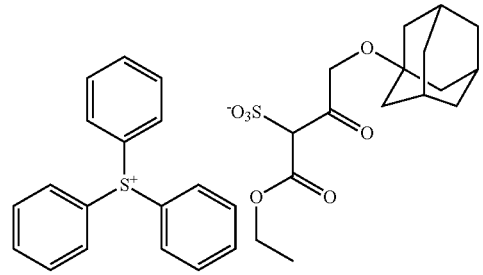
PAG-4
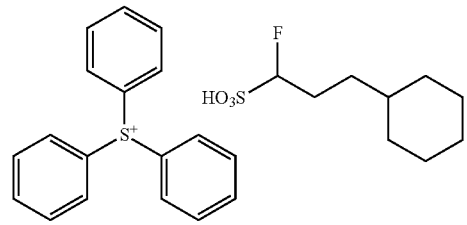
PAG-5
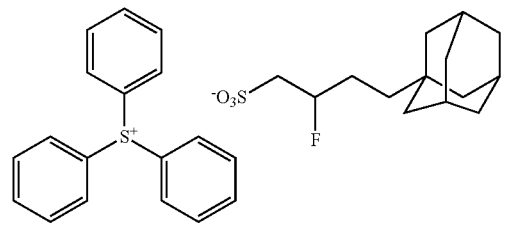
PAG-6
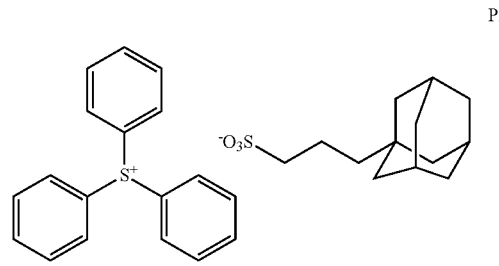
PAG-7
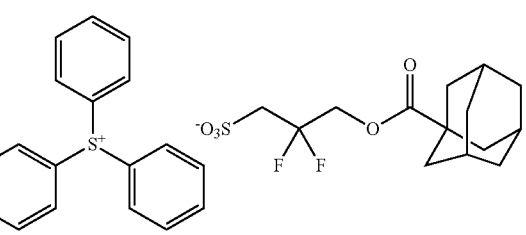
-continued
PAG-8
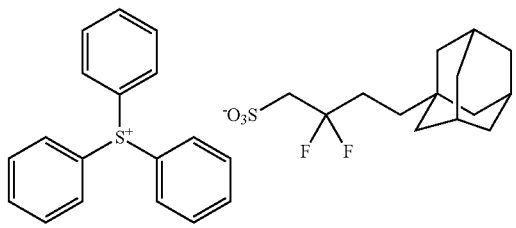
PAG-9
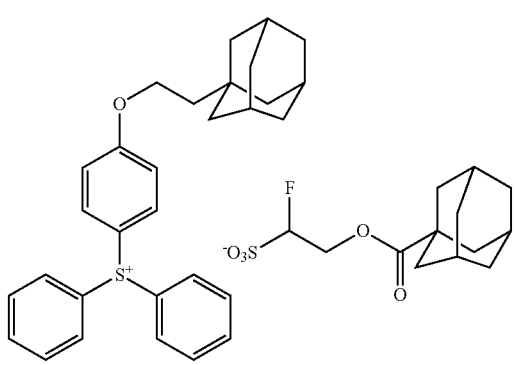
PAG-10
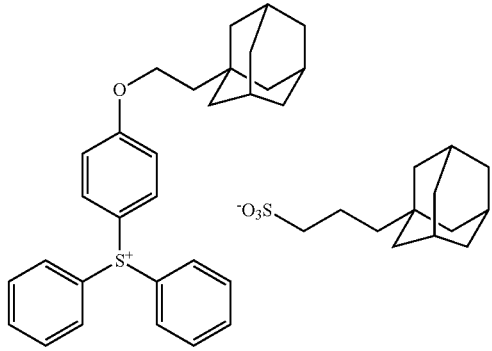
PAG-11
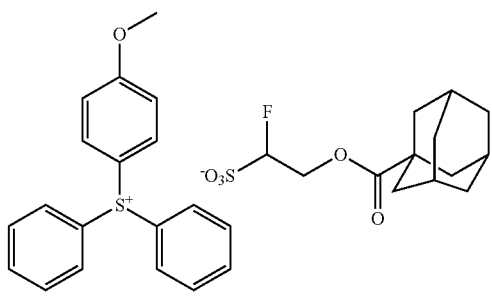
PAG-12
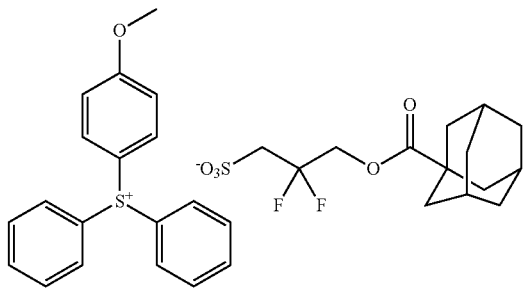

PAG-13
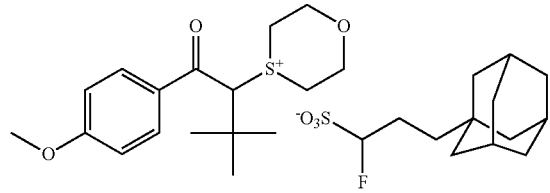
PAG-14
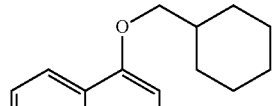
PAG-15
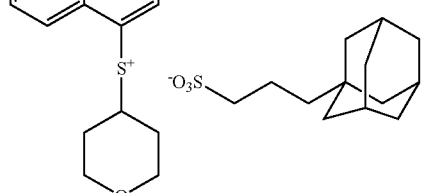
PAG-16
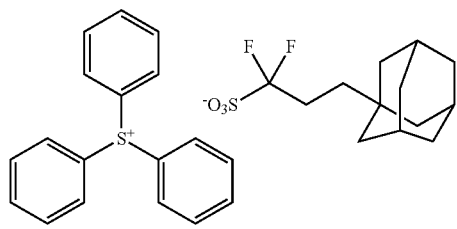
PAG-17
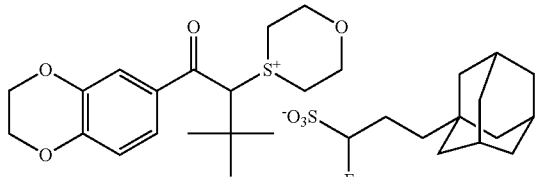
PAG-18
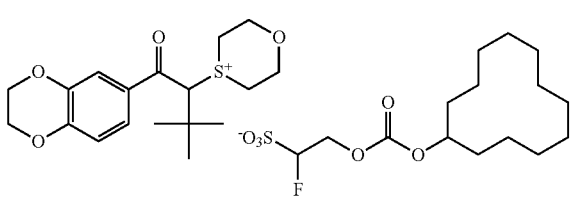
PAG-19
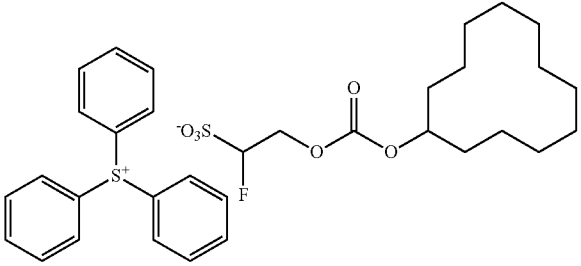
[Acid Diffusion Control Agent]
N-1
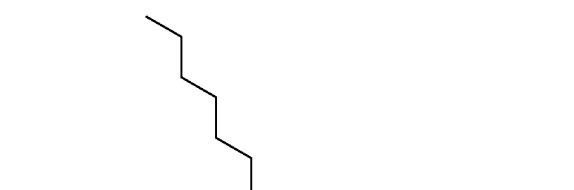
N-2
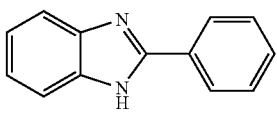
N-3
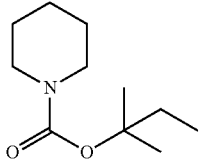
N-4
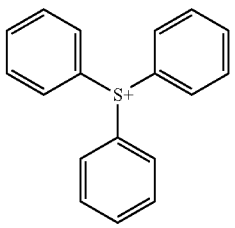
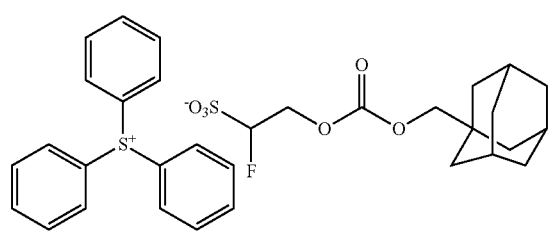
N-5
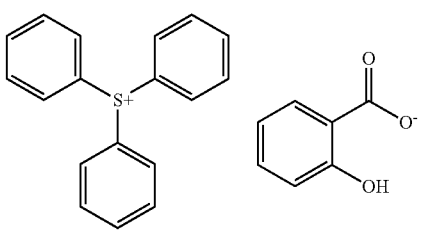

-continued

N-6

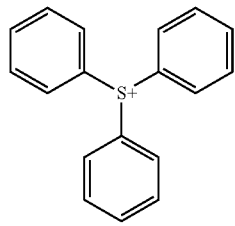

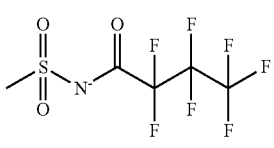

N-7

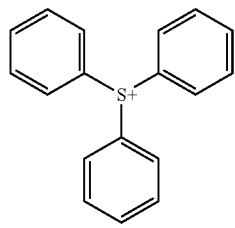

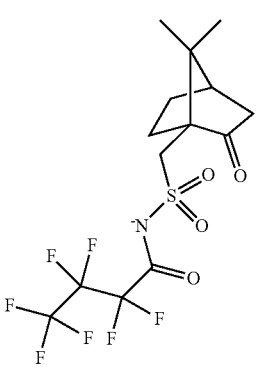

[Hydrophobic Resin]

The molar ratios, the weight-average molecular weights (Mw), and the dispersities (Mw/Mn) of the repeating units are also shown below, in addition to the structures of the repeating units in the respective resins.

(1b)

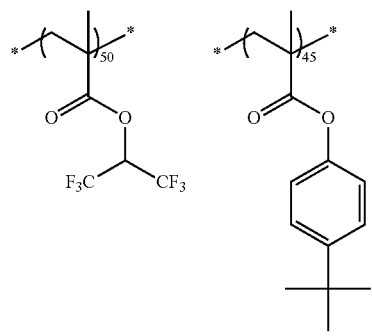

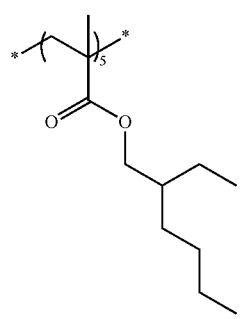

Mw = 7000
Mw/Mn = 1.30

-continued (2b)

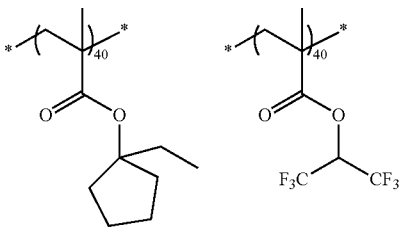

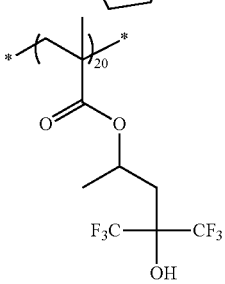

Mw = 18600
Mw/Mn = 1.57

(3b)

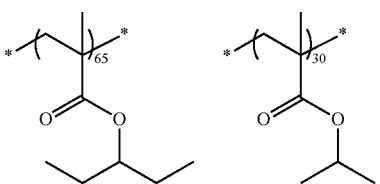

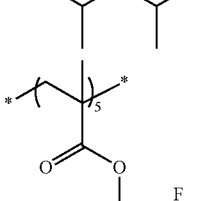

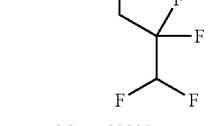

Mw = 28000
Mw/Mn = 1.70

[Surfactant]
W-1: PolyFox PF-6320 (manufactured by OMNOVA Solutions Inc.; fluorine-based)

[Solvent]
SL-1: Propylene glycol monomethyl ether acetate (PGMEA: 1-methoxy-2-acetoxypropane)
SL-2: Propylene glycol monomethyl ether (PGME: 1-methoxy-2-propanol)
SL-3: Cyclohexanone
SL-4: γ-Butyrolactone From the results shown in Table 2, in Examples using the composition of the embodiment of the present invention, in the formation of an ultrafine pattern which is referred to as a line-and-space pattern with a line width of 44 nm, the roughness performance, the exposure latitude, and the depth of focus were very excellent, as compared with Comparative Examples not using the composition of the embodiment of the present invention.

According to the present invention, it is possible to provide an actinic ray-sensitive or radiation-sensitive resin composition which can provide very excellent roughness performance, exposure latitude, and depth of focus, particularly, in the formation of an ultrafine pattern (for example, a contact hole pattern having a hole diameter of 45 nm or less, or a line-and-space pattern having a line width of 45 nm or less); a photoacid generator; and an actinic ray-sensitive or radiation-sensitive film, a pattern forming method, and a method for manufacturing an electronic device, each using the actinic ray-sensitive or radiation-sensitive resin composition.

Although the present invention has been described in detail and with reference to specific embodiments, it is obvious to those skilled in the art that various changes or modifications can be made without departing from the spirit and scope of the present invention.

What is claimed is:

1. An actinic ray-sensitive or radiation-sensitive resin composition, comprising:
    (A) a photoacid generator that generates an acid having a pKa of −1.40 or more upon irradiation with actinic rays or radiation; and
    (B) a resin having a repeating unit containing an acid-decomposable group,
    wherein an Eth sensitivity of the repeating unit containing an acid-decomposable group is 5.64 or less, and
    the acid generated by the photoacid generator (A) upon irradiation with actinic rays or radiation is a sulfonic acid represented by any one of General Formulas (b) and (I) to (V),

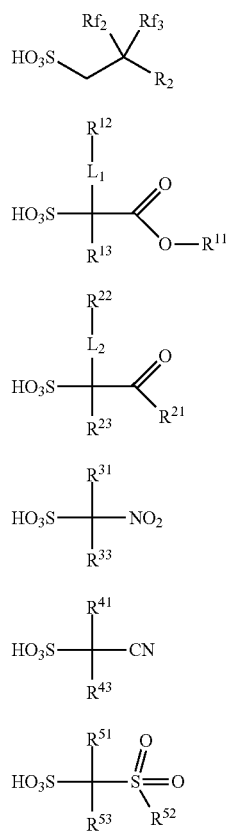

in General Formula (b), $Rf_2$ and $Rf_3$ each independently represents a fluorine atom or an alkyl group containing a fluorine atom, and $R_2$ represents a monovalent organic group, in General Formula (I), $R^{11}$ and $R^{12}$ each independently represents a monovalent organic group, $R^{13}$ represents a hydrogen atom or a monovalent organic group, $L_i$ represents a group represented by —CO—O—, —CO—, —O—, —S—, —O—CO—, —S—CO—, or —CO—S—, and two of $R^{11}$, $R^{12}$, and $R^{13}$ may be bonded to each other to form a ring, in General Formula (II), $R^{21}$ and $R^{22}$ each independently represents a monovalent organic group, $R^{23}$ represents a hydrogen atom or a monovalent organic group, $L_2$ represents a group represented by —CO—, —O—, —S—, —O—CO—, —S—CO—, or -CO-S-, and two of $R^{21}$, $R^{22}$, and $R^{23}$ may be bonded to each other to form a ring, in General Formula (III), $R^{31}$ and $R^{33}$ each independently represents a hydrogen atom or a monovalent organic group, and $R^{31}$ and $R^{33}$ may be bonded to each other to form a ring, in General Formula (IV), $R^{41}$ and $R^{43}$ each independently represents a hydrogen atom or a monovalent organic group, and $R^{41}$ and $R^{43}$ may be bonded to each other to form a ring, and in General Formula (V), $R^{51}$, $R^{52}$, and $R^{53}$ each independently represents a hydrogen atom or a monovalent organic group, and two of $R^{51}$, $R^{52}$, and $R^{53}$ may be bonded to each other to form a ring.

2. The actinic ray-sensitive or radiation-sensitive resin composition according to claim 1,
    wherein the acid having a pKa of −1.40 or more is a sulfonic acid.

3. The actinic ray-sensitive or radiation-sensitive resin composition according to claim 2,
    wherein the sulfonic acid is an alkyl sulfonic acid in which one fluorine atom is bonded to a carbon atom at an α-position of a sulfonic acid group.

4. The actinic ray-sensitive or radiation-sensitive resin composition according to claim 1,
    wherein the resin (B) is a resin having a repeating unit represented by General Formula (A) or (B) as the repeating unit containing an acid-decomposable group,

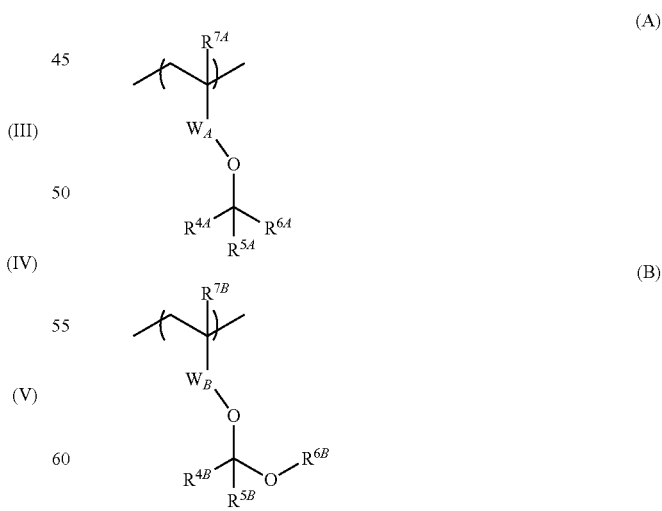

in General Formula (A), $R^{4A}$, $R^{5A}$, and $R^{6A}$ each independently represent a monovalent organic group, $W_A$ represents —CO— or a divalent aromatic ring group, $R^{7A}$ represents a hydrogen atom, a methyl group, or a trifluoromethyl group, and $R^{5A}$ and $R^{6A}$ may be bonded to each other to form a ring, and in General Formula (B), $R^{4B}$, $R^{5B}$, and $R^{6B}$ each independently represent a hydrogen atom or a monovalent organic group, $R^{5B}$ and $R^{6B}$ may be bonded to each other to form a ring, $W_B$ represents —CO— or a divalent aromatic ring group, and $R^{7B}$ represents a hydrogen atom, a methyl group, or a trifluoromethyl group.

5. The actinic ray-sensitive or radiation-sensitive resin composition according to claim 1, which does not contain a photoacid generator that generates an acid having a pKa of less than −1.40 upon irradiation with actinic rays or radiation.

6. An actinic ray-sensitive or radiation-sensitive film formed using the actinic ray-sensitive or radiation-sensitive resin composition according to claim 1.

7. A pattern forming method comprising:
a step of forming an actinic ray-sensitive or radiation-sensitive film using the actinic ray-sensitive or radiation-sensitive resin composition according to claim 1;
a step of irradiating the actinic ray-sensitive or radiation-sensitive film with actinic rays or radiation; and
a step of developing the actinic ray-sensitive or radiation-sensitive film irradiated with actinic rays or radiation.

8. A method for manufacturing an electronic device, comprising the pattern forming method according to claim 7.

9. A photoacid generator generating a sulfonic acid upon irradiation with actinic rays or radiation, represented by any one of General Formulas (b) and (I) to (V):

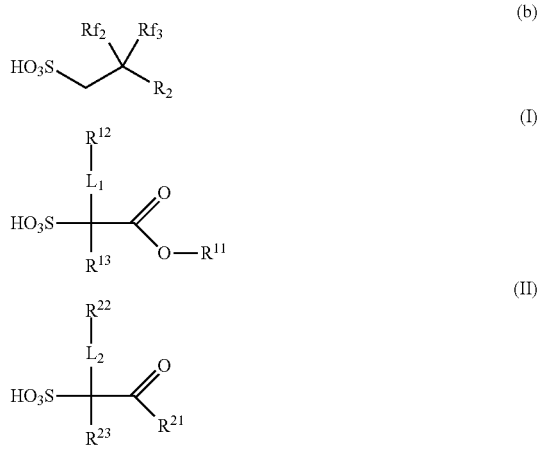

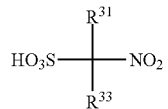

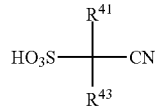

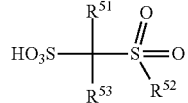

in General Formula (b), $Rf_2$ and $Rf_3$ each independently represents a fluorine atom or an alkyl group containing a fluorine atom, and $R_2$ represents a monovalent organic group, in General Formula (I), $R^{11}$ and $R^{12}$ each independently represents a monovalent organic group, $R^{13}$ represents a hydrogen atom or a monovalent organic group, $L_1$ represents a group represented by —CO—O—, —CO—, —O—, —S—, —O—CO—, —S—CO—, or —CO—S—, and two of $R^{11}$, $R^{12}$, and $R^{13}$ may be bonded to each other to form a ring, in General Formula (II), $R^{21}$ and $R^{22}$ each independently represents a monovalent organic group, $R^{23}$ represents a hydrogen atom or a monovalent organic group, $L_2$ represents a group represented by —CO—, —O—, —S—, —O—CO—, —S—CO—, or —CO—S—, and two of $R^{21}$, $R^{22}$, and $R^{23}$ may be bonded to each other to form a ring, in General Formula (III), $R^{31}$ and $R^{33}$ each independently represents a hydrogen atom or a monovalent organic group, and $R^{31}$ and $R^{33}$ may be bonded to each other to form a ring, in General Formula (IV), $R^{41}$ and $R^{43}$ each independently represents a hydrogen atom or a monovalent organic group, and $R^{41}$ and $R^{43}$ may be bonded to each other to form a ring, and in General Formula (V), $R^{51}$, $R^{52}$, and $R^{53}$ each independently represents a hydrogen atom or a monovalent organic group, and two of $R^{51}$, $R^{52}$, and $R^{53}$ may be bonded to each other to form a ring.

* * * * *